United States Patent
Sexton et al.

(10) Patent No.: US 11,372,002 B2
(45) Date of Patent: Jun. 28, 2022

(54) ASSAYS FOR DETERMINING PLASMA KALLIKREIN SYSTEM BIOMARKERS

(71) Applicant: Takeda Pharmaceutical Company Limited, Osaka (JP)

(72) Inventors: Daniel J. Sexton, Melrose, MA (US); Ryan Faucette, Melrose, MA (US); Jon A. Kenniston, Hingham, MA (US); Gregory P. Conley, Arlington, MA (US); Andrew Nixon, Hanover, MA (US); Christopher TenHoor, Hopkinton, MA (US); Burt Adelman, Concord, MA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 677 days.

(21) Appl. No.: 15/030,811

(22) PCT Filed: Oct. 17, 2014

(86) PCT No.: PCT/US2014/061247
§ 371 (c)(1),
(2) Date: Apr. 20, 2016

(87) PCT Pub. No.: WO2015/061183
PCT Pub. Date: Apr. 30, 2015

(65) Prior Publication Data
US 2016/0252527 A1      Sep. 1, 2016

Related U.S. Application Data

(60) Provisional application No. 61/939,837, filed on Feb. 14, 2014, provisional application No. 61/893,505, filed on Oct. 21, 2013.

(51) Int. Cl.
| | |
|---|---|
| *G01N 33/68* | (2006.01) |
| *C07K 16/40* | (2006.01) |
| *C12Q 1/37* | (2006.01) |
| *C12Q 1/56* | (2006.01) |
| *C07K 16/36* | (2006.01) |
| *A61K 39/00* | (2006.01) |

(52) U.S. Cl.
CPC ......... *G01N 33/6893* (2013.01); *C07K 16/36* (2013.01); *C07K 16/40* (2013.01); *C12Q 1/37* (2013.01); *C12Q 1/56* (2013.01); *A61K 2039/505* (2013.01); *C07K 2317/76* (2013.01); *C12Y 304/21034* (2013.01); *C12Y 304/21038* (2013.01); *G01N 2333/4713* (2013.01); *G01N 2333/96455* (2013.01); *G01N 2333/96458* (2013.01); *G01N 2500/02* (2013.01); *G01N 2500/20* (2013.01); *G01N 2800/224* (2013.01); *G01N 2800/50* (2013.01); *G01N 2800/52* (2013.01)

(58) Field of Classification Search
CPC .......... C12Q 1/56; C07K 16/36; C07K 16/40; C12Y 304/21034; C12Y 304/21038; G01N 2333/96455; G01N 2333/96458; G01N 2500/02; G01N 2800/52
See application file for complete search history.

(56) References Cited

U.S. PATENT DOCUMENTS

| | | | |
|---|---|---|---|
| 4,882,272 A | 11/1989 | Scott et al. | |
| 4,908,431 A | 3/1990 | Colman et al. | |
| 4,985,354 A | 1/1991 | Toyomaki et al. | |
| 5,025,796 A | 6/1991 | Hargreaves et al. | |
| 5,047,323 A | 9/1991 | Colman et al. | |
| 5,472,945 A | 12/1995 | Schmaier et al. | |
| 6,242,210 B1 | 6/2001 | Bjoerck et al. | |
| 6,913,900 B2 | 7/2005 | Kaplan et al. | |
| 10,101,344 B2 | 10/2018 | Sexton et al. | |
| 10,648,990 B2 | 5/2020 | Sexton et al. | |
| 10,914,747 B2 | 2/2021 | Sexton et al. | |
| 11,156,612 B2 | 10/2021 | Sexton et al. | |
| 2005/0223416 A1 | 10/2005 | Nuijens et al. | |
| 2006/0069020 A1 | 3/2006 | Blair et al. | |
| 2006/0115471 A1 | 6/2006 | Coleman et al. | |
| 2007/0192882 A1 | 8/2007 | Dewald | |
| 2008/0038276 A1 | 2/2008 | Sinha et al. | |
| 2008/0299549 A1 | 12/2008 | Sorge et al. | |
| 2009/0075887 A1 | 3/2009 | McPherson | |
| 2011/0154517 A1 | 6/2011 | Dewald | |
| 2011/0200611 A1 | 8/2011 | Sexton | |
| 2011/0212104 A1 | 9/2011 | Beaumont et al. | |
| 2011/0318359 A1 | 12/2011 | Feener et al. | |
| 2012/0201756 A1 | 8/2012 | Sexton | |
| 2013/0156753 A1 | 6/2013 | Jin | |
| 2014/0128436 A1 | 5/2014 | Sinha et al. | |

(Continued)

FOREIGN PATENT DOCUMENTS

| | | |
|---|---|---|
| CN | 102405228 A | 4/2012 |
| CN | 102762203 A2 | 10/2012 |

(Continued)

OTHER PUBLICATIONS

Veloso et al. (Blood, vol. 70, No. 4 Oct. 1987, p. 1053-1062).*
U.S. Appl. No. 15/030,790, filed Apr. 20, 2016, Pending.
U.S. Appl. No. 14/761,690, filed Jul. 17, 2015, Published, 2015-0362493.
PCT/US2014/061242, Feb. 3, 2015, International Search Report and Written Opinion.
PCT/US2014/061242, May 6, 2016, International Preliminary Report on Patentability.

(Continued)

*Primary Examiner* — Sharon X Wen
(74) *Attorney, Agent, or Firm* — Wolf, Greenfield & Sacks, P.C.

(57) ABSTRACT

Methods and assays for determining the activation level of the plasma kallikrein (pKal) system and the uses thereof for assessing the activity of pKal modulators on the pKal system.

15 Claims, 30 Drawing Sheets
Specification includes a Sequence Listing.

(56) References Cited

U.S. PATENT DOCUMENTS

| | | |
|---|---|---|
| 2015/0362493 A1 | 12/2015 | Sexton et al. |
| 2016/0252533 A1 | 9/2016 | Sexton et al. |
| 2018/0306807 A1 | 10/2018 | Sexton et al. |
| 2019/0120862 A1 | 4/2019 | Sexton et al. |
| 2020/0371120 A1 | 11/2020 | Sexton et al. |
| 2021/0270842 A1 | 9/2021 | Sexton et al. |

FOREIGN PATENT DOCUMENTS

| | | |
|---|---|---|
| EP | 0 210 029 A2 | 1/1987 |
| JP | S63-185398 A | 7/1988 |
| JP | H10-84995 A | 4/1998 |
| JP | 2001-503861 A | 5/1998 |
| JP | 2001-124779 A | 5/2001 |
| JP | 2002-221519 A | 8/2002 |
| JP | 2003-159053 A | 6/2003 |
| JP | 2009-521926 A | 6/2009 |
| JP | 2013-516389 A | 5/2013 |
| JP | 2014-506319 A | 3/2014 |
| JP | 2016-505159 A | 2/2016 |
| JP | 2016-511823 A | 4/2016 |
| JP | 2016-536012 A | 11/2016 |
| JP | 2017-500584 A | 1/2017 |
| JP | 2017-503820 A | 2/2017 |
| KR | 10-2010-0120788 A | 11/2010 |
| KR | 10-2011-0057086 A | 5/2011 |
| WO | WO 2006/101387 A2 | 9/2006 |
| WO | WO 2007/079096 A2 | 7/2007 |
| WO | WO 2011/075684 A1 | 6/2011 |
| WO | WO 2012/094587 | 7/2012 |
| WO | WO 2012/170945 A2 | 12/2012 |
| WO | WO 2012/170947 A2 | 12/2012 |
| WO | WO 2014/113712 A1 | 7/2014 |
| WO | WO 2015/061182 A1 | 4/2015 |
| WO | WO 2015/061183 A1 | 4/2015 |

OTHER PUBLICATIONS

PCT/US2014/012107, Apr. 14, 2014, International Search Report and Written Opinion.

PCT/US2014/012107, Jul. 30, 2015, International Preliminary Report on Patentability.

PCT/US2014/061247, Feb. 4, 2015, International Search Report and Written Opinion.

PCT/US2014/061247, May 6, 2016, International Preliminary Report on Patentability.

[No Author Listed], Image Studio Software Compatible with Mac® Systems Now Available from LI-COR!. BioB Blog. May 8, 2012:1-3.

Berrettini et al., Detection of in vitro and in vivo cleavage of high molecular weight kininogen in human plasma by immunoblotting with monoclonal antibodies. Blood. Aug. 1986;68(2):455-62.

Blais et al., The kallikrein-kininogen-kinin system: lessons from the quantification of endogenous kinins. Peptides. Dec. 2000;21(12):1903-40. Review.

Chyung et al., A phase 1 study investigating DX-2930 in healthy subjects. Ann Allergy Asthma Immunol. Oct. 2014;113(4):460-6.e2. doi: 10.1016/j.anai.2014.05.028. Epub Jun. 26, 2014.

Colman et al., Studies on the prekallikrein (kallikreinogen)—kallikrein enzyme system of human plasma. I. Isolation and purification of plasma kallikreins. J Clin Invest. Jan. 1969;48(1):11-22.

Cugno et al., Activation of the coagulation cascade in C1-inhibitor deficiencies. Blood. May 1, 1997;89(9):3213-8.

Cugno et al., Activation of the contact system and fibronolysis in autoimmune acquired angioedema: A rationale for prophylactic use of tranexamic acid. J Allergy Clin Immunol. 1994;93(5):870-876.

Defendi et al., Enzymatic assays for the diagnosis of bradykinin-dependent angioedema. PLoS One. Aug. 5, 2013;8(8):e70140. doi: 10.1371/journal.pone.0070140. Print 2013. Erratum in: PLoS One. 2014;9(6):e100345.

Dobóet al., Cleavage of kininogen and subsequent bradykinin release by the complement component: mannose-binding lectin-associated serine protease (MASP)-1. PLoS One. 2011;6(5):e20036. doi: 10.1371/journal.pone.0020036. Epub May 23, 2011.

Faucette et al., A Biomarker Assay For the Detection of Contact System Activation. Blood. 2013;122:2347. Avaible online at http://www.bloodjournal.org/conten/122/21/2347. Last accessed on Mar. 30, 2018. Abstract only.

Isordia-Salas et al., The role of plasma high molecular weight kininogen in experimental intestinal and systemic inflammation. Arch Med Res. Jan.-Feb. 2005;36(1):87-95.

Joseph et al., Studies of the mechanisms of bradykinin generation in hereditary angioedema plasma. Ann Allergy Asthma Immunol. Sep. 2008;101(3):279-86. doi: 10.1016/S1081-1206(10)60493-0.

Katori et al., Evidence for the involvement of a plasma kallikrein-kinin system in the immediate hypotension produced by endotoxin in anaesthetized rats. Br J Pharmacol. Dec. 1989;98(4):1383-91.

Khan et al., High-molecular-weight kininogen fragments stimulate the secretion of cytokines and chemokines through uPAR, Mac-1, and gC1qR in monocytes. Arterioscler Thromb Vasc Biol. Oct. 2006;26(10):2260-6. Epub Aug. 10, 2006. Erratum in: Arterioscler Thromb Vasc Biol. Nov. 2006;26(11):e146.

Ladner et al., Discovery of Ecallantide: A Potent and Selective Inhibitor of Plasma Kallikrein. J Allergy and Clinical Immuno. Jan. 1, 2007;119(1):S312.

Merlo et al., Elevated levels of plasma prekallikrein, high molecular weight kininogen and factor XI in coronary heart disease. Atherosclerosis. Apr. 2002;161(2):261-7.

Nielsen et al., Hereditary angio-oedema: new clinical observations and autoimmune screening, complement and kallikrein-kinin analyses. J Intern Med. Feb. 1996;239(2): 119-30.

Page et al., An autoantibody to human plasma prekallikrein blocks activation of the contact system. Br J Haematol. May 1994;87(1):81-6.

Raymond et al., Quantification of des-Arg9-bradykinin using a chemiluminescence enzyme immunoassay: application to its kinetic profile during plasma activation. J Immunol Methods. Mar. 27, 1995;180(2):247-57.

Reddigari et al., Cleavage of human high-molecular weight kininogen by purified kallikreins and upon contact activation of plasma. Blood. May 1988;71(5): 1334-40.

Reddigari et al., Quantification of human high molecular weight kininogen by immunoblotting with a monoclonal anti-light chain antibody. J Immunol Methods. Apr. 21, 1989;119(1):19-25.

Schmaier et al., Determination of the bifunctional properties of high molecular weight kininogen by studies with monoclonal antibodies directed to each of its chains. J Biol Chem. Jan. 25, 1987;262(3):1405-11.

Schousboe et al., High molecular wieht kininogen binds to laminin—characterization and kinetic analyis. FEBS Journal. 2009;276:5228-5238.

Torzewski et al., Animal Models of c-Reactive Protein. Hindawi Publishing Corpl, Mediators of Inflammation. 2014:1-7.

Van Der Vekens et al., Human and equine cardiovascular endrocrinology: beware to compare. Cardivosacular Endicronology. 2013;2(4):67-76.

Williams et al., DX-88 and HAE: a developmental perspective. Transfus Apher Sci. Dec. 2003;29(3):255-8.

Zhang et al., Two-chain high molecular weight kininogen induces endothelial cell apoptosis and inhibits angiogenesis: partial activity within domain 5. FASEB J. Dec. 2000;14(15):2589-600.

Bühler et al., Improved detection of proteolytically cleaved high molecular weight kininogen by immunoblotting using an antiserum against its reduced 47 kDa light chain. Blood Coagul Fibrinolysis. May 1995;6(3):223-32.

Gallimore et al., Plasma levels of factor XII, prekallikrein and high molecular weight kininogen in normal blood donors and patients having suffered venous thrombosis. Thromb Res. 2004;114(2):91-6.

Isordia-Salas et al., The mutation Ser511Asn leads to N-glycosylation and increases the cleavage of high molecular weight kininogen in rats genetically susceptible to inflammation. Blood. Oct. 15, 2003;102(8):2835-42. Epub Jul. 3, 2003.

(56) References Cited

OTHER PUBLICATIONS

Kerbiriou-Nabias et al., Radioimmunoassays of human high and low molecular weight kininogens in plasmas and platelets. Br J Haematol. Feb. 1984;56(2):273-86.
Nguyen et al., The Simple Western™: a gel-free, blot-free, hands-free Western blotting reinvention. Nature Methods. Oct. 28, 2011;8:5-6.
Phipps et al., Plasma kallikrein mediates angiotensin II type 1 receptor-stimulated retinal vascular permeability. Hypertension. Feb. 2009;53(2):175-81. Epub Jan. 5, 2009.
Reddigari et al., Monoclonal antibody to human high-molecular-weight kininogen recognizes its prekallikrein binding site and inhibits its coagulant activity. Blood. Aug. 1, 1989;74(2):695-702.
Scott et al., A new assay for high molecular weight kininogen in human plasma using a chromogenic substrate. Thromb Res. Dec. 15, 1987;48(6):685-700.
U.S. Appl. No. 15/030,790, filed Apr. 20, 2016, Published, 2016-0252533.
EP 14855002.3, Feb. 20, 2017, Supplementary European Searh Report.
EP 14740444.6, Jun. 17, 2016, Extended European Search Report.
EP 14856778.7, Feb. 28, 2017, Partial Supplementary European Search Report.
EP 14856778.7, Jun. 16, 2017, Supplementary European Search Report.
U.S. Appl. No. 15/030,790, filed Apr. 20, 2016, Granted, U.S. Appl. No. 10,101,344.
U.S. Appl. No. 16/131,781, filed Sep. 14, 2018, Pending.
U.S. Appl. No. 14/761,690, filed Jul. 17, 2015, Published, 2015-03624932.
U.S. Appl. No. 15/769,237, filed Apr. 18, 2018, Published, 2018-03068071.
EP 18186356.4, Jan. 18, 2019, Extended European Search Report.
PCT/US2016/057640, May 3, 2018, International Preliminary Report on Patentability.
PCT/US2016/057640, Jan. 26, 2017, International Search Report and Written Opinion.
[No Author Listed], Mouse High Molecular Weight Kinnogen (HMWK) ELISA Kit (Cat. No. BMS089195). MyBiosource Datasheet. Jan. 2, 1984. Revtrieved from <https://www.mybiosource.com/prods/ELIS-A-Kit/Mouse/High-Molecular-Weight-Kinogen/HMWK/datasheet.php?products_id=89195> on Dec. 13, 2018. 4 pages.
Ishiguro et al., Mapping of functional domains of human high molecular weight and low molecular weight kininogens using murine monoclonal antibodies. Biochemistry. Nov. 3, 1987;26(22):7021-9.
Scott et al., Sensitive antigenic determinations of high molecular weight kininogen performed by covalent coupling of capture antibody. J Lab Clin Med. Jan. 1992;119(1):77-86. Abstract only.
Syvänen et al., A radioimmunoassay for the detection of molecular forms of human plasma kininogen. FEBS Lett. Jul. 6, 1981;129(2):241-5.
Uchida et al., Differential assay method for high molecular weight and low molecular weight kininogens. Thromb Res. 1979;15(1-2):127-34.
Cugno et al., Activation of factor XII and cleavage of high molecular weight kininogen during acute attacks in hereditary and acquired C1-inhibitor deficiencies. Immunopharmacology. Jun. 1996;33(1-3):361-4.
Devani et al., Kallikrein-kinin system activation in Crohn's disease: differences in intestinal and systemic markers. Am J Gastroenterol. Aug. 2002;97(8):2026-32.
Chaudhuri et al., Glucocorticoids and rheumatoid arthritis—a reappraisal. I. J. Rheumatol. Mar. 1, 2008;3(1):21-8.
Cugno et al., C1-inhibitor deficiency and angioedema: molecular mechanisms and clinical progress. Trends Mol Med. Feb. 2009;15(2):69-78. doi: 10.1016/j.molmed.2008.12.001. Epub Jan. 21, 2009.
Huang, Alzheimer Disease. Merck Manual, Professional Version. Dec. 2019:1-7.
Kenniston et al., Inhibition of plasma kallikrein by a highly specific active site blocking antibody. J Biol Chem. Aug. 22, 2014;289(34):23596-608. doi: 10.1074/jbc.M114.569061. Epub Jun. 26, 2014.
Kontzias, Rheumatoid Arthritis (RA). Merck Manual, Professional Version. Dec. 2018:1-19.
Maggio, Sepsis and Septic Shock. Merck Manual, Professional Version. Jan. 2020:1-8.
Mehta, Diabetic Retinopathy. Merck Manual, Professional Version. Jun. 2019:1-5.
Sexton et al., Discovery and Characterization of a Fully Human Monoclonal Antibody Inhibitor of Plasma Kallikrein for the Treatment of Plasma Kallikrein-Mediated Edema. J. Allergy Clin. Immunol. Feb. 2013;131(2): AB32.
Mutch et al., Immobilized transition metal ions stimulate contact activation and drive factor XII-mediated coagulation. J Thromb Haemost. Oct. 2012;10(10):2108-15. doi: 10.1111/j.1538-7836.2012.04890.x.
Sexton et al., Inhibition of the plasma kallikrein-kinin system activation by DX-2930, a fully human monoclonal antibody inhibitor of plasma kallikrein. Journal of Angioedema. May 2013; 1(1): 45.
Zuraw et al., New promise and hope for treating hereditary angioedema. Expert Opin Investig Drugs. May 2008;17(5):697-706. doi: 10.1517/13543784.17.5.697.
U.S. Appl. No. 17/141,690, filed Jan. 5, 2021, Sexton et al.
EP 20197583.6, Mar. 19, 2021, Extended European Search Report.
Babu et al., A Simple, Sensitive and Selective Fluorogenic Assay To Monitor Plasma Kallikrein Inhibitory Activity Of BCX4161 In Activated Plasma. J Allergy Clin Immunol. Feb. 2014; 133(2):1.
Bantia et al., BCX-4161, a Small Molecule and Orally Bioavailable Plasma Kallikrein Inhibitor for the Treatment of Hereditary Angioedema. J Allergy Clin Immunol. Feb. 2013;131(2):1.
Zhang et al., A Simple, Sensitive and Selective Fluorogenic Assay to Monitor Kallikrein Activity in Activated Plasma. J Allergy Clin Immunol. Feb. 2013;131(2):1-4.

* cited by examiner

Quantitation of Intact 1 Chain Kininogen
by Western Blot in HAE Patient ANTI-PROTEASE Plasma

Figure 12
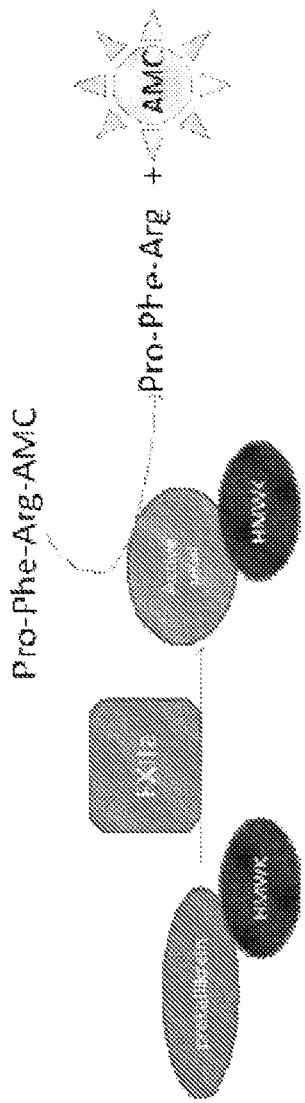
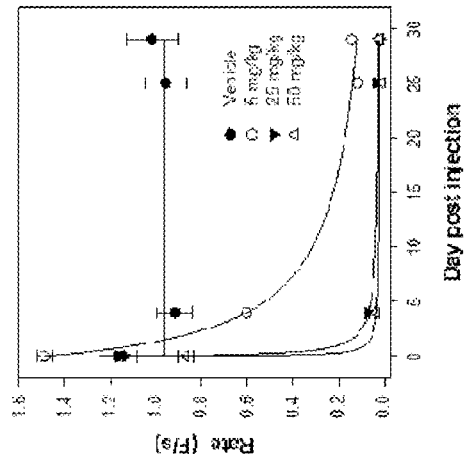
*Protocol*
- 2930 added to neat plasma
- Dilute 1:40 with buffer and add to 96-well microplate
- Add concentrated "activator" (FXIIa)
- Incubate on ice 2 minutes
- Stop activation with addition of corn trypsin inhibitor (CTI)
- Dilute further 1:10 for measurement of proteolytic activity against fluorescent peptide substrate Estimated 1 Chain Kininogen Concentrations in HAE Patient Plasma (samples from 10 patients during attack and 15 patients during basal conditons) Error = SEM

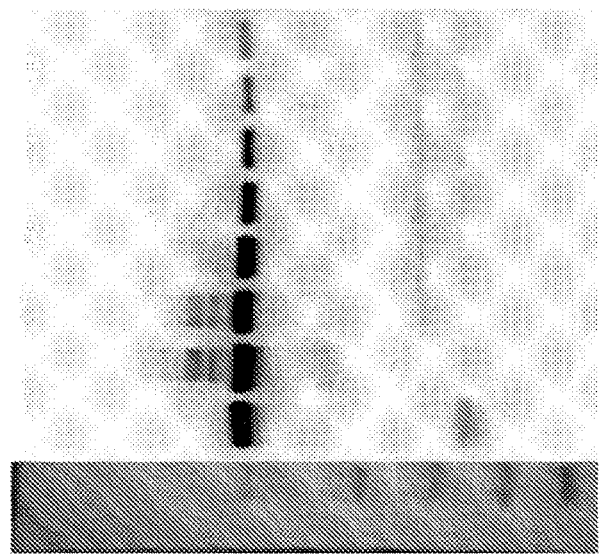
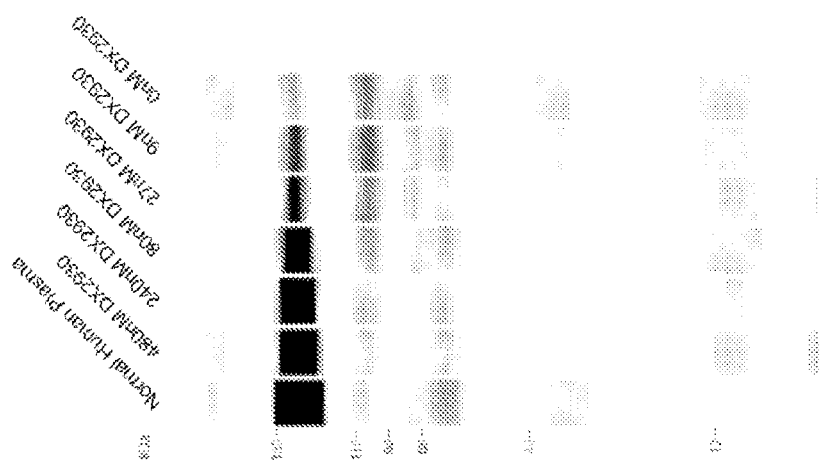
Figure 17

Estimated 2 Chain Kininogen Concentrations in HAE Patient Plasma
(samples from 10 patients during attack and 15 patients during basal conditons)

SEQUENCE LISTING

<160> NUMBER OF SEQ ID NOS: 7

<210> SEQ ID NO 1
<211> LENGTH: 304
<212> TYPE: PRT
<213> ORGANISM: Artificial Sequence
<220> FEATURE:
<223> OTHER INFORMATION: Synthetic Polypeptide

<400> SEQUENCE: 1

```
Met Ile Tyr Thr Met Lys Lys Val His Ala Leu Trp Ala Ser Val Cys
1               5                   10                  15

Leu Leu Leu Asn Leu Ala Pro Ala Pro Leu Asn Ala Asp Ser Glu Glu
            20                  25                  30

Asp Glu Glu His Thr Ile Ile Thr Asp Thr Glu Leu Pro Pro Leu Lys
        35                  40                  45

Leu Met His Ser Phe Cys Ala Phe Lys Ala Asp Asp Gly Pro Cys Lys
    50                  55                  60

Ala Ile Met Lys Arg Phe Phe Phe Asn Ile Phe Thr Arg Gln Cys Glu
65                  70                  75                  80

Glu Phe Ile Tyr Gly Gly Cys Glu Gly Asn Gln Asn Arg Phe Glu Ser
                85                  90                  95

Leu Glu Glu Cys Lys Lys Met Cys Thr Arg Asp Asn Ala Asn Arg Ile
            100                 105                 110

Ile Lys Thr Thr Leu Gln Gln Glu Lys Pro Asp Phe Cys Phe Leu Glu
        115                 120                 125

Glu Asp Pro Gly Ile Cys Arg Gly Tyr Ile Thr Arg Tyr Phe Tyr Asn
    130                 135                 140

Asn Gln Thr Lys Gln Cys Glu Arg Phe Lys Tyr Gly Gly Cys Leu Gly
145                 150                 155                 160

Asn Met Asn Asn Phe Glu Thr Leu Glu Glu Cys Lys Asn Ile Cys Glu
                165                 170                 175

Asp Gly Pro Asn Gly Phe Gln Val Asp Asn Tyr Gly Thr Gln Leu Asn
            180                 185                 190

Ala Val Asn Asn Ser Leu Thr Pro Gln Ser Thr Lys Val Pro Ser Leu
        195                 200                 205

Phe Glu Phe His Gly Pro Ser Trp Cys Leu Thr Pro Ala Asp Arg Gly
    210                 215                 220

Leu Cys Arg Ala Asn Glu Asn Arg Phe Tyr Tyr Asn Ser Val Ile Gly
225                 230                 235                 240

Lys Cys Arg Pro Phe Lys Tyr Ser Gly Cys Gly Gly Asn Glu Asn Asn
                245                 250                 255
```

```
Phe Thr Ser Lys Gln Glu Cys Leu Arg Ala Cys Lys Lys Gly Phe Ile
            260                 265                 270

Gln Arg Ile Ser Lys Gly Gly Leu Ile Lys Thr Lys Arg Lys Arg Lys
        275                 280                 285

Lys Gln Arg Val Lys Ile Ala Tyr Glu Glu Ile Phe Val Lys Asn Met
    290                 295                 300

<210> SEQ ID NO 2
<211> LENGTH: 58
<212> TYPE: PRT
<213> ORGANISM: Artificial Sequence
<220> FEATURE:
<223> OTHER INFORMATION: Synthetic Polypeptide

<400> SEQUENCE: 2

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
    50                  55

<210> SEQ ID NO 3
<211> LENGTH: 60
<212> TYPE: PRT
<213> ORGANISM: Artificial Sequence
<220> FEATURE:
<223> OTHER INFORMATION: Synthetic Polypeptide

<400> SEQUENCE: 3

Glu Ala Met His Ser Phe Cys Ala Phe Lys Ala Asp Asp Gly Pro Cys
1               5                   10                  15

Arg Ala Ala His Pro Arg Trp Phe Phe Asn Ile Phe Thr Arg Gln Cys
            20                  25                  30

Glu Glu Phe Ile Tyr Gly Gly Cys Glu Gly Asn Gln Asn Arg Phe Glu
        35                  40                  45

Ser Leu Glu Glu Cys Lys Lys Met Cys Thr Arg Asp
    50                  55                  60

<210> SEQ ID NO 4
<211> LENGTH: 58
<212> TYPE: PRT
<213> ORGANISM: Artificial Sequence
<220> FEATURE:
<223> OTHER INFORMATION: Synthetic Polypeptide

<400> SEQUENCE: 4

Met His Ser Phe Cys Ala Phe Lys Ala Asp Asp Gly Pro Cys Arg Ala
1               5                   10                  15

Ala His Pro Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 5
<211> LENGTH: 644
<212> TYPE: PRT
```

<213> ORGANISM: Homo sapiens

<400> SEQUENCE: 5

Met Lys Leu Ile Thr Ile Leu Phe Leu Cys Ser Arg Leu Leu Leu Ser
1               5                   10                  15

Leu Thr Gln Glu Ser Gln Ser Glu Glu Ile Asp Cys Asn Asp Lys Asp
            20                  25                  30

Leu Phe Lys Ala Val Asp Ala Ala Leu Lys Lys Tyr Asn Ser Gln Asn
        35                  40                  45

Gln Ser Asn Asn Gln Phe Val Leu Tyr Arg Ile Thr Glu Ala Thr Lys
    50                  55                  60

Thr Val Gly Ser Asp Thr Phe Tyr Ser Phe Lys Tyr Glu Ile Lys Glu
65                  70                  75                  80

Gly Asp Cys Pro Val Gln Ser Gly Lys Thr Trp Gln Asp Cys Glu Tyr
                85                  90                  95

Lys Asp Ala Ala Lys Ala Ala Thr Gly Glu Cys Thr Ala Thr Val Gly
            100                 105                 110

Lys Arg Ser Ser Thr Lys Phe Ser Val Ala Thr Gln Thr Cys Gln Ile
        115                 120                 125

Thr Pro Ala Glu Gly Pro Val Val Thr Ala Gln Tyr Asp Cys Leu Gly
    130                 135                 140

Cys Val His Pro Ile Ser Thr Gln Ser Pro Asp Leu Glu Pro Ile Leu
145                 150                 155                 160

Arg His Gly Ile Gln Tyr Phe Asn Asn Asn Thr Gln His Ser Ser Leu
                165                 170                 175

Phe Met Leu Asn Glu Val Lys Arg Ala Gln Arg Gln Val Val Ala Gly
            180                 185                 190

Leu Asn Phe Arg Ile Thr Tyr Ser Ile Val Gln Thr Asn Cys Ser Lys
        195                 200                 205

Glu Asn Phe Leu Phe Leu Thr Pro Asp Cys Lys Ser Leu Trp Asn Gly
    210                 215                 220

Asp Thr Gly Glu Cys Thr Asp Asn Ala Tyr Ile Asp Ile Gln Leu Arg
225                 230                 235                 240

Ile Ala Ser Phe Ser Gln Asn Cys Asp Ile Tyr Pro Gly Lys Asp Phe
                245                 250                 255

Val Gln Pro Pro Thr Lys Ile Cys Val Gly Cys Pro Arg Asp Ile Pro
            260                 265                 270

Thr Asn Ser Pro Glu Leu Glu Glu Thr Leu Thr His Thr Ile Thr Lys
        275                 280                 285

Leu Asn Ala Glu Asn Asn Ala Thr Phe Tyr Phe Lys Ile Asp Asn Val
    290                 295                 300

Lys Lys Ala Arg Val Gln Val Val Ala Gly Lys Lys Tyr Phe Ile Asp
305                 310                 315                 320

Phe Val Ala Arg Glu Thr Thr Cys Ser Lys Glu Ser Asn Glu Glu Leu
                325                 330                 335

Thr Glu Ser Cys Glu Thr Lys Lys Leu Gly Gln Ser Leu Asp Cys Asn
            340                 345                 350

Ala Glu Val Tyr Val Val Pro Trp Glu Lys Lys Ile Tyr Pro Thr Val
        355                 360                 365

Asn Cys Gln Pro Leu Gly Met Ile Ser Leu Met Lys Arg Pro Pro Gly
    370                 375                 380

Phe Ser Pro Phe Arg Ser Ser Arg Ile Gly Glu Ile Lys Glu Glu Thr
385                 390                 395                 400

```
Thr Val Ser Pro Pro His Thr Ser Met Ala Pro Gln Asp Glu Glu
            405                 410                 415

Arg Asp Ser Gly Lys Glu Gln Gly His Thr Arg Arg His Asp Trp Gly
        420                 425                 430

His Glu Lys Gln Arg Lys His Asn Leu Gly His Gly His Lys His Glu
        435                 440                 445

Arg Asp Gln Gly His Gly His Gln Arg Gly His Gly Leu Gly His Gly
        450                 455                 460

His Glu Gln Gln His Gly Leu Gly His Gly His Lys Phe Lys Leu Asp
465                 470                 475                 480

Asp Asp Leu Glu His Gln Gly Gly His Val Leu Asp His Gly His Lys
                485                 490                 495

His Lys His Gly His Gly His Gly Lys His Lys Asn Lys Gly Lys Lys
                500                 505                 510

Asn Gly Lys His Asn Gly Trp Lys Thr Glu His Leu Ala Ser Ser Ser
                515                 520                 525

Glu Asp Ser Thr Thr Pro Ser Ala Gln Thr Gln Glu Lys Thr Glu Gly
        530                 535                 540

Pro Thr Pro Ile Pro Ser Leu Ala Lys Pro Gly Val Thr Val Thr Phe
545                 550                 555                 560

Ser Asp Phe Gln Asp Ser Asp Leu Ile Ala Thr Met Met Pro Pro Ile
                565                 570                 575

Ser Pro Ala Pro Ile Gln Ser Asp Asp Trp Ile Pro Asp Ile Gln
                580                 585                 590

Ile Asp Pro Asn Gly Leu Ser Phe Asn Pro Ile Ser Asp Phe Pro Asp
                595                 600                 605

Thr Thr Ser Pro Lys Cys Pro Gly Arg Pro Trp Lys Ser Val Ser Glu
        610                 615                 620

Ile Asn Pro Thr Thr Gln Met Lys Glu Ser Tyr Tyr Phe Asp Leu Thr
625                 630                 635                 640

Asp Gly Leu Ser

<210> SEQ ID NO 6
<211> LENGTH: 362
<212> TYPE: PRT
<213> ORGANISM: Artificial Sequence
<220> FEATURE:
<223> OTHER INFORMATION: Synthetic Polypeptide

<400> SEQUENCE: 6

Gln Glu Ser Gln Ser Glu Glu Ile Asp Cys Asn Asp Lys Asp Leu Phe
1               5                   10                  15

Lys Ala Val Asp Ala Ala Leu Lys Lys Tyr Asn Ser Gln Asn Gln Ser
            20                  25                  30

Asn Asn Gln Phe Val Leu Tyr Arg Ile Thr Glu Ala Thr Lys Thr Val
        35                  40                  45

Gly Ser Asp Thr Phe Tyr Ser Phe Lys Tyr Glu Ile Lys Glu Gly Asp
    50                  55                  60

Cys Pro Val Gln Ser Gly Lys Thr Trp Gln Asp Cys Glu Tyr Lys Asp
65                  70                  75                  80

Ala Ala Lys Ala Ala Thr Gly Glu Cys Thr Ala Thr Val Gly Lys Arg
                85                  90                  95

Ser Ser Thr Lys Phe Ser Val Ala Thr Gln Thr Cys Gln Ile Thr Pro
            100                 105                 110

Ala Glu Gly Pro Val Val Thr Ala Gln Tyr Asp Cys Leu Gly Cys Val
```

```
            115                 120                 125
His Pro Ile Ser Thr Gln Ser Pro Asp Leu Glu Pro Ile Leu Arg His
    130                 135                 140

Gly Ile Gln Tyr Phe Asn Asn Thr Gln His Ser Ser Leu Phe Met
145                 150                 155                 160

Leu Asn Glu Val Lys Arg Ala Gln Arg Gln Val Val Ala Gly Leu Asn
                165                 170                 175

Phe Arg Ile Thr Tyr Ser Ile Val Gln Thr Asn Cys Ser Lys Glu Asn
                180                 185                 190

Phe Leu Phe Leu Thr Pro Asp Cys Lys Ser Leu Trp Asn Gly Asp Thr
            195                 200                 205

Gly Glu Cys Thr Asp Asn Ala Tyr Ile Asp Ile Gln Leu Arg Ile Ala
    210                 215                 220

Ser Phe Ser Gln Asn Cys Asp Ile Tyr Pro Gly Lys Asp Phe Val Gln
225                 230                 235                 240

Pro Pro Thr Lys Ile Cys Val Gly Cys Pro Arg Asp Ile Pro Thr Asn
                245                 250                 255

Ser Pro Glu Leu Glu Glu Thr Leu Thr His Thr Ile Thr Lys Leu Asn
                260                 265                 270

Ala Glu Asn Asn Ala Thr Phe Tyr Phe Lys Ile Asp Asn Val Lys Lys
            275                 280                 285

Ala Arg Val Gln Val Val Ala Gly Lys Lys Tyr Phe Ile Asp Phe Val
    290                 295                 300

Ala Arg Glu Thr Thr Cys Ser Lys Glu Ser Asn Glu Glu Leu Thr Glu
305                 310                 315                 320

Ser Cys Glu Thr Lys Lys Leu Gly Gln Ser Leu Asp Cys Asn Ala Glu
                325                 330                 335

Val Tyr Val Val Pro Trp Glu Lys Lys Ile Tyr Pro Thr Val Asn Cys
                340                 345                 350

Gln Pro Leu Gly Met Ile Ser Leu Met Lys
            355                 360

<210> SEQ ID NO 7
<211> LENGTH: 255
<212> TYPE: PRT
<213> ORGANISM: Artificial Sequence
<220> FEATURE:
<223> OTHER INFORMATION: Synthetic Polypeptide

<400> SEQUENCE: 7

Ser Ser Arg Ile Gly Glu Ile Lys Glu Glu Thr Thr Val Ser Pro Pro
1               5                   10                  15

His Thr Ser Met Ala Pro Ala Gln Asp Glu Glu Arg Asp Ser Gly Lys
                20                  25                  30

Glu Gln Gly His Thr Arg Arg His Asp Trp Gly His Glu Lys Gln Arg
            35                  40                  45

Lys His Asn Leu Gly His Gly His Lys His Glu Arg Asp Gln Gly His
        50                  55                  60

Gly His Gln Arg Gly His Gly Leu Gly His Gly His Glu Gln Gln His
65                  70                  75                  80

Gly Leu Gly His Gly His Lys Phe Lys Leu Asp Asp Asp Leu Glu His
                85                  90                  95

Gln Gly Gly His Val Leu Asp His Gly His Lys His Lys His Gly His
            100                 105                 110

Gly His Gly Lys His Lys Asn Lys Gly Lys Lys Asn Gly Lys His Asn
```

```
                115                 120                 125
Gly Trp Lys Thr Glu His Leu Ala Ser Ser Ser Glu Asp Ser Thr Thr
    130                 135                 140

Pro Ser Ala Gln Thr Gln Glu Lys Thr Glu Gly Pro Thr Pro Ile Pro
145                 150                 155                 160

Ser Leu Ala Lys Pro Gly Val Thr Val Thr Phe Ser Asp Phe Gln Asp
                165                 170                 175

Ser Asp Leu Ile Ala Thr Met Met Pro Pro Ile Ser Pro Ala Pro Ile
                180                 185                 190

Gln Ser Asp Asp Asp Trp Ile Pro Asp Ile Gln Ile Asp Pro Asn Gly
            195                 200                 205

Leu Ser Phe Asn Pro Ile Ser Asp Phe Pro Asp Thr Thr Ser Pro Lys
    210                 215                 220

Cys Pro Gly Arg Pro Trp Lys Ser Val Ser Glu Ile Asn Pro Thr Thr
225                 230                 235                 240

Gln Met Lys Glu Ser Tyr Tyr Phe Asp Leu Thr Asp Gly Leu Ser
                245                 250                 255
```

ASSAYS FOR DETERMINING PLASMA KALLIKREIN SYSTEM BIOMARKERS

CROSS-REFERENCE TO RELATED APPLICATIONS

This application is a national stage filing under 35 U.S.C. § 371 of international PCT application PCT/US2014/061247, filed Oct. 17, 2014, which claims priority to U.S. Provisional Application No. 61/893,505, filed on Oct. 21, 2013, and to U.S. Provisional Application No. 61/893,837, filed on Feb. 14, 2014, the entire contents of each of which are incorporated by reference herein.

BACKGROUND

Plasma kallikrein (pKal) is the primary bradykinin-generating enzyme in the circulation. The activation of pKal occurs via the contact system which has been linked to disease pathology associated with hereditary angioedema (HAE). Bradykinin is a key mediator of pain, inflammation, edema and angiogenesis.

SUMMARY OF THE PRESENT DISCLOSURE

Plasma kallikrein (pKal) is a serine protease component of the contact system and is the primary bradykinin-generating enzyme in the circulation. The contact system is activated by either factor XIIa upon exposure to foreign or negatively charged surfaces or on endothelial cell surfaces by prolylcarboxypeptidases (Sainz I. M. et al., Thromb Haemost 98, 77-83, 2007). Activation of the plasma kallikrein amplifies intrinsic coagulation via its feedback activation of factor XII and enhances inflammation via the production of the proinflammatory nonapeptide bradykinin. As the primary kininogenase in the circulation, plasma kallikrein is largely responsible for the generation of bradykinin in the vasculature. A genetic deficiency in the C1-inhibitor protein (C1-INH), the major natural inhibitor of plasma kallikrein, leads to hereditary angioedema (HAE). Patients with HAE suffer from acute attacks of painful edema often precipitated by unknown triggers (Zuraw B. L. et al., N Engl J Med 359, 1027-1036, 2008). Through the use of pharmacological agents or genetic studies in animal models, the plasma kallikrein-kinin system (plasma KKS) has been implicated in various diseases.

The present disclosure is based on the development of a number of biomarker assays, including the HMWK ex vivo activation assay, the endogenous cleaved HMWK assay, and the pKal ex vivo activation assay as described herein. Such assays can be used to measure the activation level of the plasma kallikrein (pKal) system in the plasma of a subject. They also can be used to evaluate a candidate compound for its activity in modulating (inhibiting or activating) the pKal system.

In one aspect, the present disclosure features an ex vivo activation method, comprising: (i) incubating a plasma sample obtained from a subject with an activator of the plasma kallikrein (pKal) system (e.g., FXIIa); (ii) measuring the levels of intact high molecular weight kininogen (HMWK), the cleaved HMWK, or both, in the plasma sample before and after the incubation; and (iii) determining the reduction of intact HMWK in the sample after the activation. Optionally, the plasma sample and the activator are incubated in the presence of a pKal modulator candidate (e.g., an inhibitor candidate such as DX2930 or an activator candidate). The method can further comprise assessing the activity of the pKal modulator candidate. In some embodiments, the levels of intact HMWK and cleaved HMWK are measured by Western blot analysis, such as Protein Simple Western blot analysis.

In another aspect, the present disclosure features a method for assessing plasma activation in a subject, comprising: providing a plasma sample from a subject; and measuring the level of cleaved HMWK in the plasma sample. The level of cleaved HMWK can be measured by, e.g., Western blot such as Protein Simple Western blot analysis. In some embodiments, the subject has or is suspected of having a disease associated with the pKal system. Alternatively or in addition, the subject is treated with a pKal inhibitor. Any of the methods described herein can further comprise evaluating the efficacy of the pKal inhibitor, wherein a reduced level of cleaved HMWK after the treatment as compared with that before the treatment indicates that the pKal inhibitor is effective.

In yet another aspect, the present disclosure provides an ex vivo assay for determining pKal activity in a sample (e.g., a plasma sample from a subject), comprising: (i) incubating the sample with a pKal system activator (e.g., Factor XIIa or FXIIa) in the presence of a pKal substrate, and (ii) measuring the activity of pKal based on the cleavage rate of the substrate. In some examples, the substrate attached to a label which is capable of releasing a detectable signal after being cleaved by pKal and the cleavage rate of the substrate is determined based on the magnitude of the detectable signal. In some examples, the plasma sample is incubated with the activator, the pKal substrate, and a pKal modulator candidate (e.g., an inhibitor modulator or an activator modulator). The method can further comprise evaluating the activity of the pKal modulator candidate (e.g., DX-2930), wherein a change of the level of pKal activity in the presence of the pKal modulator candidate as related to the level of pKal activity in the absence of the pKal inhibitor candidate indicates that the inhibitor candidate is effective. For example, a reduced level of pKal activity indicates that the pKal modulator candidate is a pKal inhibitor; while an elevated level of pKal activity indicates that the pKal modulator candidate is a pKal activator. Any of the assay method described herein can be performed in a microplate.

In any of the assay methods described herein, the method may further comprise assessing whether the subject has or is at risk for a disease associated with pKal (e.g., HAE); wherein an elevated level of the cleaved HMWK as compared to a predetermined value indicates that the subject has or is at risk for the disease. In some embodiments, the subject may be a human patient having a disease associated with pKal (e.g., HAE) and is subjected to a treatment of the disease (e.g., a pKal inhibitor such as DX2930). The plasma sample can be obtained after or during the course of the treatment. In some embodiments, the method further comprises evaluating the efficacy of the treatment; wherein a reduced level of cleaved HMWK as to compared that before the treatment (e.g., a pKal inhibitor such as DX2930) or a reduced level of cleaved HMWK over the course of the treatment (e.g., a pKal inhibitor such as DX2930) indicates that the treatment is effective.

Further, the present disclosure provides methods of evaluating a subject, e.g., a subject at risk for or suffering from a pKal-mediated or bradykinin-mediated disorder, which may involve any of the assay methods described herein. Provided methods permit analysis of patients with plasma kallikrein-mediated angioedema (KMA), or other diseases mediated by pKal useful in the evaluation and treatment.

Embodiments of the present disclosure provide a biomarker and use thereof in the identification and treatment of patients, e.g., patients suffering from edema caused by bradykinin that is generated by plasma kallikrein. Methods, compositions and devices disclosed herein are useful in a number of ways. For example, levels of a pKal marker can be used to identify disorders associated with elevated contact system activation. Initial screening can be followed up with in vitro or in vivo testing with plasma kallikrein inhibitors (e.g., DX-88, EPIKAL2, or DX-2930), e.g., in preclinical models of disease. A marker disclosed herein can also be used as a pharmacodynamic biomarker or to otherwise monitor the response of a subject to a kallikrein inhibitor. A marker disclosed herein can be used in a companion diagnostic to enable treatment of diseases mediated by plasma kallikrein, manage dosing during prophylactic therapy of a pKal-mediated or bradykinin-mediated disorder, e.g., HAE, non-histamine-dependent idiopathic angioedema, rheumatoid arthritis, Crohn's disease, lupus, Alzheimer's disease, septic shock, burn injury, brain ischemia/reperfusion injury, cerebral edema, diabetic retinopathy, diabetic nephropathy, macular edema, vasculitis, arterial or venous thrombosis, thrombosis associated with ventricular assist devices or stents, heparin-induced thrombocytopenia with thrombosis, thromboembolic disease, and coronary heart disease with unstable angina pectoris, edema, eye disease, gout, intestinal bowel disease, oral mucositis, neuropathic pain, inflammatory pain, spinal stenosis-degenerative spine disease, post operative ileus, aortic aneurysm, osteoarthritis, hereditary angioedema, pulmonary embolism, stroke, head trauma or peri-tumor brain edema, sepsis, acute middle cerebral artery (MCA) ischemic event (stroke), restenosis (e.g., after angioplasty), systemic lupus erythematosis nephritis, an autoimmune disease, an inflammatory disease, a cardiovascular disease, a neurological disease, a disease associated with protein misfolding, a disease associated with angiogenesis, hypertensive nephropathy and diabetic nephropathy, allergic and respiratory diseases (e.g. anaphylaxis, asthma, chronic obstructive pulmonary disease, acute respiratory distress syndrome, cystic fibrosis, persistent, rhinitis) and tissue injuries (e.g. burn or chemical injury).

In one aspect, the present present disclosure provides a method of evaluating or treating a subject, e.g., distinguishing a pKal-mediated disorder, such as a bradykinin-mediated angioedema, from a histamine-mediated disorder, or predicting a future attack of a pKal-mediated disorder, comprising acquiring, e.g., determining, the level of one or more marker correlated with pKal activation (a pKal marker), disclosed herein, e.g., prekallikrein, active pKal, alpha 2M-pKal, C1-INH-pKal, intact kininogen, and cleaved kininogen, thereby evaluating or treating said subject. In some embodiments, the method comprises acquiring, e.g., detecting, the level of one or more marker correlated with a histamine-mediated inflammatory response (a H-marker), e.g., tryptase.

In some embodiments, said pKal-mediated disorder is HAE, IAE, IBD, or IBS. In some embodiments, said pKal-mediated disorder is selected from non-histamine-dependent idiopathic angioedema, rheumatoid arthritis, Crohn's disease, lupus, Alzheimer's disease, septic shock, burn injury, brain ischemia/reperfusion injury, cerebral edema, diabetic retinopathy, diabetic nephropathy, macular edema, vasculitis, arterial or venous thrombosis, thrombosis associated with ventricular assist devices or stents, heparin-induced thrombocytopenia with thrombosis, thromboembolic disease, and coronary heart disease with unstable angina pectoris, edema, eye disease, gout, intestinal bowel disease, oral mucositis, neuropathic pain, inflammatory pain, spinal stenosis-degenerative spine disease, post operative ileus, aortic aneurysm, osteoarthritis, hereditary angioedema, pulmonary embolism, stroke, head trauma or peri-tumor brain edema, sepsis, acute middle cerebral artery (MCA) ischemic event (stroke), restenosis (e.g., after angioplasty), systemic lupus erythematosis nephritis, an autoimmune disease, an inflammatory disease, a cardiovascular disease, a neurological disease, a disease associated with protein misfolding, a disease associated with angiogenesis, hypertensive nephropathy and diabetic nephropathy, allergic and respiratory diseases (e.g. anaphylaxis, asthma, chronic obstructive pulmonary disease, acute respiratory distress syndrome, cystic fibrosis, persistent, rhinitis) and tissue injuries (e.g., burn or chemical injury).

In another aspect, the present present disclosure provides a method of evaluating or treating a subject, said subject having a symptom consistent with both a pKal-mediated disorder, e.g., bradykinin-mediated angioedema, and a histamine related disorder, comprising a) optionally, determining that said subject has a symptom, e.g., edema or abdominal discomfort, consistent with one or both a pKal-mediated disorder and a histamine related disorder; b) if said subject has not been treated with an anti-histamine therapy for said symptom, then treating said subject with an anti-histamine therapy; c) acquiring, e.g., detecting, the level of one or more marker correlated with pKal activation (a pKal marker), e.g., of prekallikrein, active pKal, alpha 2M-pKal, C1-INH-pKal, intact kininogen, and cleaved kininogen; d) if said level meets a predetermined criterion, e.g., if it is at or above a reference level: selecting the subject for kallikrein inhibitor therapy; or administering a kallikrein inhibitor to said subject, thereby evaluating or treating said subject. In some embodiments, the method comprises selecting the subject for kallikrein inhibitor therapy. In certain embodiments, the method comprises administering a kallikrein inhibitor to said subject. In particular embodiments, the selecting the subject for kallikrein inhibitor therapy; or administering a kallikrein inhibitor to said subject, occurs prior to a determination that the subject has shown an acceptable response to said anti-histamine therapy, e.g., occurs within 1, 2, 3, 4, 5, 6, 7, 8, 9, or 10 hours of said treatment with an anti-histamine therapy. In some embodiments, a determination that said subject has a symptom consistent with both a pKal-mediated disorder and a histamine related disorder and acquisition of a sample from said patient for determining the level of a pKal marker occur: within 30 minutes, 1, 2 or 3 hours of one another; or in the same visit to a healthcare provider.

In some embodiments, the said pKal inhibitor is selected from DX-88, DX-2930, or EpiKal-2.

In some embodiments, the method comprises acquiring, e.g., determining, the level of one or more marker correlated with a histamine-mediated inflammatory response (a H-marker). In certain embodiments, said subject is evaluated for susceptibility to a pKal-mediated disorder. In certain embodiments, said subject has a symptom of, e.g., consistent with, a pKal-mediated disorder, e.g., edema, e.g., HAE. In certain embodiments, said subject has a symptom of a disorder characterized by unwanted pKal activation and said subject has been administered an anti-histamine therapy. In particular embodiments, said anti-histamine therapy is administered within 1, 2, 3, 4, 5, 6, 7, 8, 9, or 10 hours before or after a determining step as disclosed herein. In particular embodiments, the method further comprises administering an anti-histamine therapy to said subject, e.g., before, after, or during the evaluation or determinations as disclosed herein.

In some embodiments, responsive to said determination or evaluation, administering a kallikrein inhibitor to said subject. In certain embodiments, said subject has one or more or all of the following symptoms or properties: recurrent attacks of swelling; swelling wherein said swelling is completely or predominantly peripheral, e.g., the subject has no significant abdominal or airway swelling; hives; redness, pain, and swelling in the absence of evidence of infection; fails to respond to antihistamine or corticosteroid therapy; or has non-histamine-mediated edema. In certain embodiments, said subject has persistent or recurring edema and is non-responsive to one or both of anti-histamine and steroid therapy. In certain embodiments, the subject has a no history of a pKal-mediated disorder, e.g., HAE, IAE, IBD, or IBS; the subject has a history of a pKal-mediated disorder, e.g., HAE, IAE, IBD, or IBS, the subject has no history of HAE; the subject has a history of HAE; the subject has no history of IAE; the subject has a history of IAE; the subject has no history of IBD or IBS; the subject has a history of IBD or IBS; the subject has a no history of a histamine mediated disorder, e.g., a food allergy; the subject has a history of a histamine mediated disorder, e.g., a food allergy; the subject has a no history of a pKal-mediated disorder, e.g., HAE, IAE, IBD, or IBS, and has no history of a histamine-mediated disorder, e.g., a food allergy; or the subject has no history of a pKal-mediated disorder, e.g., HAE, IAE, IBD, or IBS, and has a history of a histamine-mediated disorder, e.g., a food allergy: the subject has a history of a pKal-mediated disorder, e.g., HAE, IAE, IBD, or IBS, and has no history of a histamine-mediated disorder, a food allergy; or the subject has a history of a pKal-mediated disorder, e.g., HAE, IAE, IBD, or IBS, and has a history of a histamine-mediated disorder, e.g., a food allergy.

In some embodiments, the subject has been treated with a kallikrein inhibitor, e.g., in prophylactic therapy, e.g., for HAE, and the subjects response to the kallikrein inhibitor is evaluated or monitored, and optionally, responsive to said monitoring, a therapy is selected or administered, e.g., responsive to the determination, the dosage of the kallikrein inhibitor is adjusted. In some embodiments, a determination of a pKal marker is performed in the context of a companion diagnostic, and optionally, administration of a therapeutic is given or withheld on the basis of the determination. In certain embodiments, responsive to said acquisition, identifying an impending acute attack, e.g. an HAE or IEA attack. In particular embodiments, said subject is evaluated for susceptibility to idiopathic angioedema. In particular embodiments, said evaluation comprises determining if said subject is suffering from a pKal-mediated disorder, e.g., a bradykinin-mediated disorder, e.g., a pKal-mediated angioedema, or from a histamine-mediated disorder, e.g., an allergic food reaction.

In some embodiments, the subject has no history of a pKal-mediated disorder, e.g., HAE or IAE. In some embodiments, the subject has a history of a pKal-mediated disorder, e.g., HAE or IAE. In some embodiments, the subject has a no history of a pKal-mediated disorder, e.g., HAE, IAE, IBD or IBS; the subject has a history of a pKal-mediated disorder, e.g., HAE, IAE, IBD, or IBS, the subject has no history of HAE; the subject has a history of HAE; the subject has no history of IAE; the subject has a history of IAE; the subject has no history of IBD or IBS; the subject has a history of IBD or IBS; the subject has a no history of a histamine mediated disorder, e.g., a food allergy; the subject has a history of a histamine mediated disorder, e.g., a food allergy; the subject has a no history of a pKal-mediated disorder, e.g., HAE, IAE, IBD, or IBS, and has no history of a histamine-mediated disorder, e.g., a food allergy; or the subject has no history of a pKal-mediated disorder, e.g., HAE, IAE, IBD, or IBS, and has a history of a histamine-mediated disorder, e.g., a food allergy: the subject has a history of a pKal-mediated disorder, e.g., HAE, IAE, IBD, or IBS, and has no history of a histamine-mediated disorder, a food allergy; or the subject has a history of a pKal-mediated disorder, e.g., HAE, IAE, IBD, or IBS, and has a history of a histamine-mediated disorder, e.g., a food allergy.

In some embodiments, a pkal marker, e.g., a pKal marker disclosed herein, is detected with an antibody-based reagent. In certain embodiments, a pKal marker is detected with sandwich immune-assay. In certain embodiments, the method comprises acquiring, e.g., detecting, the level of alpha 2M-pKal and C1-INH-pKal, e.g., by sandwich immune assays. In certain embodiments, the method comprises acquiring, e.g., detecting, the level kininogen, e.g., one or both of intact or cleaved kininogen, e.g., by an electrophoretic separation assay, e.g., a Western blot. In some embodiments, a pKal marker, e.g., kininogen, is detected in an assay which relies on separation, e.g., electrophoretic separation, e.g., by Western blot, of the analyte from other products. In some embodiments, a pKal marker is detected with a Simple Western™ assay. Simple Western™ assays are known in the art (see, e.g., Rustandi et al. Qualitative and quantitative evaluation of Simon™, a new CE-based automated Western blot system as applied to vaccine development. Electrophoresis. 2012 September; 33(17):2790-7). Simple Western™ products are also available commercially (see, e.g., ProteinSimple, Santa Clara, Calif.).

In some embodiments, a first pKal marker, e.g., of prekallikrein, active preKal, alpha 2M-pKal, or C1INH-pKal, is detected with sandwich immune-assay and a second pKal marker, e.g., kininogen, is detected in an assay which relies on separation, e.g., electrophoretic separation, e.g., by Western blot or Simple Western™, of the analyte from other products. In certain embodiments, detection of a pKal marker is qualitative. In certain embodiments, detection of a pKal marker is quantitative. In particular embodiments, the method comprises determining the levels of C1-INH-pKal and α2M-pKal. In particular embodiments, the method comprises determining the levels of active pKal. In particular embodiments, levels of prekallikrein, active pKal, alpha 2M-pKal, C1-INH-pKal, intact kininogen, and cleaved kininogen is each detected.

In some embodiments, the method comprises comparing the level of a pKal marker, e.g., of prekallikrein, active pKal, alpha 2M-pKal, C1-INH-pKal, intact kininogen, or cleaved kininogen, with a reference value. In certain embodiments, said reference value is a function of the level of said pKal marker in an HAE, e.g., in one or more HAE subjects. In certain embodiments, said reference value is a function of the level of said pKal marker in an HAE during an attack, e.g., in one or more HAE subjects during an acute attack. In certain embodiments, said reference value is a function of the level of a pKal marker in an IAE, e.g., in one or more IAE subjects. In certain embodiments, said reference value is a function of the level of a pKal marker in an IAE during an acute attack, e.g., in one or more IAE subjects during an acute attack. In certain embodiments, said reference value is a function of the level of a pKal marker in the absence of HAE or IAE, e.g., in one or more subjects having no history of HAE or IAE.

In particular embodiments, the method comprises e.g., responsive to a comparison, classifying the subject, e.g., classifying the subject for risk for a pKal-mediated disorder, or administering or withholding a therapy from said subject. In certain embodiments, the method comprises, e.g., responsive to a comparison, selecting a treatment for said subject. In some embodiment, the method comprises, e.g., responsive to a comparison, administering or withholding a therapy from said subject, e.g., a kallikrein binding agent; a bradykinin B2 receptor antagonist; or a C1-INH replacement agent. In particular embodiments, said treatment is the administration of a pKal inhibitor, e.g., a pKal inhibitor selected from DX-88; EpiKal-2, and DX-2930.

In some embodiments, a sample from said subject is contacted with a substrate comprising a capture agent for two or more of the following markers disclosed herein, e.g., from: prekallikrein, e.g., an anti-prekallikrein antibody; active pKal, e.g., an anti-active pKal antibody; alpha 2M-pKal, e.g., an anti-alpha 2M-pKal antibody; C1INH-pKal, e.g., an anti-C1INH-pKal antibody; or a H marker, e.g., an anti-H marker antibody; optionally, wherein at least one capture agent is a capture agent for a pKal marker.

In some embodiments, the method comprises acquiring a sample, e.g., a blood or plasma sample from said subject.

In some embodiments, said substrate comprises: a capture agent for C1-INH-pKal; and a capture agent for alpha2M-pKal. In certain embodiments, said substrate further comprises one or both of: a capture agent for prekallikrein, e.g., an anti-prekallikrein antibody; a capture agent for active pKal, e.g., an anti-active pKal antibody.

In some embodiments, a first capture agent (for a first marker) and a second capture agent (for a second marker) are disposed on a substrate such that a signal for the presence of the first marker can be distinguished from a signal for the presence of the second marker. In certain embodiments, said first capture agent (for a first marker) is located at a first location or address and said second capture agent (for a second marker) is located at a second location or address. In particular embodiments, said first location or address and said second location or address do not overlap on said substrate. In certain embodiments, said first capture agent is for a first pKal marker. In certain embodiments, said first capture agent is for a first pKal marker and said second capture agent is for a second pKal marker. In certain embodiments, said first capture agent is for a pKal marker and said second capture agent is for an H-marker. In certain embodiments, said first marker is 2M-pKal and said second marker is C1INH-pKal. In certain embodiments, the capture agent for 2M-pKal is an anti-2M-pKal antibody and the capture agent for C1INH-pKal is an anti-C1INH-pKal antibody.

In certain embodiments, the method comprises contacting a substrate with a detectable, e.g., labeled, anti-2M-pKal antibody and a detectable, e.g., labeled, anti-C1INH-pKal antibody, to determine the presence or amount of a pKal marker. In certain embodiments, said antibodies are labeled with a moiety that produces a colored product, emits a photon, absorbs a photon, alters a substrate, or alters the conductivity of the substrate. In certain embodiments, said antibodies are labeled with a moiety that utilizes electrochemiluminescence. In certain embodiments, said antibodies are labeled with resinium. In particular embodiments, said substrate in provided in a meso scale discovery device. In particular embodiments, said substrate in provided as a dip-stick device, suitable for use with one or both of blood and plasma. In particular embodiments, said first capture agent and said second capture agent are disposed in a common or fluidically connected chamber, e.g., a chamber, e.g., a well or depression, in a multi chamber device, e.g., a multi-well plate. In particular embodiments, said first capture agent and said second capture agent are printed onto a substrate.

In some embodiments, said capture agent for a first pKal marker is at a first location on said substrate and said capture agent for a second pKal marker is at a second location on said substrate, and said first and second locations are disposed on said substrate such that a signal for the presence of the first pKal marker can be distinguished from a signal from a second pKal marker. In certain embodiments, said substrate comprises a capture agent for a third marker at a third location, and the third location is disposed on said substrate such that a signal for the presence of the third marker can be distinguished from a signal from said first and second marker. In particular embodiments, said first capture agent is specific for alpha 2M-pKal or C1INH-pKal. In particular embodiments, said first capture agent is specific for alpha 2M-pKal and said second capture agent is specific for C1INH-pKal.

In some embodiments, a determination of the level of a pKal marker in a sample can be made within 1, 2, 3, 4, or 5 hours of contact of the substrate with said sample. In some embodiments, a determination of the level of two pKal markers in a sample can be made within 1, 2, 3, 4, or 5 hours of contact of the substrate with said sample. In some embodiments, a determination of the level of two pKal markers can be made in simultaneously performed assays, e.g., the incubation or other intervals for the tests overlap with one another.

In another aspect, the present present disclosure provides a substrate comprising capture agents for a plurality of pKal markers, e.g., as described herein.

In a further aspect, the present present disclosure provides a method of determining if a disorder is susceptible to treatment with a pKal inhibitor comprising: evaluating the levels of one or more of pKal markers, e.g., as described herein, in e.g., a subject suffering from said disorder, or an animal model for said disorder; comparing the determined level with a reference, wherein a level that meets a predetermined criterion, e.g., if it is at or above a reference level, is indicative of a disorder susceptible to treatment with a pKal inhibitor. In some embodiments, the method comprises evaluating the effect of a kallikrein inhibitor, in vitro or in vivo, or in an animal model of said disorder.

In another aspect, the present present disclosure provides a method of treating subject having a pKal mediated disorder, e.g., a bradykinin mediated disorder, comprising evaluating the level of a pKal marker described herein, e.g., by a method described herein, determining, and responsive to said evaluating, selecting a treatment, e.g., selecting one or both of a dosage amount or dosing frequency, of a kallikrein inhibitor. In some embodiments, the method comprises administering a kallikrein inhibitor to said subject. In some embodiments, said patient has been administered a kallikrein inhibitor prior to said evaluation. In certain embodiments, the method comprises administering a kallikrein inhibitor at said selected dosage or frequency.

In a further aspect, the present present disclosure provides a method of determining if a disorder is susceptible to treatment with a pKal inhibitor comprising: evaluating the levels one or a plurality of pKal markers, e.g., as described herein, in e.g., a subject suffering from said disorder, or an animal model for said disorder; comparing the determined level with a reference, wherein a level that meets a predetermined criterion, e.g., if it is at or above a reference level, is indicative of a disorder susceptible to treatment with a pKal inhibitor. In some embodiments, the method comprises evaluating the effect of a kallikrein inhibitor, in vitro or in vivo, or in an animal model of said disorder.

In another aspect the present disclosure features, methods and devices for collection of a sample, e.g., blood, with minimum contact activation. In an embodiment, the present disclosure features a container, having disposed therein a capture reagent described herein, e.g., a kallikrein inhibitor, e.g., a polypeptide that is similar in sequence to DX-88, e.g., one that differs from DX-88 by no more than 1, 2, or 5 amino acid residues, e.g., EPIKAL-2. The container is configured, e.g., with an aperture, opening, septum, etc., so as to allow collection of a sample, e.g., blood, from a subject and binding of a pKal-related marker in the sample, e.g., pKal, with the capture reagent, in the same container. Measurement of bound species, e.g., pKal, can be carried out in the same container or in embodiments, the substrate is removed from the prior container to measurement, e.g., measurement can be in or on another device. In embodiments the volume of the container is 0.5-100, 0.5-50, 0.5-10, 1-100, 1-50, is 1-25 mls. In an embodiment the capture reagent, e.g., a pKal capture reagent, is disposed on the inner surface of the container. The capture reagent can be coupled to the surface with a first specific binding partner bound to the surface and a second specific binding partner coupled to the capture reagent. Examples of specific binding partners are biotin and avidin. In an embodiment biotinylated capture reagent, e.g., a pKal capture reagent, e.g., a kallikrein inhibitor, e.g., a polypeptide that is similar in sequence to DX-88, e.g., one that differs from DX-88 by no more than 1, 2, or 5 amino acid residues, e.g., Epikal-2 is disposed on a surface of the container that is coated with avidin.

The present disclosure provides biomarkers capable of identifying patients with plasma kallikrein-mediated angioedema (KMA), or other diseases mediated by pKal useful in the evaluation and treatment.

Patients shown to exhibit pKal activation via a biomarker are candidates for treatment with a pKal inhibitor, such as DX-88, a small protein inhibitor of pKal approved for the treatment of the acute edematous attacks associated HAE. Other pKal inhibitors include DX-2930, which is a fully human antibody inhibitor. In some embodiments, patients shown to exhibit pKal activation via a biomarker are candidates for treatment with a bradykinin B2 receptor antagonist, e.g., Incatibant (Firazyr®). In some embodiments, patients shown to exhibit pKal activation via a biomarker are candidates for treatment with a C1-INH replacement agent, e.g., a purified human pasteurized nanofiltered C1-INH concentrate (Berinert®).

Embodiments of the present disclosure provide a biomarker and use thereof in the identification and treatment of patients, e.g., patients suffering from edema caused by bradykinin that is generated by plasma kallikrein. Methods, compositions and devices disclosed herein are useful in a number of ways. For example, levels of a pKal marker can be used to identify disorders associated with elevated contact system activation. Initial screening can be followed up with in vitro or in vivo testing with plasma kallikrein inhibitors (e.g., DX-88, EPIKAL-2, or DX-2930), for example, in preclinical models of disease. A marker disclosed herein can also be used as a pharmacodynamic biomarker or to otherwise monitor the response of a subject to a kallikrein inhibitor. A marker disclosed herein can be used in a companion diagnostic to enable treatment of diseases mediated by plasma kallikrein, manage dosing during prophylactic therapy of HAE, or identify an impending acute HAE attack.

Other exemplary embodiments include:

A microplate-based pKal activity assay, comprising: (a) providing a plasma sample from a subject; (b) incubating the plasma sample with a pKal system activator in the presence of a pKal substrate, wherein the substrate is attached to a label which is capable of release a detectable signal after being cleaved by pKal; and (c) measuring the activity of pKal based on the density of the detectable signal. The activator can be Factor FXIIa. In some examples, the plasma sample can be incubated with the activator, the pKal substrate, and a pKal inhibitor candidate. In some examples, the method may further comprise evaluating the activity of the pKal inhibitor candidate, wherein a reduced level of pKal activity in the presence of the pKal inhibitor candidate as related to the level of pKal activity in the absence of the pKal inhibitor candidate indicates that the inhibitor candidate is effective.

The details of one or more embodiments of the present disclosure are set forth in the description below. Other features or advantages of the present present disclosure will be apparent from the following drawings and detailed description of several embodiments, and also from the appended claims.

BRIEF DESCRIPTION OF DRAWINGS

FIG. 12 is a schematic illustration of a microplate-based pKal activity assay, with accompanying experiment showing the inhibitory activity of DX-2930 on pKal activity in treated monkeys.

FIG. 17 illustrates an exemplary HMWK Ex Vivo activation assay for examining the inhibitory activity of an example pKal inhibitor Dx-2930, using both Protein Simple Western analysis and traditional Western blot analysis. The HMWK Ex Vivo Activation Assay described herein showed that minimal Levels of DX-2930 inhibited pKal activation, which outperformed endogenous C1 inhibitor alone in normal human plasma.

DETAILED DESCRIPTION

Figure 1:
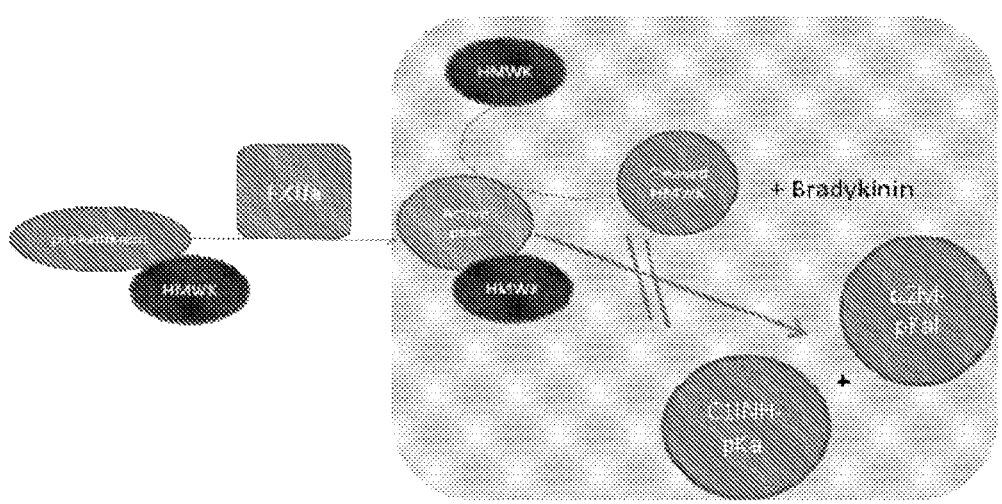
FIG. 1 is a depiction of elements involved in the contact system activation of plasma kallikrein. Cleaved HMWK can be determined by Western blot. α2M-pKal and C1INH-pKal can be determined by immunoassay (MSD platform).

Described herein are assays for measuring levels in a sample from a subject of biomarkers associated with the plasma kallikrein (pKal) system, such as intact high molecular weight kininogen (HMWK), cleaved HMWK, and/or pKal activity. In some embodiments, the assays comprise incubating a sample obtained from the subject with an activator of the pKal system and measuring the levels of intact high molecular weight kininogen (HMWK), cleaved HMWK, and/or pKal activity. Such assays are useful, e.g., for assessing whether the subject has or is at risk for a disease associated with pKal, for assessing treatment of a disease associated with pKal, and for identifying drug candidates, e.g., pKal modulators such as pKal inhibitors. Such assays are also useful, e.g., for selecting subjects for treatment, such as for treatment of a disease associated with pKal.

DEFINITIONS

For convenience, before further description of the present disclosure, certain terms employed in the specification, examples and appended claims are defined here. Other terms are defined as they appear in the specification.

The singular forms "a", "an", and "the" include plural references unless the context clearly dictates otherwise.

As used herein, "acquire" or "acquiring" refers to obtaining possession of a physical entity, or a value, e.g., a numerical value, by "directly acquiring" or "indirectly acquiring" the physical entity or the value. "Directly acquiring" means performing a process (e.g., performing an assay or test on a sample or "analyzing a sample" as that term is defined herein) to obtain the physical entity or value. "Indirectly acquiring" refers to receiving the physical entity or value from another party or source (e.g., a third party laboratory that directly acquired the physical entity or value). Directly acquiring a physical entity includes performing a process, e.g., analyzing a sample, that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent.

As used herein, "analyzing" a sample includes performing a process that involves a physical change in a sample or another substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Analyzing a sample can include performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent.

The term "agonist," as used herein, is meant to refer to an agent that mimics or up-regulates (e.g., potentiates or supplements) the bioactivity of a protein. An agonist can be a wild-type protein or derivative thereof having at least one bioactivity of the wild-type protein. An agonist can also be a compound which increases at least one bioactivity of a protein. An agonist can also be a compound which increases the interaction of a polypeptide with another molecule, e.g., a target peptide or nucleic acid.

The term "antagonist" as used herein is meant to refer to an agent that downregulates (e.g., suppresses or inhibits) at least one bioactivity of a protein. An antagonist can be a compound which inhibits or decreases the interaction between a protein and another molecule, e.g., a target peptide or enzyme substrate. An antagonist can also be a compound which reduces or inhibits the amount of expressed protein present. Typically, inhibiting a protein or a gene refers to reducing expression or a relevant activity of the protein or gene by at least 10% or more, for example, 20%, 30%, 40%, or 50%, 60%, 70%, 80%, 90% or more, or a decrease in expression or the relevant activity of greater than 1-fold, 2-fold, 3-fold, 4-fold, 5-fold, 10-fold, 50-fold, 100-fold or more as measured by one or more methods described herein or recognized in the art.

As used herein, "binding affinity" refers to the apparent association constant or $K_a$. The $K_a$ is the reciprocal of the dissociation constant ($K_d$). A binding protein may, for example, have a binding affinity of at least $10^5$, $10^6$, $10^7$, $10^8$, $10^9$, $10^{10}$ and $10^{11}$ $M^{-1}$ for a particular target molecule. Higher affinity binding of a binding protein to a first target relative to a second target can be indicated by a higher $K_a$ (or a smaller numerical value $K_d$) for binding the first target than the $K_a$ (or numerical value $K_d$) for binding the second target. In such cases, the binding protein has specificity for the first target (e.g., a protein in a first conformation or mimic thereof) relative to the second target (e.g., the same protein in a second conformation or mimic thereof; or a second protein). Differences in binding affinity (e.g., for specificity or other comparisons) can be at least 1.5, 2, 3, 4, 5, 10, 15, 20, 37.5, 50, 70, 80, 91, 100, 500, 1000, or $10^5$ fold.

Binding affinity can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in TRIS-buffer (50 mM TRIS, 150 mM NaCl, 5 mM $CaCl_2$ at pH7.5). These techniques can be used to measure the concentration of bound and free binding protein as a function of binding protein (or target) concentration. The concentration of bound binding protein ([Bound]) is related to the concentration of free binding protein ([Free]) and the concentration of binding sites for the binding protein on the target where (N) is the number of binding sites per target molecule by the following equation:

$$[Bound]=N\cdot[Free]/((1/Ka)+[Free]).$$

It is not always necessary to make an exact determination of $K_a$, though, since sometimes it is sufficient to obtain a quantitative measurement of affinity, e.g., determined using a method such as ELISA or FACS analysis, is proportional to $K_a$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

The term "binding protein" refers to a protein that can interact with a target molecule. This term is used interchangeably with "ligand." A "plasma kallikrein binding protein" refers to a protein that can interact with (e.g., bind) plasma kallikrein, and includes, in particular, proteins that preferentially or specifically interact with and/or inhibit plasma kallikrein. A protein inhibits plasma kallikrein if it causes a decrease in the activity of plasma kallikrein as compared to the activity of plasma kallikrein in the absence of the protein and under the same conditions. In some embodiments, the plasma kallikrein binding protein is an antibody.

The term "capture reagent" refers to a moiety that binds specifically to its ligand.

As used herein, the terms "complex" or "complex formation" refer to a complex between members having a specific affinity for one another.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Motif sequences for biopolymers can include positions which can be varied amino acids. For example, the symbol "X" in such a context generally refers to any amino acid (e.g., any of the twenty natural amino acids) unless otherwise specified, e.g., to refer to any non-cysteine amino acid. Other allowed amino acids can also be indicated for example, using parentheses and slashes. For example, "(A/W/F/N/Q)" means that alanine, tryptophan, phenylalanine, asparagine, and glutamine are allowed at that particular position.

As used herein, a "detection reagent" refers to a moiety that binds to the moiety to be detected. Typically it generates a signal, e.g., fluorescence, or produces of a measurable compound.

An "epitope" refers to the site on a target compound that is bound by a binding protein (e.g., an antibody such as a Fab or full length antibody). In the case where the target compound is a protein, the site can be entirely composed of amino acid components, entirely composed of chemical modifications of amino acids of the protein (e.g., glycosyl moieties), or composed of combinations thereof. Overlapping epitopes include at least one common amino acid residue, glycosyl group, phosphate group, sulfate group, or other molecular feature.

A first binding protein (e.g., antibody) "binds to the same epitope" as a second binding protein (e.g., antibody) if the first binding protein binds to the same site on a target compound that the second binding protein binds, or binds to a site that overlaps (e.g., 50%, 60%, 70%, 80%, 90%, or 100% overlap, e.g., in terms of amino acid sequence or other molecular feature (e.g., glycosyl group, phosphate group, or sulfate group)) with the site that the second binding protein binds.

A first binding protein (e.g., antibody) "competes for binding" with a second binding protein (e.g., antibody) if the binding of the first binding protein to its epitope decreases (e.g., by 10%, 20%, 30%, 40%, 50%, 60%, 70%, 80%, 90%, 100%, or more) the amount of the second binding protein that binds to its epitope. The competition can be direct (e.g., the first binding protein binds to an epitope that is the same as, or overlaps with, the epitope bound by the second binding protein), or indirect (e.g., the binding of the first binding protein to its epitope causes a steric change in the target compound that decreases the ability of the second binding protein to bind to its epitope).

As used herein, a "functional" biological molecule is a biological molecule in a form in which it exhibits a property and/or activity by which it is characterized.

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

In a preferred embodiment, the length of a reference sequence aligned for comparison purposes is at least 30%, preferably at least 40%, more preferably at least 50%, even more preferably at least 60%, and even more preferably at least 70%, 80%, 90%, 92%, 95%, 97%, 98%, or 100% of the length of the reference sequence. For example, the reference sequence may be the length of the immunoglobulin variable domain sequence.

As used herein, the term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1-6.3.6. Aqueous and nonaqueous methods are described in that reference and either can be used. Specific hybridization conditions referred to herein are as follows: (1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions in 6×SSC at about 45° C., followed by one or more washes in 0.2×SSC, 0.1% SDS at 60° C.; (3) high stringency hybridization conditions in 6×SSC at about 45° C., followed by one or more washes in 0.2×SSC, 0.1% SDS at 65° C.; and (4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified. The disclosure includes nucleic acids that hybridize with low, medium, high, or very high stringency to a nucleic acid described herein or to a complement thereof, e.g., nucleic acids encoding a binding protein described herein. The nucleic acids can be the same length or within 30, 20, or 10% of the length of the reference nucleic acid. The nucleic acid can correspond to a region encoding an immunoglobulin variable domain sequence described herein.

An "isolated composition" refers to a composition that is removed from at least 90% of at least one component of a natural sample from which the isolated composition can be obtained. Compositions produced artificially or naturally can be "compositions of at least" a certain degree of purity if the species or population of species of interest is at least 5, 10, 25, 50, 75, 80, 90, 92, 95, 98, or 99% pure on a weight-weight basis.

As used herein, the term "in vitro" refers to events that occur in an artificial environment, e.g., in a test tube or reaction vessel, in cell culture, etc., rather than within a multi-cellular organism.

As used herein, the term "in vivo" refers to events that occur within a multi-cellular organism such as a human or non-human animal.

An "isolated composition" refers to a composition that is removed from at least 90% of at least one component of a natural sample from which the isolated composition can be obtained. Compositions produced artificially or naturally can be "compositions of at least" a certain degree of purity if the species or population of species of interests is at least 5, 10, 25, 50, 75, 80, 90, 92, 95, 98, or 99% pure on a weight-weight basis.

An "isolated" protein refers to a protein that is removed from at least 90% of at least one component of a natural sample from which the isolated protein can be obtained. Proteins can be "of at least" a certain degree of purity if the species or population of species of interest is at least 5, 10, 25, 50, 75, 80, 90, 92, 95, 98, or 99% pure on a weight-weight basis.

The term "kallikrein" (e.g., plasma kallikrein) refers to peptidases (enzymes that cleave peptide bonds in proteins), a subgroup of the serine protease family. Plasma kallikrein cleaves kininogen to generate kinins, potent pro-inflammatory peptides.

The term "kallikrein inhibitor" refers to any agent or molecule that inhibits kallikrein. For example, DX-88 (also referred to herein as "PEP-1") is a potent (Ki<1 nM) and specific inhibitor of plasma kallikrein (NP_000883). (See also, e.g., WO 95/21601 or WO 2003/103475).

As used herein the term "DX-2922" as used interchangeably with the term "X101-A01". Other variants of this antibody are described below.

| Antibody Identification | Description |
|---|---|
| X63-G06 | Non-germlined Fab discovered using ROLIC, same HC but different LC as M160-G12 |
| X81-B01 | Germlined IgG produced in HEK 293T cells |
| X101-A01 | Germlined IgG produced in CHO cells, same HC and LC sequence as X81-B01 |
| DX-2922 | Alternate nomenclature for X101-A01 |

As used herein the term "DX-2930" as used interchangeably with the term "X124-G01". Other variants of this antibody are described below.

| Antibody Identification | Description |
|---|---|
| M162-A04 | Non-germlined Fab discovered using phage display |
| M199-A08 | Heavy chain CDR3 varied Fab derived by affinity maturation of M162-A04 |
| X115-F02 | Germlined Fab produced in 293T cells, same variable heavy chain as X124-G01 |
| X124-G01 or DX-2930 | Germlined IgG produced in CHO cells, LC and HC sequence as X1115-F02 except that the C-terminal Lys of the HC is removed in X124-G01 (also known as DX-2930). |

The term "modulator" refers to a polypeptide, nucleic acid, macromolecule, complex, molecule, small molecule, compound, species or the like (naturally-occurring or non-naturally-occurring), or an extract made from biological materials such as bacteria, plants, fungi, or animal cells or tissues, that may be capable of causing modulation. Modulators may be evaluated for potential activity as inhibitors or activators (directly or indirectly) of a functional property, biological activity or process, or combination of them, (e.g., agonist, partial antagonist, partial agonist, inverse agonist, antagonist, anti-microbial agents, inhibitors of microbial infection or proliferation, and the like) by inclusion in assays. In such assays, many modulators may be screened at one time. The activity of a modulator may be known, unknown or partially known.

A "non-essential" amino acid residue is a residue that can be altered from the wild-type sequence of the binding agent, e.g., the antibody, without abolishing or more preferably, without substantially altering a biological activity, whereas changing an "essential" amino acid residue results in a substantial loss of activity.

A "patient," "subject" or "host" (these terms are used interchangeably) to be treated by the subject method may mean either a human or non-human animal. In some embodiments, a subject is at risk for or suffers from a kallikrein-mediated disorder, e.g., a bradykinin-mediated disorder, e.g., hereditary angioedema (HAE). In some embodiments, a subject is at risk for or suffers from non-histamine-dependent idiopathic angioedema, rheumatoid arthritis, Crohn's disease, lupus, Alzheimer's disease, septic shock, burn injury, brain ischemia/reperfusion injury, cerebral edema, diabetic retinopathy, diabetic nephropathy, macular edema, vasculitis, arterial or venous thrombosis, thrombosis associated with ventricular assist devices or stents, heparin-induced thrombocytopenia with thrombosis, thromboembolic disease, and coronary heart disease with unstable angina pectoris, edema, eye disease, gout, intestinal bowel disease, oral mucositis, neuropathic pain, inflammatory pain, spinal stenosis-degenerative spine disease, post operative ileus, aortic aneurysm, osteoarthritis, hereditary angioedema, pulmonary embolism, stroke, head trauma or peri-tumor brain edema, sepsis, acute middle cerebral artery (MCA) ischemic event (stroke), restenosis (e.g., after angioplasty), systemic lupus erythematosis nephritis, an autoimmune disease, an inflammatory disease, a cardiovascular disease, a neurological disease, a disease associated with protein misfolding, a disease associated with angiogenesis, hypertensive nephropathy and diabetic nephropathy, allergic and respiratory diseases (e.g. anaphylaxis, asthma, chronic obstructive pulmonary disease, acute respiratory distress syndrome, cystic fibrosis, persistent, rhinitis) and tissue injuries (e.g. burn or chemical injury).

The terms "prekallikrein" and "preplasma kallikrein" are used interchangeably herein and refer to the zymogen form of active plasma kallikrein, which is also known as prekallikrein.

The term "preventing" or to "prevent" a disease in a subject refers to subjecting the subject to a pharmaceutical treatment, e.g., the administration of a drug, such that at least one symptom of the disease is prevented, that is, administered prior to clinical manifestation of the unwanted condition (e.g., disease or other unwanted state of the host animal) so that it protects the host against developing the unwanted condition. "Preventing" a disease may also be referred to as "prophylaxis" or "prophylactic treatment."

As used herein, the term "substantially identical" (or "substantially homologous") is used herein to refer to a first amino acid or nucleic acid sequence that contains a sufficient number of identical or equivalent (e.g., with a similar side chain, e.g., conserved amino acid substitutions) amino acid residues or nucleotides to a second amino acid or nucleic acid sequence such that the first and second amino acid or nucleic acid sequences have (or encode proteins having) similar activities, e.g., a binding activity, a binding preference, or a biological activity. In the case of antibodies, the second antibody has the same specificity and has at least 50%, at least 25%, or at least 10% of the affinity relative to the same antigen.

Sequences similar or homologous (e.g., at least about 85% sequence identity) to the sequences disclosed herein are also part of this application. In some embodiments, the sequence identity can be about 85%, 90%, 91%, 92%, 93%, 94%, 95%, 96%, 97%, 98%, 99% or higher.

In addition, substantial identity exists when the nucleic acid segments hybridize under selective hybridization conditions (e.g., highly stringent hybridization conditions), to the complement of the strand. The nucleic acids may be present in whole cells, in a cell lysate, or in a partially purified or substantially pure form.

Motif sequences for biopolymers can include positions which can be varied amino acids. For example, the symbol "X" in such a context generally refers to any amino acid (e.g., any of the twenty natural amino acids) unless otherwise specified, e.g., to refer to any non-cysteine amino acid. Other allowed amino acids can also be indicated for example, using parentheses and slashes. For example, "(A/W/F/N/Q)" means that alanine, tryptophan, phenylalanine, asparagine, and glutamine are allowed at that particular position.

Statistical significance can be determined by any art known method. Exemplary statistical tests include: the Students T-test, Mann Whitney U non-parametric test, and Wilcoxon non-parametric statistical test. Some statistically significant relationships have a P value of less than 0.05 or 0.02. The terms "induce", "inhibit", "potentiate", "elevate", "increase", "decrease" or the like, e.g., which denote distinguishable qualitative or quantitative differences between two states, may refer to a difference, e.g., a statistically significant difference, between the two states.

As used herein, a "sample", refers to a composition that comprises tissue, e.g., blood, plasma or protein, from a subject. A sample includes both an initial unprocessed sample taken from a subject as well as subsequently processed, e.g., partially purified or preserved forms. Exemplary samples include blood, plasma, tears, or mucus.

A "therapeutically effective dosage" preferably modulates a measurable parameter, e.g., plasma kallikrein activity, by a statistically significant degree or at least about 20%, more preferably by at least about 40%, even more preferably by at least about 60%, and still more preferably by at least about 80% relative to untreated subjects. The ability of a compound to modulate a measurable parameter, e.g., a disease-associated parameter, can be evaluated in an animal model system predictive of efficacy in human disorders and conditions. Alternatively, this property of a composition can be evaluated by examining the ability of the compound to modulate a parameter in vitro.

"Treating" a disease (or condition) in a subject or "treating" a subject having a disease refers to subjecting the subject to a pharmaceutical treatment, e.g., the administration of a drug, such that at least one symptom of the disease is cured, alleviated or decreased.

The term "preventing" a disease in a subject refers to subjecting the subject to a pharmaceutical treatment, e.g., the administration of a drug, such that at least one symptom of the disease is prevented, that is, administered prior to clinical manifestation of the unwanted condition (e.g., disease or other unwanted state of the host animal) so that it protects the host against developing the unwanted condition. "Preventing" a disease may also be referred to as "prophylaxis" or "prophylactic treatment."

A "prophylactically effective amount" refers to an amount effective, at dosages and for periods of time necessary, to achieve the desired prophylactic result. Typically, because a prophylactic dose is used in subjects prior to or at an earlier stage of disease, the prophylactically effective amount will be less than the therapeutically effective amount.

Headings, including alphabetical or numerical headings, are merely for ease of understanding and reading and, absent express indication to the contrary, do not impose temporal order or a hierarchy of preferences.

Contact System Biomarkers

Plasma kallikrein circulates as an inactive zymogen called prekallikrein that is mostly bound to its substrate, high molecular weight kininogen (HMWK). In response to a stimulus, FXII is activated to FXIIa. FXIIa cleaves prekallikrein to form active plasma kallikrein (FIG. 1). Approximately 75-90% of circulating prekallikrein is bound to HMWK through a non-active site interaction with domain 6 of HMWK. Free and HMWK-bound active pKal generate cleaved HMWK and bradykinin. Biomarkers of plasma kallikrein activation are shown in Table 2. The suitability of a biomarker can be demonstrated by following its levels in the presence and absence of an acute attack of HAE. Levels of these biomarkers could also be altered during an attack of bradykinin mediated edema or other disease mediated by pKal activity.

Table 2 below provides markers that can be evaluated by the methods described in Table 2 and elsewhere herein to evaluate subjects for pKal or bradykinin mediated disorders. Table 2 indicates the direction in change in the level of marker associated with a pKal or bradykinin mediated disorders.

Assays for Biomarkers

Levels (e.g., the amount) of biomarkers disclosed herein, or changes in levels of biomarkers disclosed herein, can be assessed using assays described herein and/or assays known in the art. Assays that can be used for assessing levels of biomarkers include, e.g., immunoassays, e.g., Western blots, enzyme linked immunosorbent assays (ELISAs) (e.g., sandwich ELISAs), radioimmunoassays, electrochemiluminescence-based detection assays, and related techniques. Mass spectrometry based approaches can also be used. Assays that rely on a chromogenic substrate can also be employed.

In some embodiments, an electrochemiluminescence detection assay or an assay relying on a combination of electrochemiluminescence and patterned array technology is used (e.g., an ECL or MULTI-ARRAY technology assay from Meso Scale Discovery (MSD)).

(i) Prekallikrein

Prekallikrein levels can be assessed using existing assays for prekallikrein, e.g., immunoassays, e.g., a prekallikrein ELISA. For Example, a prekallikrein ELISA kit is commercially available from antibodiesonline.com (Catalog no.: ABIN858073). Antibodies that bind prekallikrein are known in the art and can be used, e.g., in immunoassays, for the detection of prekallikrein. For example, murine monoclonal anti-human prekallikrein antibodies have been produced. See, e.g., Veloso, D. et al. *Blood,* 1987, 70(4):1053-62. A sheep anti-human prekallikrein antibody is commercially available from GenWay Biotech, Inc. (GenWay ID: GWB-58AC79).

In an embodiment the level of pKal in an aliquot of sample is determined. Then, all prekallikrein in an aliquot of sample is converted to pKal and the level of pKal is measured. Subtracting the first from the second gives the amount of prekallikrein. Determinations of level can be made by enzyme activity.

(ii) Active Plasma Kallikrein

Active plasma kallikrein (active pKal) can be detected, for example, using an immunoassay. The immunoassay can use an antibody that only binds active plasma kallikrein, such as, e.g., DX-2930 or DX-2922. In an embodiment the assay relies on binding of active pKal to a capture reagent, e.g., a kallikrein inhibitor, e.g., a polypeptide that is similar in sequence to DX-88, e.g., one that differs from DX-88 by no more than 1, 2, or 5 amino acid residues, e.g., EPIKAL-2.

In an embodiment, the capture reagent is provided on a substrate, contacted with sample, and the amount bound to capture reagent determined, e.g., with an anti-pKal antibody. In an embodiments the sample handling of the sample, e.g., transfer from one container to another, is minimized, so as to reduce the levels of contact activation. In embodiments, the capture reagent is disposed in the same device, e.g., a collection container, e.g., a blood collection tube, that is used to collect a sample, e.g., blood, from the subject.

Also within the present disclosure is an ex vivo activation assay for determining pKal activity (e.g., a microplate-based pKal activity assay), which can comprise (i) providing a plasma sample from a subject; (ii) incubating the plasma sample with a pKal system activator in the presence of a pKal substrate, wherein the substrate is attached to a label which is capable of releasing a detectable signal after being cleaved by pKal; and (iii) measuring the activity of pKal based on the magnitude of the detectable signal. In some examples, the activator is Factor FXIIa. In some examples, the plasma sample is incubated with the activator, the pKal substrate, and a pKal inhibitor candidate. The method can further comprise evaluating the activity of the

TABLE 2

Biomarkers associated with KMA

| Biomarker | Assay | Basal Level in HAE patient relative to normal | Δ due to contact activation | Comments |
|---|---|---|---|---|
| prekallikrein | ELISA or enzyme activity | Unchanged (~500 nM) | decrease | Prekallikrein can be converted to active kallikrein or an ELISA to detect prekallikrein can be used. This approach may be complicated due to individual variations in patient levels and will compete with antibodies specific for active pKal |
| Active pKal | ELISA or enzyme activity | None expected | increase | An antibody specific for active pKal (e.g., DX-2930, DX-2922) can be used in an immunoassay for the detection of active pKal in plasma. This approach however has limitations. The active pKal in the plasma appears to be complexed with α-2-macroglobulin (α2M), which appears to compete for the epitope on pKal of some antibodies. Circulating pKal is largely bound to HMWK through an interaction that does not prevent the binding our pKal specific antibodies to the active site. Furthermore, the assay may be subject to interference in certain treated samples. |
| α2M-pKal complex | ELISA or MSD | Could be elevated, if recent attack | increase | α2M-pKal complex is elevated during a HAE attack and sepsis. |
| C1INH-pKal complex | ELISA or MSD | Could be elevated, if recent attack | increase | C1INH-pKal complex is elevated during cardiopulmonary bypass. C1INH inhibitor complexes may be cleared rapidly. Consequently, the assay should be sufficiently sensitive to detect elevations at a sampling time following an attack. |
| Intact HMWK | ELISA | Unchanged | decrease | Test are available to measure intact kininogen using APTT with kininogen deficient plasma or immunoassays: www.diapharma.com/downloads/68201025811.pdf |
| Cleaved HMWK | ELISA | Unchanged | increase | Cleaved kininogen can increase to ~47% total kininogen during an HAE attack. -Cleaved kininogen is also elevated during sepsis, cirrhosis. Assays can use either a) an antibody that is specific for cleaved kininogen as opposed to intact kininogen; or b) an assay format capable of separating and quantifying cleaved and intact kininogen (e.g. Western blot). This assay would not be sensitive to circulating anti-pKal antibody and is not dependent on whether cell surface bound active pKal is the main culprit in localized bradykinin-mediated angioedema. | pKal inhibitor candidate, wherein a reduced level of pKal activity in the presence of the pKal inhibitor candidate as related to the level of pKal activity in the absence of the pKal inhibitor candidate indicates that the inhibitor candidate is effective.

The method can also further comprise assessing whether the subject has or is at risk for a disease associated with pKal; wherein an elevated level of pKal activity as compared to a predetermined value (e.g., a level of pKal activity in sample(s) from a healthy subject or population of healthy subjects) indicates that the subject has or is at risk for the disease.

The method can also further comprise evaluating the efficacy of the treatment, such as a treatment for a disease associated with pKal. Multiple biosamples (e.g., plasma samples) can be obtained from a patient having a pKal-related disease such as HAE and being treated by a therapeutic agent such as an pKal inhibitor before, during the course of the treatment, and/or after the treatment. The levels of pKal activity or a biomarker indicative of pKal activity in those biosamples can be measured using any of the assay methods disclosed herein. A reduced level of pKal activity or a reduced level of one or more biomarkers indicative of pKal activity as to compared that before the treatment or a reduced level of pKal activity/biomarker over the course of the treatment indicates that the treatment is effective.

(iii) α2M-pKal Complex

The plasma kallikrein alpha 2 macroglobulin complex (α2M-pKal complex) can be detected, e.g., using an immunoassay. For example, a sandwich based ELISA assay has been developed as described in Example 2. A quantitative sandwich ELISA was also reported in Kaufman, N. et al. Blood, 1991, 77(12):2660-2667 and in Wachtfogel, Y. T. et al., 1989, Blood, 73:468-471. An immunoimmobilization enzyme assay was reported in Harpel, P. C. et al., J Biol Chem, 1985, 260(7):4257-63). A chromogenic substrate assay can also be used, e.g., using the chromogenic substrate S-2302 available at chromogenicsubstrates.com and the protocol provided at chromogenicsubstrates.com/methods/chromogenic_substrates_methods_kallikrein-like.htm.

(iv) C1INH-pKal Complex

The C1INH-pKal complex can be detected, for example, using immunoassays, e.g., ELISA methods, e.g., methods described in Example 3. For example, a sandwich ELISA in which an anti-pKal antibody (e.g., mouse mAb 13G11) is the capture antibody and an antibody against C1INH is used as the detector antibody, or a sandwich ELISA in which an antibody against C1INH is used as the capture antibody and an anti-pKal antibody (e.g., mouse mAb 13G11) is the detector antibody can be used. Antibodies against C1INH are known in the art. For example, a mouse monoclonal antibody against human C1 inhibitor is available from ABBIOTEC (Catalog No. 250122). Another mouse monoclonal antibody against human C1 inhibitor (4G12) is available from pierce-antibodies.com (Product # LF-MA0136). Goat anti-human C1 inhibitor antibody is available from Quidel (Catalog No. A300). Another ELISA sandwich assay for detection of C1INH-pKal complexes was used in Wachtfogel, Y. T. et al., 1989, Blood, 73:468-471.

(v) Intact HMWK

Intact high molecular weight kininogen (HMWK) can be assayed, for example, using coagulant or immunological methods, e.g., radioimmunoassay (see, e.g., Kerbiriou-Nabias, D. M., Br J Haematol, 1984, 56(2):2734-86). A monoclonal antibody to the light chain of human HMWK is known. See, e.g., Reddigari, S. R. & Kaplan, A. P., Blood, 1999, 74:695-702. An assay for HMWK that relies on a chromogenic substrate can also be used. See, e.g., Scott, C. F. et al. Thromb Res, 1987, 48(6):685-700; Gallimore, M. J. et al. Thromb Res, 2004, 114(2):91-96.

The human gene encoding HMWK is kininogen 1 (KNG1). KNG1 is transcribed and alternatively spliced to form mRNAs that encode either HMWK or low molecular weight kininogen (LMWK). An exemplary protein sequence of HMWK is provided below:

```
>gi|156231037|ref|NP_001095886.1| kininogen-1
isoform 1 precursor [Homo sapiens]
                                         (SEQ ID NO: 5)
MKLITILFLCSRLLLSLTQESQSEEIDCNDKDLFKAVDAALKKYNSQNQS

NNQFVLYRITEATKTVGSDTFYSFKYEIKEGDCPVQSGKTWQDCEYKDAA

KAATGECTATVGKRSSTKFSVATQTCQITPAEGPVVTAQYDCLGCVHPIS

TQSPDLEPILRHGIQYFNNNTQHSSLFMLNEVKRAQRQVVAGLNFRITYS

IVQTNCSKENFLFLTPDCKSLWNGDTGECTDNAYIDIQLRIASFSQNCDI

YPGKDFVQPPTKICVGCPRDIPTNSPELEETLTHTITKLNAENNATFYFK

IDNVKKARVQVVAGKKYFIDEVARETTCSKESNEELTESCETKKLGQSLD

CNAEVYVVPWEKKIYPTVNCQPLGMISLMKRPPGFSPFRSSRIGEIKEET

TVSPPHTSMAPAQDEERDSGKEQGHTRRHDWGHEKQRKHNLGHGHKHERD

QGHGHQRGHGLGHGHEQQHGLGHGHKFKLDDDLEHQGGHVLDHGHKHKHG

HGHGKHKNKGKKNGKHNGWKTEHLASSSEDSTTPSAQTQEKTEGPTPIPS

LAKPGVTVTFSDFQDSDLIATMMPPISPAPIQSDDDWIPDIQIDPNGLSF

NPISDFPDTTSPKCPGRPWKSVSEINPTTQMKESYYFDLTDGLS
```

(vi) Cleaved HMWK

Cleaved high molecular weight kininogen (HMWK), also referred to herein as "cleaved kininogen," can be assessed, for example, using methods described in Example 1, e.g., Western blot. Antibodies that bind cleaved HMWK, such as, e.g., the mouse mAb clone 11H05 can be used. Additionally, cleaved HMWK may be assessed using mass spectrometry. Immunoblotting techniques for assessing levels of cleaved HMWK are known in the art. See, e.g., Buhler R. et al. Blood Coagul Fibrinolysis, 1995, 6(3):223-232.

Exemplary sequences of the heavy and light chains of cleaved kininogen are provided below.

```
> cleaved kininogen-1 heavy chain
                                         (SEQ ID NO: 6)
QESQSEEIDCNDKDLFKAVDAALKKYNSQNQSNNQFVLYRITEATKTVG

SDTFYSFKYEIKEGDCPVQSGKTWQDCEYKDAAKAATGECTATVGKRSS

TKFSVATQTCQITPAEGPVVTAQYDCLGCVHPISTQSPDLEPILRHGIQ

YFNNNTQHSSLFMLNEVKRAQRQVVAGLNFRITYSIVQTNCSKENFLFL

TPDCKSLWNGDTGECTDNAYIDIQLRIASFSQNCDIYPGKDFVQPPTKI

CVGCPRDIPTNSPELEETLTHTITKLNAENNATFYFKIDNVKKARVQVV

AGKKYFIDEVARETTCSKESNEELTESCETKKLGQSLDCNAEVYVVPWE

KKIYPTVNCQPLGMISLMK

> cleaved kininogen-1 light chain
                                         (SEQ ID NO: 7)
SSRIGEIKEETTVSPPHTSMAPAQDEERDSGKEQGHTRRHDWGHEKQRK

HNLGHGHKHERDQGHGHQRGHGLGHGHEQQHGLGHGHKFKLDDDLEHQG
```

-continued

GHVLDHGHKHKHGHGHGKHKNKGKKNGKHNGWKTEHLASSSEDSTTPSA

QTQEKTEGPTPIPSLAKPGVTVTFSDFQDSDLIATMMPPISPAPIQSDD

DWIPDIQIDPNGLSFNPISDFPDTTSPKCPGRPWKSVSEINPTTQMKES

YYFDLTDGLS

In some embodiments, the present present disclosure provides an ex vivo activation method. Such a method can comprise (i) incubating a plasma sample obtained from a subject with an activator of the plasma kallikrein (pKal) system (e.g., Factor FXIIa); (ii) measuring the levels of intact high molecular weight kininogen (HMWK), the cleaved HMWK, or both, in the plasma sample before and after the incubation; and (iii) determining the reduction of intact HMWK in the sample after the activation. In some examples, the levels of intact HMWK and cleaved HMWK are measured by a Western blot analysis, e.g., a Simple Western™ Protein Simple®, Western blot analysis. Simple Western™ assays are known in the art (see, e.g., Rustandi et al. Electrophoresis. 2012 September; 33(17):2790-7). Simple Western™ products are also available commercially (see, e.g., ProteinSimple®, Santa Clara, Calif.).

The ex vivo activation method as described herein can be used to evaluate the activity of a pKal inhibitor candidate in inhibiting plasma activation. More specifically, the plasma sample can be incubated with the activator in the presence of the pKal inhibitor candidate. If the activation level is reduced in the present of the inhibitor candidate, it indicates that the candidate is effective in inhibiting plasma activation.

In other embodiments, the present present disclosure provides methods for measuring endogenous cleaved HMWK. Such a method can comprise (i) providing a plasma sample from a subject; and (ii) measuring the level of cleaved HMWK in the plasma sample. In some examples, the level of cleaved HMWK is measured by Protein Simple Western blot analysis.

The endogenous cleaved HMWK assay can be applied to identify subjects having or suspected of having a disease associated with the pKal system, e.g., those described herein. In some examples, the plasma sample is obtained from a subject having or suspected of having a disease associated with the pKal system. If the endogenous cleaved HMWK in the subject is elevated as compared to that from a health subject, it indicates that the subject has or is suspected of having the disease.

Alternatively or in addition, the endogenous cleaved HMWK assay can be used to evaluate the efficacy of a treatment for a disease associated with the pkal system. In that case, the plasma sample is obtained from a subject having the disease and is treated by a pKal inhibitor. If a reduced level of cleaved HMWK is observed after the treatment as compared with that before the treatment, it indicates that the pKal inhibitor is effective.

As a further alternative or addition, the assay can also be used to assess whether a subject has or is at risk for a disease associated with pKal; wherein an elevated level of cleaved HMWK as compared to a predetermined value (e.g., a level of cleaved HMWK in sample(s) from a healthy subject or population of healthy subjects) indicates that the subject has or is at risk for the disease.

The method can also further comprise evaluating the efficacy of the treatment, such as a treatment for a disease associated with pKal. Multiple biosamples (e.g., plasma samples) can be obtained from a patient having a pKal-related disease such as HAE and being treated by a therapeutic agent such as an pKal inhibitor before, during the course of the treatment, and/or after the treatment. The levels of intact HMWK and/or cleaved HMWK in those bio-samples can be measured using any of the assay methods disclosed herein. A reduced level of cleaved HMWK as to compared that before the treatment or a reduced level of cleaved HMWK over the course of the treatment indicates that the treatment is effective.

Antibodies

Antibodies and antigen-binding fragments may be used in provided methods. In some embodiments, a capture agent is or comprises an antibody or antigen-binding fragment. In some embodiments, a detection agent is or comprises an antibody or antigen-binding fragment. In some embodiments, a therapeutic composition for treatment of a pKal-mediated or bradykinin-mediated disorder is or comprises an antibody or antigen binding fragment.

As used herein, the term "antibody" refers to a protein that includes at least one immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab and sFab fragments, F(ab')$_2$, Fd fragments, Fv fragments, scFv, and domain antibodies (dAb) fragments (de Wildt et al., Eur J Immunol. 1996; 26(3):629-39)) as well as complete antibodies. An antibody can have the structural features of IgA, IgG, IgE, IgD, IgM (as well as subtypes thereof). Antibodies may be from any source, but primate (human and non-human primate) and primatized are preferred.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) J. Mol. Biol. 196:901-917, see also www.hgmp.mrc.ac.uk). Kabat definitions are used herein. Each VH and VL is typically composed of three CDRs and four FRs, arranged from amino-terminus to carboxy-terminus in the following order: FR1, CDR1, FR2, CDR2, FR3, CDR3, FR4.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. In IgGs, the heavy chain constant region includes three immunoglobulin domains, CH1, CH2 and CH3. The light chain constant region includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system. The light chains of the immunoglobulin may be of types kappa or lambda. In one embodiment, the antibody is glycosylated. An antibody can be functional for antibody-dependent cytotoxicity and/or complement-mediated cytotoxicity.

One or more regions of an antibody can be human or effectively human. For example, one or more of the variable regions can be human or effectively human. For example, one or more of the CDRs can be human, e.g., HC CDR1, HC CDR2, HC CDR3, LC CDR1, LC CDR2, and LC CDR3. Each of the light chain CDRs can be human. HC CDR3 can be human. One or more of the framework regions can be human, e.g., FR1, FR2, FR3, and FR4 of the HC or LC. For example, the Fc region can be human. In one embodiment, all the framework regions are human, e.g., have a sequence of a framework of an antibody produced by a human somatic cell, e.g., a hematopoietic cell that produces immunoglobulins or a non-hematopoietic cell. In one embodiment, the human sequences are germline sequences, e.g., encoded by a germline nucleic acid. In one embodiment, the framework (FR) residues of a selected Fab can be converted to the amino-acid type of the corresponding residue in the most similar primate germline gene, especially the human germline gene. One or more of the constant regions can be human or effectively human. For example, at least 70, 75, 80, 85, 90, 92, 95, 98, or 100% of an immunoglobulin variable domain, the constant region, the constant domains (CH1, CH2, CH3, CL1), or the entire antibody can be human or effectively human.

All or part of an antibody can be encoded by an immunoglobulin gene or a segment thereof. Exemplary human immunoglobulin genes include the kappa, lambda, alpha (IgA1 and IgA2), gamma (IgG1, IgG2, IgG3, IgG4), delta, epsilon and mu constant region genes, as well as the many immunoglobulin variable region genes. Full-length immunoglobulin "light chains" (about 25 KDa or about 214 amino acids) are encoded by a variable region gene at the NH2-terminus (about 110 amino acids) and a kappa or lambda constant region gene at the COOH—terminus. Full-length immunoglobulin "heavy chains" (about 50 KDa or about 446 amino acids), are similarly encoded by a variable region gene (about 116 amino acids) and one of the other aforementioned constant region genes, e.g., gamma (encoding about 330 amino acids). The length of human HC varies considerably because HC CDR3 varies from about 3 amino-acid residues to over 35 amino-acid residues.

The term "antigen-binding fragment" of a full length antibody refers to one or more fragments of a full-length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')$_2$ fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., U.S. Pat. Nos. 5,260,203, 4,946,778, and 4,881,175; Bird et al. (1988) *Science* 242: 423-426; and Huston et al. (1988) *Proc. Natl. Acad. Sci. USA* 85:5879-5883.

Antibody fragments can be obtained using any appropriate technique including conventional techniques known to those with skill in the art. The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition, irrespective of how the antibody was generated.

As used herein, a "humanized" immunoglobulin variable region refers to an immunoglobulin variable region that is modified to include a sufficient number of human framework amino acid positions such that the immunoglobulin variable region does not elicit an immunogenic response in a normal human. Descriptions of "humanized" immunoglobulins include, for example, U.S. Pat. No. 6,407,213 and U.S. Pat. No. 5,693,762.

The inhibition constant (Ki) provides a measure of inhibitor potency; it is the concentration of inhibitor required to reduce enzyme activity by half and is not dependent on enzyme or substrate concentrations. The apparent Ki ($K_{i,app}$) is obtained at different substrate concentrations by measuring the inhibitory effect of different concentrations of inhibitor (e.g., inhibitory binding protein) on the extent of the reaction (e.g., enzyme activity); fitting the change in pseudo-first order rate constant as a function of inhibitor concentration to the Morrison equation (Equation 1) yields an estimate of the apparent Ki value. The Ki is obtained from the y-intercept extracted from a linear regression analysis of a plot of Ki,app versus substrate concentration.

$$v = v_o - v_o \left( \frac{(K_{i,app} + I + E) - \sqrt{(K_{i,app} + I + E)^2 - 4 \cdot I \cdot E}}{2 \cdot E} \right) \quad \text{Equation 1}$$

Where v=measured velocity; $v_o$=velocity in the absence of inhibitor; $K_{i,app}$=apparent inhibition constant; I=total inhibitor concentration; and E=total enzyme concentration.

Hereditary Angioedema (HAE)

In some embodiments, the disease or condition that involves plasma kallikrein activity is hereditary angioedema (HAE). Hereditary angioedema (HAE) is also known as "Quincke edema," C1 esterase inhibitor deficiency, C1 inhibitor deficiency, and hereditary angioneurotic edema (HANE). HAE is characterized by recurrent episodes of severe swelling (angioedema), which can affect, e.g., the limbs, face, genitals, gastrointestinal tract, and airway. Symptoms of HAE include, e.g., swelling in the arms, legs, lips, eyes, tongue, and/or throat; airway blockage that can involve throat swelling and sudden hoarseness; repeat episodes of abdominal cramping without obvious cause; and/or swelling of the intestines, which can be severe and can lead to abdominal cramping, vomiting, dehydration, diarrhea, pain, and/or shock. About one-third of individuals with this HAE develop a non-itchy rash called erythema *marginatum* during an attack.

Swelling of the airway can be life threatening and causes death in some patients. Mortality rates are estimated at 15-33%. HAE leads to about 15,000-30,000 emergency department visits per year.

Trauma or stress, e.g., dental procedures, sickness (e.g., viral illnesses such as colds and the flu), menstruation, and surgery can trigger an attack of angioedema. To prevent acute attacks of HAE, patients can attempt to avoid specific stimuli that have previously caused attacks. However, in many cases, an attack occurs without a known trigger. Typically, HAE symptoms first appear in childhood and worsen during puberty. On average, untreated individuals have an attack every 1 to 2 weeks, and most episodes last for about 3 to 4 days (ghr.nlm.nih.gov/condition/hereditary-angioedema). The frequency and duration of attacks vary greatly among people with hereditary angioedema, even among people in the same family.

There are three types of HAE, known as types I, II, and III. It is estimated that HAE affects 1 in 50,000 people, that type I accounts for about 85 percent of cases, type II accounts for about 15 percent of cases, and type III is very rare. Type III is the most newly described form and was originally thought to occur only in women, but families with affected males have been identified.

HAE is inherited in an autosomal dominant pattern, such that an affected person can inherit the mutation from one affected parent. New mutations in the gene can also occur, and thus HAE can also occur in people with no history of the disorder in their family. It is estimated that 20-25% of cases result from a new spontaneous mutation.

Mutations in the SERPING1 gene cause hereditary angioedema type I and type II. The SERPING1 gene provides instructions for making the C1 inhibitor protein, which is important for controlling inflammation. C1 inhibitor blocks the activity of certain proteins that promote inflammation. Mutations that cause hereditary angioedema type I lead to reduced levels of C1 inhibitor in the blood. In contrast, mutations that cause type II result in the production of a C1 inhibitor that functions abnormally. Without the proper levels of functional C1 inhibitor, excessive amounts of bradykinin are generated. Bradykinin promotes inflammation by increasing the leakage of fluid through the walls of blood vessels into body tissues. Excessive accumulation of fluids in body tissues causes the episodes of swelling seen in individuals with hereditary angioedema type I and type II.

Mutations in the F12 gene are associated with some cases of hereditary angioedema type III. The F12 gene provides instructions for making coagulation factor XII. In addition to playing a critical role in blood clotting (coagulation), factor XII is also an important stimulator of inflammation and is involved in the production of bradykinin. Certain mutations in the F12 gene result in the production of factor XII with increased activity. As a result, more bradykinin is generated and blood vessel walls become more leaky, which leads to episodes of swelling. The cause of other cases of hereditary angioedema type III remains unknown. Mutations in one or more as-yet unidentified genes may be responsible for the disorder in these cases.

HAE can present similarly to other forms of angioedema resulting from allergies or other medical conditions, but it differs significantly in cause and treatment. When hereditary angioedema is misdiagnosed as an allergy, it is most commonly treated with antihistamines, steroids, and/or epinephrine, which are typically ineffective in HAE, although epinephrine can be used for life-threatening reactions. Misdiagnoses have also resulted in unnecessary exploratory surgery for patients with abdominal swelling, and in some HAE patients abdominal pain has been incorrectly diagnosed as psychosomatic.

C1 inhibitor therapies, as well as other therapies for HAE, are described in Kaplan, A. P., J Allergy Clin Immunol, 2010, 126(5):918-925.

Acute treatment of HAE attacks is provided to halt progression of the edema as quickly as possible. C1 inhibitor concentrate from donor blood, which is administered intravenously, is one acute treatment; however, this treatment is not available in many countries. In emergency situations where C1 inhibitor concentrate is not available, fresh frozen plasma (FFP) can be used as an alternative, as it also contains C1 inhibitor.

Purified C1 inhibitor, derived from human blood, has been used in Europe since 1979. Several C1 inhibitor treatments are now available in the U.S. and two C1 inhibitor products are now available in Canada. Berinert P (CSL Behring), which is pasteurized, was approved by the F.D.A. in 2009 for acute attacks. Cinryze (ViroPharma), which is nanofiltered, was approved by the F.D.A. in 2008 for prophylaxis. Rhucin (Pharming) is a recombinant C1 inhibitor under development that does not carry the risk of infectious disease transmission due to human blood-borne pathogens.

Treatment of an acute HAE attack also can include medications for pain relief and/or IV fluids.

Other treatment modalities can stimulate the synthesis of C1 inhibitor, or reduce C1 inhibitor consumption. Androgen medications, such as danazol, can reduce the frequency and severity of attacks by stimulating production of C1 inhibitor.

*Helicobacter pylori* can trigger abdominal attacks. Antibiotics to treat h. *pylori* will decrease abdominal attacks.

Newer treatments attack the contact cascade. Ecallantide (KALBITOR®, DX-88, Dyax) inhibits plasma kallikrein and has been approved in the U.S. Icatibant (FIRAZYR®, Shire) inhibits the bradykinin B2 receptor, and has been approved in Europe and the U.S.

Diagnosis of HAE can rely on, e.g., family history and/or blood tests. Laboratory findings associated with HAE types I, II, and III are described, e.g., in Kaplan, A. P., J Allergy Clin Immunol, 2010, 126(5):918-925. In type I HAE, the level of C1 inhibitor is decreased, as is the level of C4, whereas C1q level is normal. In type II HAE, the level of C1 inhibitor is normal or increased; however, C1 inhibitor function is abnormal. C4 level is decreased and C1q level is normal. In type III, the levels of C1 inhibitor, C4, and C1q can all be normal.

Symptoms of HAE can be assessed, for example, using questionnaires, e.g., questionnaires that are completed by patients, clinicians, or family members. Such questionnaires are known in the art and include, for example, visual analog scales. See, e.g., McMillan, C. V. et al. Patient. 2012; 5(2):113-26.

Other pKal-Mediated or Bradykinin-Mediated Disorders

Other exemplary diseases or conditions associated with plasma kallikrein activity include non-histamine-dependent idiopathic angioedema, rheumatoid arthritis, Crohn's disease, lupus, Alzheimer's disease, septic shock, burn injury, brain ischemia/reperfusion injury, cerebral edema, diabetic retinopathy, diabetic nephropathy, macular edema, vasculitis, arterial or venous thrombosis, thrombosis associated with ventricular assist devices or stents, heparin-induced thrombocytopenia with thrombosis, thromboembolic disease, and coronary heart disease with unstable angina pectoris, edema, eye disease, gout, intestinal bowel disease, oral mucositis, neuropathic pain, inflammatory pain, spinal stenosis-degenerative spine disease, post operative ileus, aortic aneurysm, osteoarthritis, hereditary angioedema, pulmonary embolism, stroke, head trauma or peri-tumor brain edema, sepsis, acute middle cerebral artery (MCA) ischemic event (stroke), restenosis (e.g., after angioplasty), systemic lupus erythematosis nephritis, an autoimmune disease, an inflammatory disease, a cardiovascular disease, a neurological disease, a disease associated with protein misfolding, a disease associated with angiogenesis, hypertensive nephropathy and diabetic nephropathy, allergic and respiratory diseases (e.g. anaphylaxis, asthma, chronic obstructive pulmonary disease, acute respiratory distress syndrome, cystic fibrosis, persistent, rhinitis) and tissue injuries (e.g. burn or chemical injury).

Treatment

A subject at risk for or suffering from a pKal-mediated or bradykinin-mediated disorder, as identified using an assay method such as those described herein, may be treated with any appropriate therapeutic agent. In some embodiments, provided methods include selecting a treatment for a subject based on the output of a provided assay, e.g., biomarker detection.

In some embodiments, the method comprises one or both of selecting or administering a therapeutic agent, e.g., a kallikrein binding agent as described herein, e.g., a bradykinin B2 receptor antagonist as described herein, e.g., a C1-INH replacement agent as described herein, for administration to the subject based on the output of the assay, e.g., biomarker detection.

In some embodiments a plasma kallikrein binding protein or polypeptide is administered to a subject. In some embodiments, the kallikrein binding agent is a kallikrein inhibitor, e.g., peptide, a small molecule inhibitor, a kallikrein antibody, or a fragment thereof. In some embodiments, an antagonist of bradykinin B2 receptor is administered to a subject. In some embodiments, a C1-INH replacement therapeutic agent is administered to a subject.

The therapeutic agent, e.g., kallikrein inhibitor, e.g., bradykinin B2 receptor antagonist, e.g., C1-INH replacement agent, may be administered along with another therapy as part of a combination therapy for treatment of the disease or condition that involves plasma kallikrein and/or bradykinin activity. Combination therapy, e.g., with one or more of a kallikrein inhibitor, bradykinin B2 receptor antagonist, or C1-INH replacement agent, e.g., with one or more of a kallikrein inhibitor, bradykinin B2 receptor antagonist or C1-INH replacement agent and another therapy, may be provided in multiple different configurations. The first agent may be administered before or after the administration of the other therapy. In some situations, the first agent and another therapy (e.g., a therapeutic agent) are administered concurrently, or in close temporal proximity (e.g., a short time interval between the injections, such as during the same treatment session). The first agent and the other therapy may also be administered at greater temporal intervals.

Plasma Kallikrein Binding Agents

Plasma kallikrein binding agents (e.g., binding proteins, e.g., polypeptides, e.g., inhibitory polypeptides, e.g., antibodies, e.g., inhibitory antibodies, or other binding agents, e.g., small molecules) are useful therapeutic agents for a variety of diseases and conditions, e.g., diseases and conditions that involve plasma kallikrein activity. For example, in some embodiments, the disease or condition that involves plasma kallikrein activity is hereditary angioedema (HAE). In some embodiments a plasma kallikrein binding protein or polypeptide is administered to a subject at risk or suffering from a pKal-mediated or bradykinin-mediated disorder.

A number of useful protein inhibitors of kallikrein, either tissue and/or plasma kallikrein, include a Kunitz domain. As used herein, a "Kunitz domain" is a polypeptide domain having at least 51 amino acids and containing at least two, and preferably three, disulfides. The domain is folded such that the first and sixth cysteines, the second and fourth, and the third and fifth cysteines form disulfide bonds (e.g., in a Kunitz domain having 58 amino acids, cysteines can be present at positions corresponding to amino acids 5, 14, 30, 38, 51, and 55, according to the number of the BPTI homologous sequences provided below, and disulfides can form between the cysteines at position 5 and 55, 14 and 38, and 30 and 51), or, if two disulfides are present, they can form between a corresponding subset of cysteines thereof. The spacing between respective cysteines can be within 7, 5, 4, 3, 2, 1 or 0 amino acids of the following spacing between positions corresponding to: 5 to 55, 14 to 38, and 30 to 51, according to the numbering of the BPTI sequence provided below. The BPTI sequence can be used as a reference to refer to specific positions in any generic Kunitz domain. Comparison of a Kunitz domain of interest to BPTI can be performed by identifying the best fit alignment in which the number of aligned cysteines in maximized.

The 3D structure (at high resolution) of the Kunitz domain of BPTI is known. One of the X-ray structures is deposited in the Brookhaven Protein Data Bank as "6PTI". The 3D structure of some BPTI homologues (Eigenbrot et al., (1990) Protein Engineering, 3(7):591-598; Hynes et al., (1990) Biochemistry, 29:10018-10022) are known. At least eighty one Kunitz domain sequences are known. Known human homologues include three Kunitz domains of LACI also known as tissue factor pathway inhibitor (TFPI) (Wun et al., (1988) J. Biol. Chem. 263(13):6001-6004; Girard et al., (1989) Nature, 338:518-20; Novotny et al, (1989) J. Biol. Chem., 264(31):18832-18837) two Kunitz domains of Inter-α-Trypsin Inhibitor, APP-I (Kido et al., (1988) J. Biol. Chem., 263(34):18104-18107), a Kunitz domain from collagen, three Kunitz domains of TFPI-2 (Sprecher et al., (1994) PNAS USA, 91:3353-3357), the Kunitz domains of hepatocyte growth factor activator inhibitor type 1, the Kunitz domains of Hepatocyte growth factor activator inhibitor type 2, the Kunitz domains described in U.S. Patent Publication No.: 2004-0152633. LACI is a human serum phosphoglycoprotein with a molecular weight of 39 kDa (amino acid sequence in Table 1) containing three Kunitz domains.

TABLE 1

Exemplary Natural Kunitz Domains

```
LACI:       1  MIYTMKKVHA LWASVCLLLN LAPAPLNAds eedeehtiit dtelpplklM
(SEQ ID    51  HSFCAFKADD GPCKAIMKRF FFNIFTRQCE EFIYGGCEGN QNRFESLEEC
NO: 1)    101  KKMCTRDnan riikttlqqe kpdfCfleed pqiCrqyitr yfynnqtkqC
          151  erfkyqgClg nmnnfetlee CkniCedqpn gfqvdnygtq lnavnnsltp
          201  qstkvpslfe fhgpswCltp adrglCrane nrfyynsvig kCrpfkysgC
          251  ggnennftsk qeClraCkkg fiqriskggl iktkrkrkkq rvkiayeeif
          301  vknm The signal sequence (1-28) is uppercase and underscored
               LACI-K1 (50-107) is uppercase
               LACI-K2 (121-178) is underscored
               LACI-K3 (211-270) is bold BPTI                       1        2        3        4        5
(SEQ ID    1234567890123456789012345678901234567890123456789012345678
NO: 2)     RPDFCLEPPYTGPCKARIIRYFYNAKAGLCQTFVYGGCRAKRNNFKSAEDCMRTCGGA
```

The Kunitz domains above are referred to as LACI-K1 (residues 50 to 107), LACI-K2 (residues 121 to 178), and LACI-K3 (213 to 270). The cDNA sequence of LACI is reported in Wun et al. (J. Biol. Chem., 1988, 263(13):6001-6004). Girard et al. (Nature, 1989, 338:518-20) reports mutational studies in which the P1 residues of each of the three Kunitz domains were altered. LACI-K1 inhibits FactorVIIa (F.VIIa) when F.VIIa is complexed to tissue factor and LACI-K2 inhibits Factor Xa.

Proteins containing exemplary Kunitz domains include the following, with SWISS-PROT Accession Numbers in parentheses:

A4_HUMAN (P05067), A4_MACFA (P53601), A4_MACMU (P29216), A4_MOUSE (P12023), A4_RAT (P08592), A4_SAISC (Q95241), AMBP_PLEPL (P36992), APP2_HUMAN (Q06481), APP2_RAT (P15943), AXP1_ANTAF (P81547), AXP2_ANTAF (P81548), BPT1_BOVIN (P00974), BPT2_BOVIN (P04815), CA17_HUMAN (Q02388), CA36_CHICK (P15989), CA36_HUMAN (P12111), CRPT_BOOMI (P81162), ELAC_MACEU (062845), ELAC_TRIVU (Q29143), EPPI_HUMAN (095925), EPPI_MOUSE (Q9DA01), HTIB_MANSE (P26227), IBP_CARCR (P00993), IBPC_BOVIN (P00976), IBPI_TACTR (P16044), IBPS_BOVIN (P00975), ICS3_BOMMO (P07481), IMAP_DROFU (P11424), IP52_ANESU (P10280), ISC1_BOMMO (P10831), ISC2_BOMMO (P10832), ISH1_STOHE (P31713), ISH2_STOHE (P81129), ISIK_HELPO (P00994), ISP2_GALME (P81906), IVB1_BUNFA (P25660), IVB1_BUNMU (P00987), IVB1_VIPAA (P00991), IVB2_BUNMU (P00989), IVB2_DABRU (P00990), IVB2_HEMHA (P00985), IVB2_NAJNI (P00986), IVB3_VIPAA (P00992), IVBB_DENPO (P00983), IVBC_NAJNA (P19859), IVBC_OPHHA (P82966), IVBE_DENPO (P00984), IVBI_DENAN (P00980), IVBI_DENPO (P00979), IVBK_DENAN (P00982), IVBK_DENPO (P00981), IVBT_ERIMA (P24541), IVBT_NAJNA (P20229), MCPI_MELCP (P82968), SBPI_SARBU (P26228), SPT3_HUMAN (P49223), TKD1_BOVIN (Q28201), TKD1_SHEEP (Q29428), TXCA_DENAN (P81658), UPTI_PIG (Q29100), AMBP_BOVIN (P00978), AMBP_HUMAN (P02760), AMBP_MERUN (Q62577), AMBP_MESAU (Q60559), AMBP_MOUSE (Q07456), AMBP_PIG (P04366), AMBP_RAT (Q64240), IATR_HORSE (P04365), IATR_SHEEP (P13371), SPT1_HUMAN (043278), SPT1_MOUSE (Q9R097), SPT2_HUMAN (043291), SPT2_MOUSE (Q9WU03), TFP2_HUMAN (P48307), TFP2_MOUSE (035536), TFPI_HUMAN (P10646), TFPI_MACMU (Q28864), TFPI_MOUSE (054819), TFPI_RABIT (P19761), TFPI_RAT (Q02445), YN81_CAEEL (Q03610)

A variety of methods can be used to identify a Kunitz domain from a sequence database. For example, a known amino acid sequence of a Kunitz domain, a consensus sequence, or a motif (e.g., the ProSite Motif) can be searched against the GenBank sequence databases (National Center for Biotechnology Information, National Institutes of Health, Bethesda Md.), e.g., using BLAST; against Pfam database of HMMs (Hidden Markov Models) (e.g., using default parameters for Pfam searching; against the SMART database; or against the ProDom database. For example, the Pfam Accession Number PF00014 of Pfam Release 9 provides numerous Kunitz domains and an HMM for identify Kunitz domains. A description of the Pfam database can be found in Sonhammer et al. (1997) *Proteins* 28(3):405-420 and a detailed description of HMMs can be found, for example, in Gribskov et al. (1990) *Meth. Enzymol.* 183:146-159; Gribskov et al. (1987) *Proc. Natl. Acad. Sci. USA* 84:4355-4358; Krogh et al. (1994) *J. Mol. Biol.* 235:1501-1531; and Stultz et al. (1993) *Protein Sci.* 2:305-314. The SMART database (Simple Modular Architecture Research Tool, EMBL, Heidelberg, Del.) of HMMs as described in Schultz et al. (1998), *Proc. Natl. Acad. Sci. USA* 95:5857 and Schultz et al. (2000) *Nucl. Acids Res* 28:231. The SMART database contains domains identified by profiling with the hidden Markov models of the HMMer2 search program (R. Durbin et al. (1998) *Biological sequence analysis: probabilistic models of proteins and nucleic acids*. Cambridge University Press). The database also is annotated and monitored. The ProDom protein domain database consists of an automatic compilation of homologous domains (Corpet et al. (1999), *Nucl. Acids Res.* 27:263-267). Current versions of ProDom are built using recursive PSI-BLAST searches (Altschul et al. (1997) *Nucleic Acids Res.* 25:3389-3402; Gouzy et al. (1999) *Computers and Chemistry* 23:333-340) of the SWISS-PROT 38 and TREMBL protein databases. The database automatically generates a consensus sequence for each domain. Prosite lists the Kunitz domain as a motif and identifies proteins that include a Kunitz domain. See, e.g., Falquet et al. Nucleic Acids Res. 30:235-238 (2002).

Kunitz domains interact with target protease using, primarily, amino acids in two loop regions ("binding loops"). The first loop region is between about residues corresponding to amino acids 13-20 of BPTI. The second loop region is between about residues corresponding to amino acids 31-39 of BPTI. An exemplary library of Kunitz domains varies one or more amino acid positions in the first and/or second loop regions. Particularly useful positions to vary, when screening for Kunitz domains that interact with kallikrein or when selecting for improved affinity variants, include: positions 13, 15, 16, 17, 18, 19, 31, 32, 34, and 39 with respect to the sequence of BPTI. At least some of these positions are expected to be in close contact with the target protease. It is also useful to vary other positions, e.g., positions that are adjacent to the aforementioned positions in the three-dimensional structure.

The "framework region" of a Kunitz domain is defined as those residues that are a part of the Kunitz domain, but specifically excluding residues in the first and second binding loops regions, i.e., about residues corresponding to amino acids 13-20 of BPTI and 31-39 of BPTI. Conversely, residues that are not in the binding loop may tolerate a wider range of amino acid substitution (e.g., conservative and/or non-conservative substitutions).

In one embodiment, these Kunitz domains are variant forms of the looped structure including Kunitz domain 1 of human lipoprotein-associated coagulation inhibitor (LACI) protein. LACI contains three internal, well-defined, peptide loop structures that are paradigm Kunitz domains (Girard, T. et al., 1989. Nature, 338:518-520). Variants of Kunitz domain 1 of LACI described herein have been screened, isolated and bind kallikrein with enhanced affinity and specificity (see, for example, U.S. Pat. Nos. 5,795,865 and 6,057,287). These methods can also be applied to other Kunitz domain frameworks to obtain other Kunitz domains that interact with kallikrein, e.g., plasma kallikrein. Useful modulators of kallikrein function typically bind and/or inhibit kallikrein, as determined using kallikrein binding and inhibition assays.

In some aspects, a kallikrein binding agent (e.g., binding protein, e.g., polypeptide, e.g., inhibitory polypeptides, e.g., antibody, e.g., inhibitory antibody, or other binding agent, e.g., small molecule) binds to the active form of plasma kallikrein. In some embodiments, the kallikrein binding agent, binds to and inhibits plasma kallikrein, e.g., human plasma kallikrein and/or murine kallikrein.

Plasma kallikrein binding proteins can be full-length (e.g., an IgG (e.g., an IgG1, IgG2, IgG3, IgG4), IgM, IgA (e.g., IgA1, IgA2), IgD, and IgE) or can include only an antigen-binding fragment (e.g., a Fab, F(ab')2 or scFv fragment). The binding protein can include two heavy chain immunoglobulins and two light chain immunoglobulins, or can be a single chain antibody. Plasma kallikrein binding proteins can be recombinant proteins such as humanized, CDR grafted, chimeric, deimmunized, or in vitro generated antibodies, and may optionally include constant regions derived from human germline immunoglobulin sequences. In one embodiment, the plasma kallikrein binding protein is a monoclonal antibody.

In some embodiments, the kallikrein binding protein binds to and inhibits plasma kallikrein, e.g., human plasma kallikrein and/or murine kallikrein. Exemplary plasma kallikrein binding proteins are disclosed in U.S. Publication No. 20120201756, the entire contents of which are incorporated herein by reference. In some embodiments, the kallikrein binding protein is an antibody (e.g., a human antibody) having the light and/or heavy chains of antibodies selected from the group consisting of M162-A04, M160-G12, M142-H08, X63-G06, X101-A01 (also referred to herein as DX-2922), X81-B01, X67-D03, X67-G04, X81-B01, X67-D03, X67-G04, X115-B07, X115-D05, X115-E09, X115-H06, X115-A03, X115-D01, X115-F02, X124-G01 (also referred to herein as DX-2930), X115-G04, M29-D09, M145-D11, M06-D09 and M35-G04. In some embodiments, the plasma kallikrein binding protein competes with or binds the same epitope as M162-A04, M160-G12, M142-H08, X63-G06, X101-A01 (also referred to herein as DX-2922), X81-B01, X67-D03, X67-G04, X81-B01, X67-D03, X67-G04, X115-B07, X115-D05, X115-E09, X115-H06, X115-A03, X115-D01, X115-F02, X124-G01 (also referred to herein as DX-2930), X115-G04, M29-D09, M145-D11, M06-D09 and M35-G04. In some embodiments, the plasma kallikrein binding protein is DX-2930. See US 20110200611 and US 20120201756, which are incorporated by reference herein.

In some aspects, a kallikrein binding polypeptide (e.g., inhibitory polypeptide) that binds to the active form of plasma kallikrein. Exemplary polypeptide plasma kallikrein agents are disclosed in U.S. Pat. No. 5,795,865, U.S. Pat. No. 5,994,125, U.S. Pat. No. 6,057,287, U.S. Pat. No. 6,333,402, U.S. Pat. No. 7,628,983, and U.S. Pat. No. 8,283,321, U.S. Pat. No. 7,064,107, U.S. Pat. No. 7,276,480, U.S. Pat. No. 7,851,442, U.S. Pat. No. 8,124,586, U.S. Pat. No. 7,811,991, and U.S. Publication No. 20110086801, the entire contents of each of which is incorporated herein by reference. In some embodiments, the kallikrein binding polypeptide is DX-88 (a non-naturally occurring kallikrein inhibitor, also known as KALBITOR® (ecallantide), SEQ ID NO:3). In some embodiments, the kallikrein inhibitor comprises or consists of an about 58-amino acid sequence of amino acids 3-60 of SEQ ID NO:3 or the DX-88 polypeptide having the 60-amino acid sequence of SEQ ID NO:3.

```
                                      (SEQ ID NO: 3)
Glu Ala Met His Ser Phe Cys Ala Phe Lys Ala Asp

Asp Gly Pro Cys Arg Ala Ala His Pro Arg Trp Phe

Phe Asn Ile Phe Thr Arg Gln Cys Glu Glu Phe Ile

Tyr Gly Gly Cys Glu Gly Asn Gln Asn Arg Phe Glu

Ser Leu Glu Glu Cys Lys Lys Met Cys Thr Arg Asp
```

In some embodiments, the plasma kallikrein binding protein is EPIKAL-2 (SEQ ID NO:4), which is a non-naturally occurring kallikrein inhibitor having a 58 residue amino acid sequence (corresponding to residues 3-60 of SEQ ID NO:3) and having amino acid substitutions of Ile to Ser at residue 34 and Glu to Gly at residue 39. The sequence of EPIKAL-2 is shown below:

```
EpiKal2:
                                      (SEQ ID NO: 4)
Met His Ser Phe Cys Ala Phe Lys Ala Asp Asp Gly

Pro Cys Arg Ala Ala His Pro Arg Trp Phe Phe Asn

Ile Phe Thr Arg Gln Cys Glu Glu Phe Ser Tyr Gly

Gly Cys Gly Gly Asn Gln Asn Arg Phe Glu Ser Leu

Glu Glu Cys Lys Lys Met Cys Thr Arg Asp
```

In some embodiments, a plasma kallikrein binding protein can have about 85%, 90%, 91%, 92%, 93%, 94%, 95%, 96%, 97%, 98%, 99% or higher sequence identity to a binding protein described herein. In some embodiments, a plasma kallikrein binding protein can have about 85%, 90%, 91%, 92%, 93%, 94%, 95%, 96%, 97%, 98%, 99% or higher sequence identity in the HC and/or LC framework regions (e.g., HC and/or LC FR 1, 2, 3, and/or 4) to a binding protein described herein. In some embodiments, a plasma kallikrein binding protein can have about 85%, 90%, 91%, 92%, 93%, 94%, 95%, 96%, 97%, 98%, 99% or higher sequence identity in the HC and/or LC CDRs (e.g., HC and/or LC CDR1, 2, and/or 3) to a binding protein described herein. In some embodiments, a plasma kallikrein binding protein can have about 85%, 90%, 91%, 92%, 93%, 94%, 95%, 96%, 97%, 98%, 99% or higher sequence identity in the constant region (e.g., CH1, CH2, CH3, and/or CL1) to a binding protein described herein.

In some aspects, a small molecule binds to the active form of plasma kallikrein.

Bradykinin B2 Receptor Antagonists

In some embodiments, a bradykinin B2 receptor antagonist is administered to a subject. Exemplary bradykinin B2 receptor antagonists include Incatibant (Firazyr®), which is a peptidomimetic drug containing 10 amino acids which block binding of native bradykinin to the bradykinin B2 receptor.

C1-INH Replacement Agents

In some embodiment, a replacement C1-INH agent is administered to a subject. Exemplary C1-INH replacement agents are publicly available and include, for example, Berinert®, which is a purified human pasteurized nanofiltered C1-INH concentrate.

EXAMPLES

Example 1

Cleaved Kininogen

Based on analysis of the contact system, cleaved kininogen is a suitable biomarker for measuring contact system activation. Cleaved kininogen has been previously shown to be elevated during HAE attacks, in cirrhosis), and as a consequence of contact system activation during sepsis. Antibody phage display libraries were panned against cleaved kininogen in combination with depletion on intact kininogen. In parallel mice were immunized with cleaved kininogen and monoclonal antibodies obtained from hybridoma cell lines. Both efforts provided a number of different monoclonal antibodies that bound both cleaved and intact kininogen but no antibody that only bound cleaved kininogen.

Figure 2:
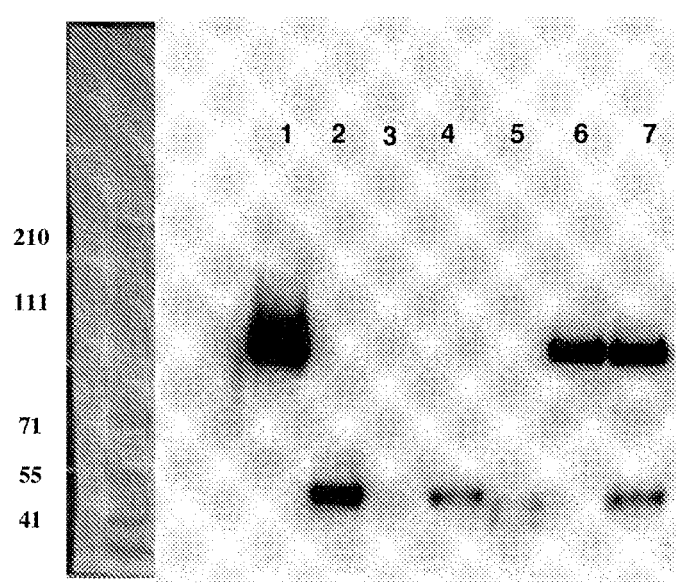
FIG. 2 shows cleaved kininogen detection by Western blot analysis. Samples were analyzed using SDS-PAGE (3-8% Tris-Acetate) under reducing conditions followed by transfer to PVDF membrane and immunoblotting. Lane 1—50 nM Intact Kininogen; Lane 2—50 nM Cleaved Kininogen; Lane 3—50 nM Low Molecular Weight Kininogen; Lane 4—L:20 Sodium Citrated Human Plasma (Glass Collection Tube); Lane 5—1:20 Sodium Citrated Human Plasma (Plastic) Kallikrein Treated; Lane 6—1:20 Sodium Citrated Human Plasma (Plastic); Lane 7—1:20 Sodium Citrated Human Plasma (Plastic) 20 nM 2 Chain Kininogen Added.

A number of the antibodies were screened for suitability in a Western blot assay and several identified that work well including the mouse mAb (clone 11H05) shown in FIG. 2. It is evident that this assay is capable of detecting cleaved kininogen in human plasma samples. Furthermore, the data in FIG. 2 confirms that plasma collection in glass is sufficient to prevent contact activation and kininogen cleavage.

Mass spectrometry based approach can also be used detect cleaved kininogen in patient plasma. In this approach, one immune adsorbs kininogen from the patient sample, proteolytically digests the eluted kininogen and analyzes peptide fragments by LC-MC.

Example 2

Immunoassays for C1INH-pKal and α2M-pKal

ELISA-based immunoassays have been developed for the detection of these complexes. The sandwich based ELISA assays are similar to that previously described, see, e.g., Kaufman, et al., Blood 77, 2660-2667, and Wachtfogel, Blood 73, 468-471.

Example 3

C1INH-pKal Assay

Figure 3:
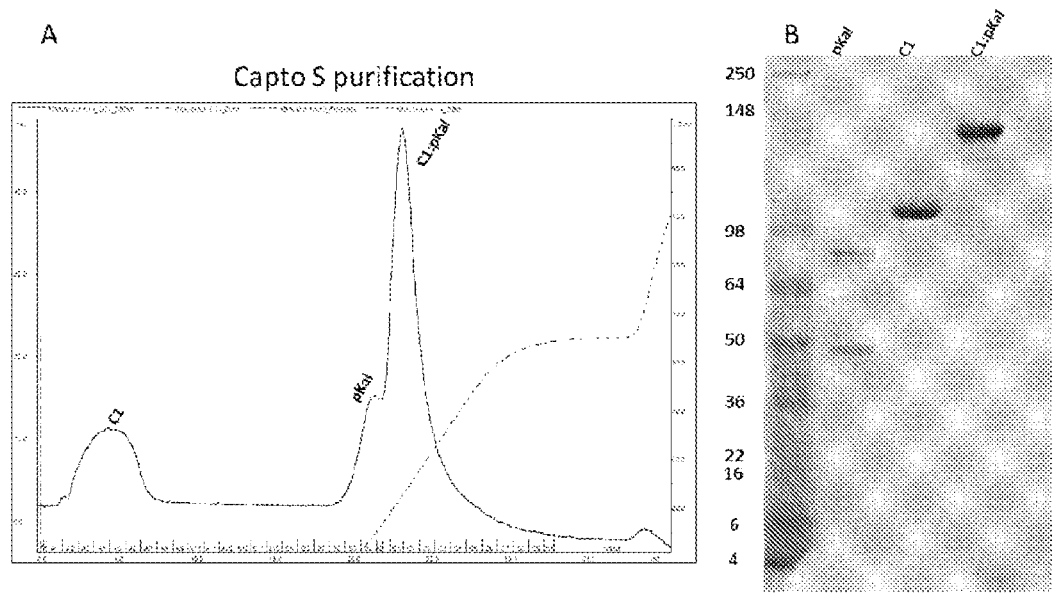
FIG. 3 shows the purification of C1INH-pKal complex. The cation exchange chromatogram (panel A) demonstrates separation of the C1INH, pKal and the complex. The fractions from the cation exchange were collected and analyzed by SDS-PAGE (panel B).

An ELISA has been developed for the detection of the C1INH-pKal complex. This sandwich assay uses antibodies against pKal and C1INH as either the capture or detection reagent. A first step in the development of this assay is the preparation of the C1INH-pKal complex. This covalent complex was prepared by incubating a 2-4 fold molar excess of pKal over C1INH. The complex was then purified using cation exchange chromatography (Capto S resin) as shown in FIG. 3. The complex was quantified using a calculated molar extinction coefficient at 280 nm (121, 740 $M^{-1}$ $cm^{-1}$). Previous reports that used similar assays to measure C1INH-pKal did not report a extinction coefficient. Accurate determination of concentration is critical because for an assay to determine how much pKal is activated during disease, which informs drug dosing.

Figure 4:
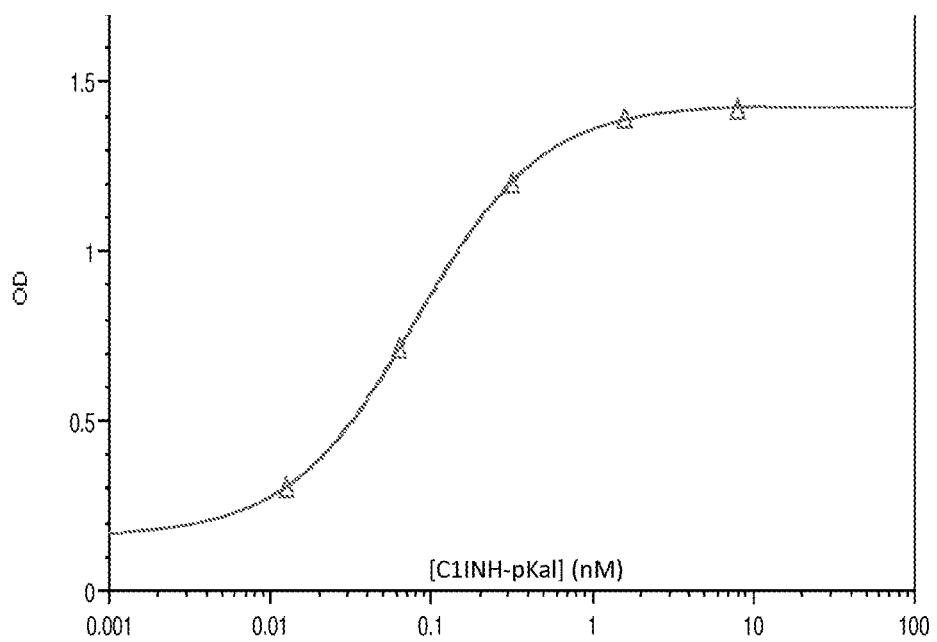
FIG. 4 shows a sandwich ELISA standard curve for C1INH-pKal detection in human plasma. Mouse anti-pKal (clone 13G11) was plated and goat Anti-C1 Inhibitor was used for detection.
Figure 5:
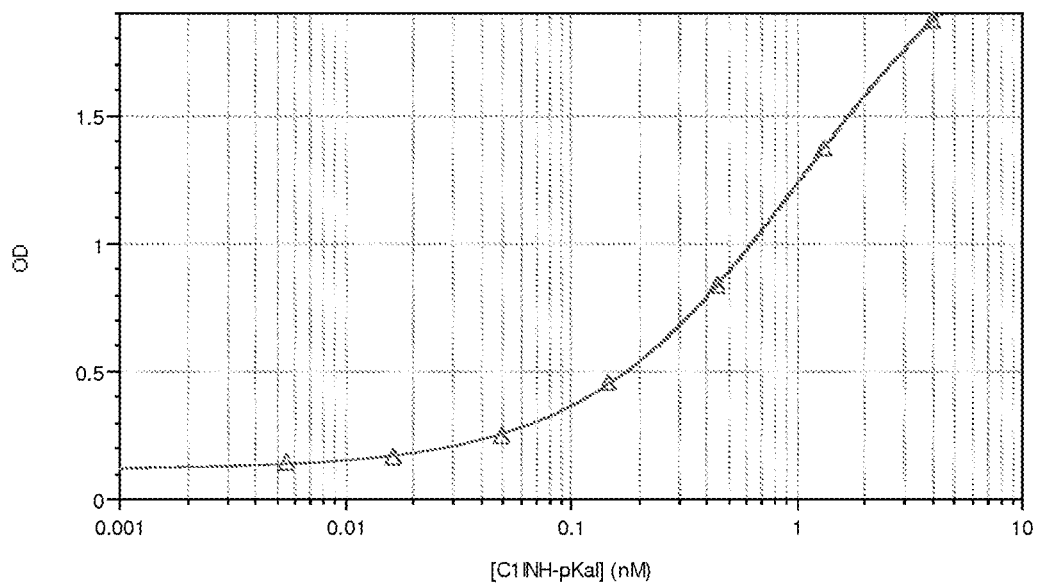
FIG. 5 shows a sandwich ELISA standard curve for C1INH-pKal detection in human plasma. Goat Anti-C1-INH was plated and mouse anti-pKal (clone 13G11) was used for detection.

Two assay formats for the detection of C1INH-pKal by ELISA were investigated. The first format uses an anti-pKal antibody (mouse mAb 13G11) as the capture reagent and an antibody against C1INH as the detection antibody following signal production with an HRP-labeled secondary antibody (FIG. 4). This assay has a lower limit of quantitation in the single digit nanomolar range or below. The opposite assay format was also investigated, in which anti-C1INH is the capture antibody and anti-pKal (13G11) is the detection antibody (FIG. 5). This assay format has a similar lower limit of quantitation. Having two assay formats provides additional options to multiplex assays for C1INH-pKal and α2M-pKal.

Example 4

α2M-pKal Complex Assay

Figure 6:
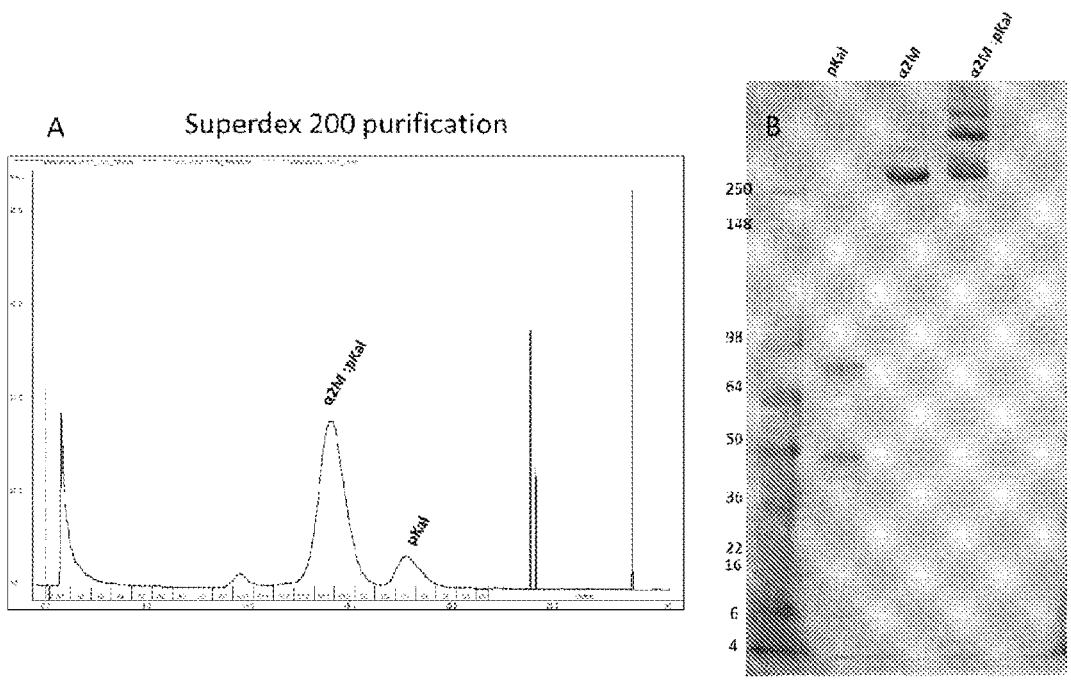
FIG. 6 shows the purification of α2M-pKal complex. The complex was purified by size exclusion chromatography (panel A) and fractions were analyzed by SDS-PAGE (panel B).
Figure 7:
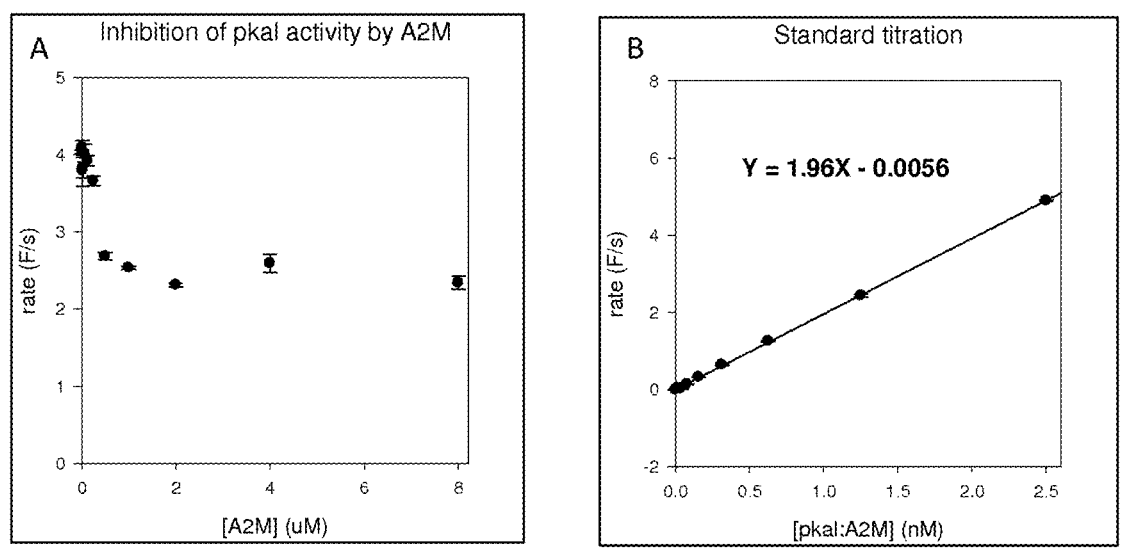
FIG. 7 shows the quantitation of α2M-pKal complex. Plasma kallikrein activity was shown to been decreased to a plateau level upon addition of excess α2M (panel A). Using a 10-fold excess of α2M over pKal as standard curve was constructed, from which the molar concentration of our purified α2M-pKal complex could be determined according to the concentration of pKal in the complex.

An ELISA was developed for the detection of the α2M-pKal complex. This sandwich assay uses antibodies against pKal and α2M as either the capture or detection reagent. A first step in the development of this assay is the preparation of the α2M-pKal complex. This covalent complex was prepared by incubating a 2-4 fold molar excess of pKal over α2M. The complex was then purified using size exclusion chromatography as shown in FIG. 6. α2M is composed of ~180 kDa subunits that exists as a distribution of oligomers up to tetramers. Upon interaction with pKal, each monomer of α2M has a propensity to form a covalent amide bond via hydrolysis of thioester bonds in α2M by lysine amines on pKal. Consequently, a distribution of cross-linked species can be expected, which complicates quantitation. A method was derived to quantify the α2M-pKal complex by measuring the activity of the complex and converting to a concentration using a standard curve (FIG. 7). This quantitation method is possible because it is well known in the literature that covalent complexes of α2M with target proteases do not block the active site towards small synthetic peptide substrates.

Figure 8:
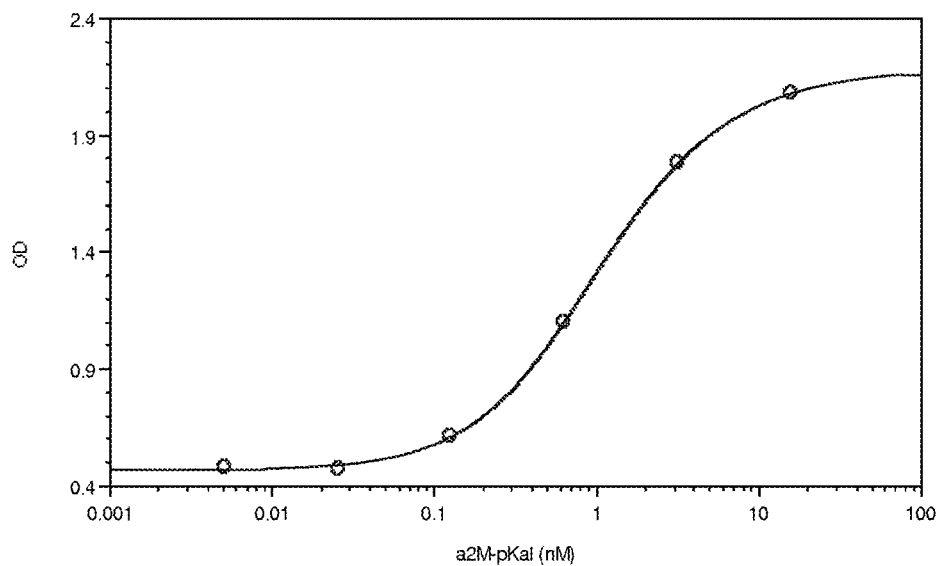
FIG. 8 shows sandwich ELISA standard curve for α2M-pKal detection in human plasma. Anti-α2M was plated and mouse anti-pKal (clone 13G11) was used for detection
Figure 9:
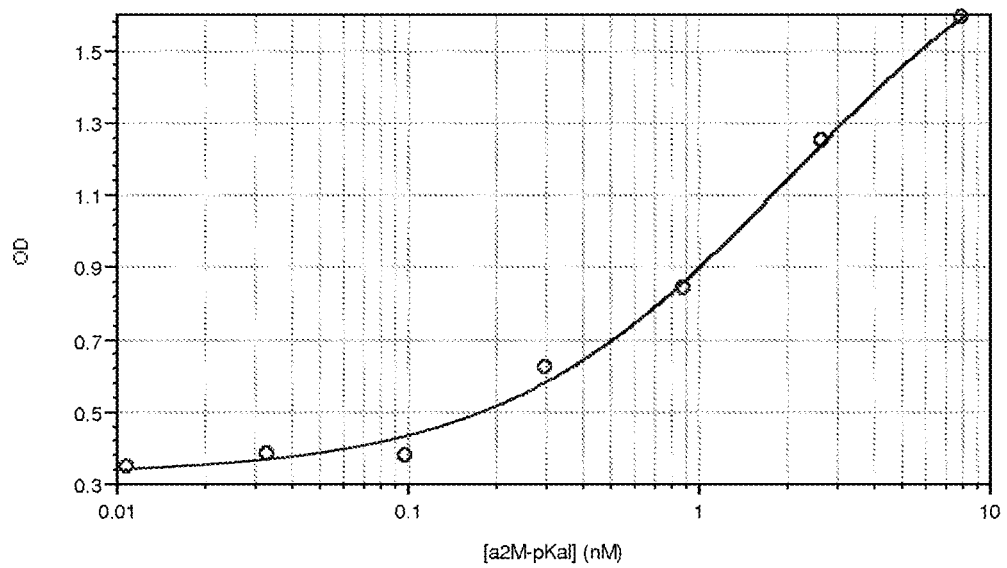
FIG. 9 shows sandwich ELISA standard curve for α2M-pKal detection in human plasma. Anti-pKal (clone 13G11) was plated and anti-α2M was used for detection.

As with the C1INH-pKal assay, two assay formats were investigated for the detection of α2M-pKal by ELISA. The first format uses an anti-pKal antibody (mouse mAb 13G11) as the capture reagent and an antibody against α2M as the detection antibody following signal production with an HRP-labeled secondary antibody (FIG. 8). This assay format has a lower limit of quantitation in the single digit nanomolar range or below. The opposite assay format was also investigated, in which anti-α2M is the capture antibody and anti-pKal (13G11) is the detection antibody (FIG. 9). This assay format has a similar lower limit of quantitation. Having two assay formats provides additional options as we look to multiplex assays for C1INH-pKal and α2M-pKal.

Example 5

Detection of α2M-pKal and C1INH-pKal in Activated Plasma

Figure 10:
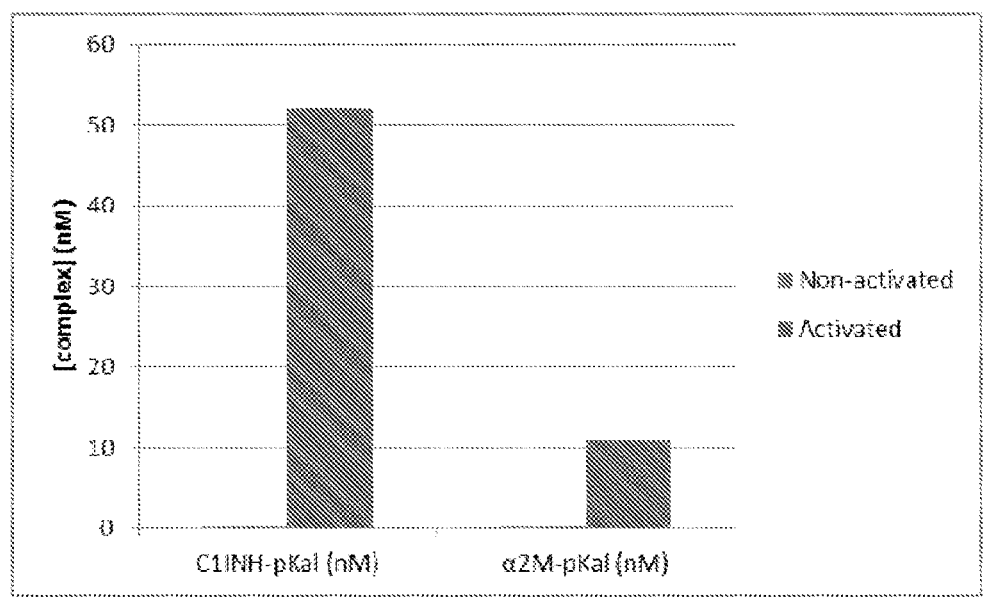
FIG. 10 shows detection of C1INH-pKal and α2M-pKal complexes in normal human plasma following activation with dextran sulfate.

ELISAs were used to detect pKal activation in normal human plasma treated with reagents, such as kaolin or dextran sulfate, which are known to induce contact activation. As shown in FIG. 10, the assays can detect the complexes that are formed in plasma following in vitro activation with dextran sulfate.

Example 6

Intact and Cleaved Kininogen

Figure 11:
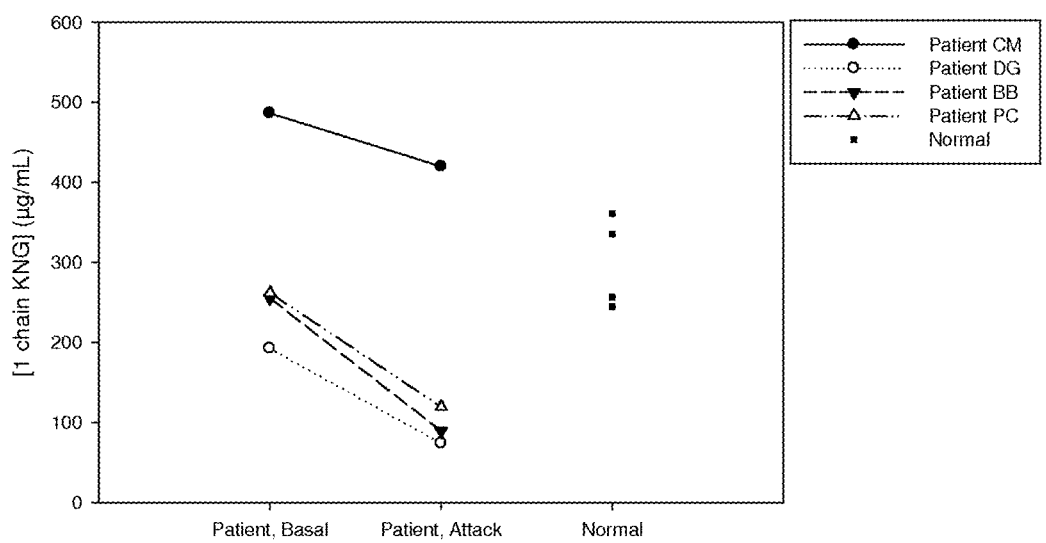
FIG. 11 shows detection of intact kininogen (i.e., 1-chain) in a patient sample obtained during an attack. Patient plasma sample was collected in citrated plasma tubes containing an anti-protease cocktail.
Figure 13:
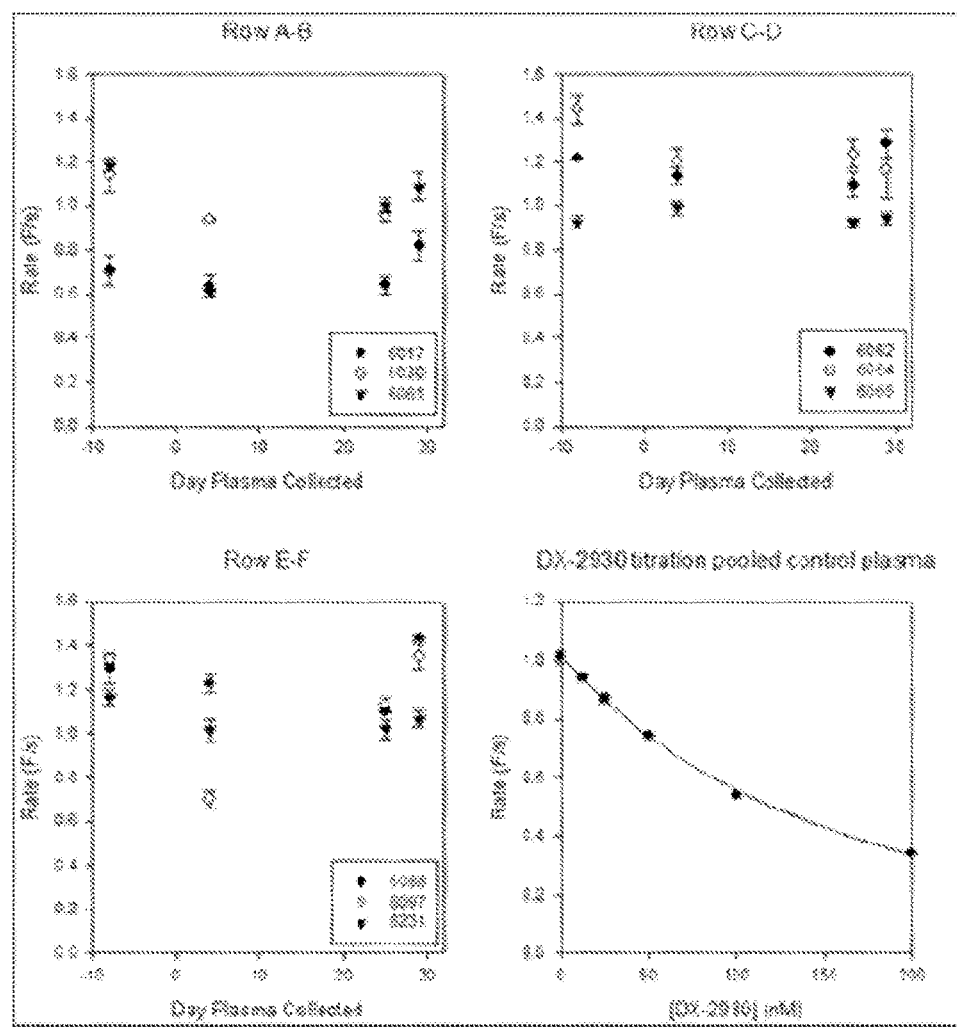
FIG. 13 shows experiments in plasma from placebo/vehicle treated monkeys as well as a DX-2930 control spiked into this same plasma.

Western blot was used to show that plasma from a patient obtained during an attack and collected in citrated plasma tubes containing an anti-protease cocktail exhibits a decrease in amount of intact kininogen (i.e., 1-chain) (FIG. 11). An increase in cleaved kininogen (i.e., 2-chain) was observed (data not shown).

Example 7

Exemplary Assays and Assay Data (i) HMWK Ex Vivo Activation

HMWK Ex Vivo activation assay can be used to evaluating the inhibitory activity of a candidate pKal inhibitor on contact activation. Briefly, FXIIa (e.g., 5 nM) was used to stimulate contact system activation in normal human plasma or simulate HAE attack samples to reduce the level of 1-chain HMWK by around 10-50%, which can be detected Simple Western (SBHD) or Western blot (TGA). Reduced contact activation was observed in DX-2930 treated samples.

As shown in FIG. 17, the inhibitory activity of minimal levels of DX-2930 (e.g., 9-27 nM) was detected in the HMWK Ex Vivo activation assay described herein, using Protein Simple Western or traditional Western blot analysis. The assay condition used in this study can detect the activity of 9-27 nM DX-2930 in 5% plasma. See also Table 2 below:

TABLE 2

Reduction of Plasma Activation by DX-2930

| Sample | MW (kDa) | Area | % Reduction |
|---|---|---|---|
| Normal Human Plasma | 163 | 10643.89 | NA |
| XIIa Activated Plasma - 480 nM DX2930 | 162 | 4799.214 | 54.9 |
| XIIa Activated Plasma - 240 nM DX2930 | 163 | 3843.905 | 63.9 |
| XIIa Activated Plasma - 80 nM DX2930 | 162 | 2234.369 | 79.0 |
| XIIa Activated Plasma - 27 nM DX2930 | 164 | 1025.635 | 90.4 |
| XIIa Activated Plasma - 9 nM DX2930 | 164 | 841.682 | 92.1 |
| XIIa Activated Plasma - 0 nM DX2930 | 165 | 389.155 | 96.3 |

Figure 18:
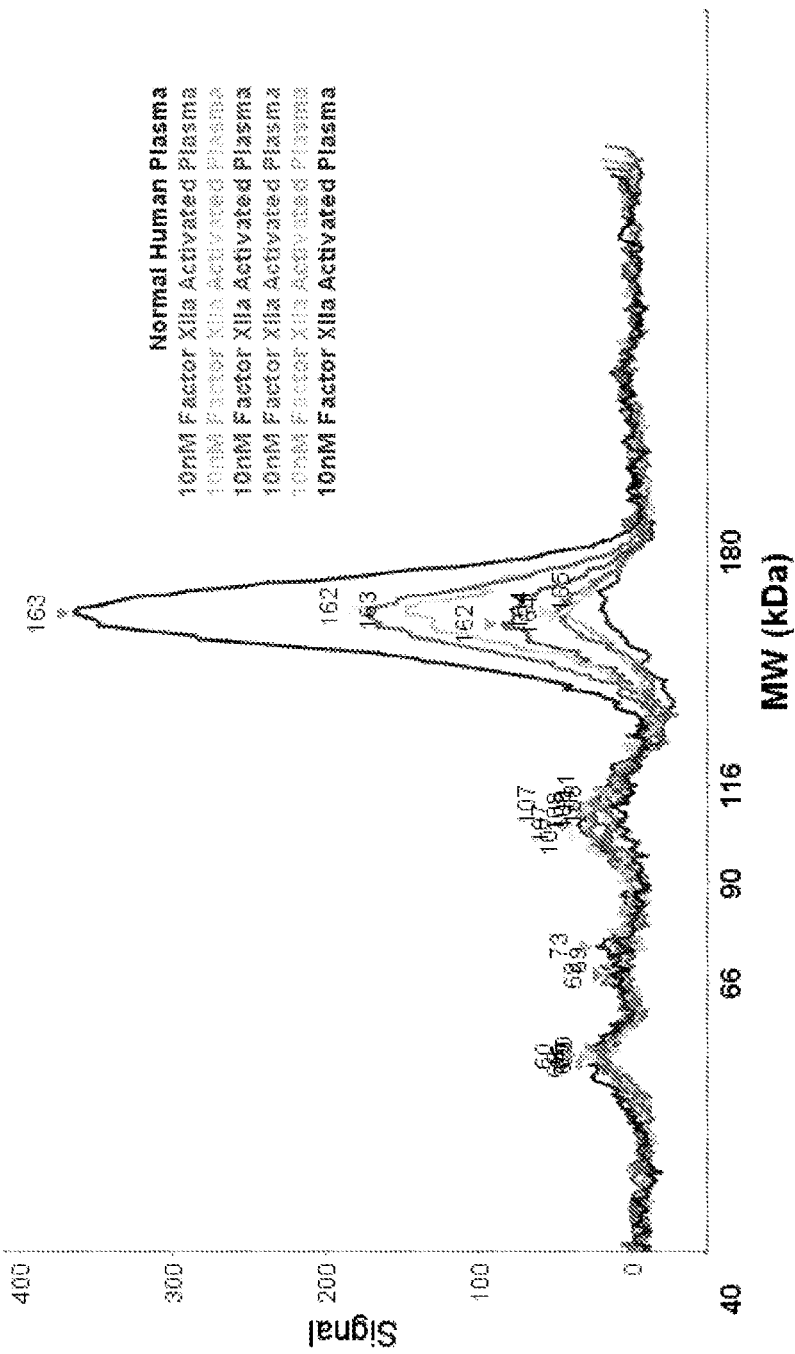
FIG. 18 depicts an HMWK Ex Vivo activation assay showing Protein Simple raw data for Factor XIIa activated plasma with DX2930 titration.

The raw data for Factor XIIa activated plasma with DX-2930 titration was provided in FIG. 18. See also Table 3 below:

TABLE 3

Reduction of Plasma Activation by DX-2930 at Various Concentrations

| Sample | MW (kDa) | Area | % Reduction |
|---|---|---|---|
| Normal Human Plasma | 163 | 10643.9 | NA |
| 480 nM DX2930 | 162 | 4799.2 | 54.9 |
| 240 nM DX2930 | 163 | 3843.9 | 63.9 |
| 80 nM DX2930 | 162 | 2234.4 | 79.0 |
| 27 nM DX2930 | 164 | 1025.6 | 90.4 |
| 9 nM DX2930 | 164 | 841.7 | 92.1 |
| 0 nM DX2930 | 165 | 389.2 | 96.3 |

The reduction of one-chain HMWK was examined in various human neat plasma samples after activation by FXIIa for 30 minutes. The results are shown in FIGS. 22-26. See also Tables 4-8 below:

TABLE 4

% Reduction of One-Chain HMWK After 30 Minutes Action in Neat Plasma Sample BRH745047

| Sample | Peak Area (~160 kDa) | % Reduction |
|---|---|---|
| BRH745047 | 19707 | NA |
| BRH745047 + 5 nM FXIIa | 7464 | 62.1 |
| BRH745047 + 10 nM FXIIa | 2541 | 87.1 |

TABLE 5

% Reduction of One-Chain HMWK After 30 Minutes Action in Neat Plasma Sample BRH745048.

| Sample | Peak Area (~160 kDa) | % Reduction |
|---|---|---|
| BRH745048 | 19850 | NA |
| BRH745048 + 5 nM FXIIa | 11235 | 43.4 |
| BRH745048 + 10 nM FXIIa | 4985 | 74.9 |

TABLE 6

% Reduction of One-Chain HMWK After 30 Minutes Action in Neat Plasma Sample BRH745064

| Sample | Peak Area (~160 kDa) | % Reduction |
|---|---|---|
| BRH745064 | 22916 | NA |
| BRH745064 + 5 nM FXIIa | 15345 | 33.0 |
| BRH745064 + 10 nM FXIIa | 8124 | 64.5 |

TABLE 7

% Reduction of One-Chain HMWK After 30 Minutes Action in Neat Plasma Sample BRH745062

| Sample | Peak Area (~160 kDa) | % Reduction |
|---|---|---|
| BRH745062 | 22086 | NA |
| BRH745062 + 5 nM FXIIa | 7329 | 66.8 |
| BRH745062 + 10 nM FXIIa | 3126 | 85.8 |

TABLE 8

% Reduction of One-Chain HMWK After 30 Minutes Action in Neat Plasma Samples BRH745049, BRH745062, and BRH745063

| Sample | Peak Area (~160 kDa) | Concentration (nM) |
|---|---|---|
| 1 uM 1 Chain HMWK | 37648 | 1000.0 |
| BRH745049 | 21960 | 583.3 |
| BRH745062 | 22086 | 586.6 |
| BRH745063 | 18479 | 490.8 |

Figure 27:
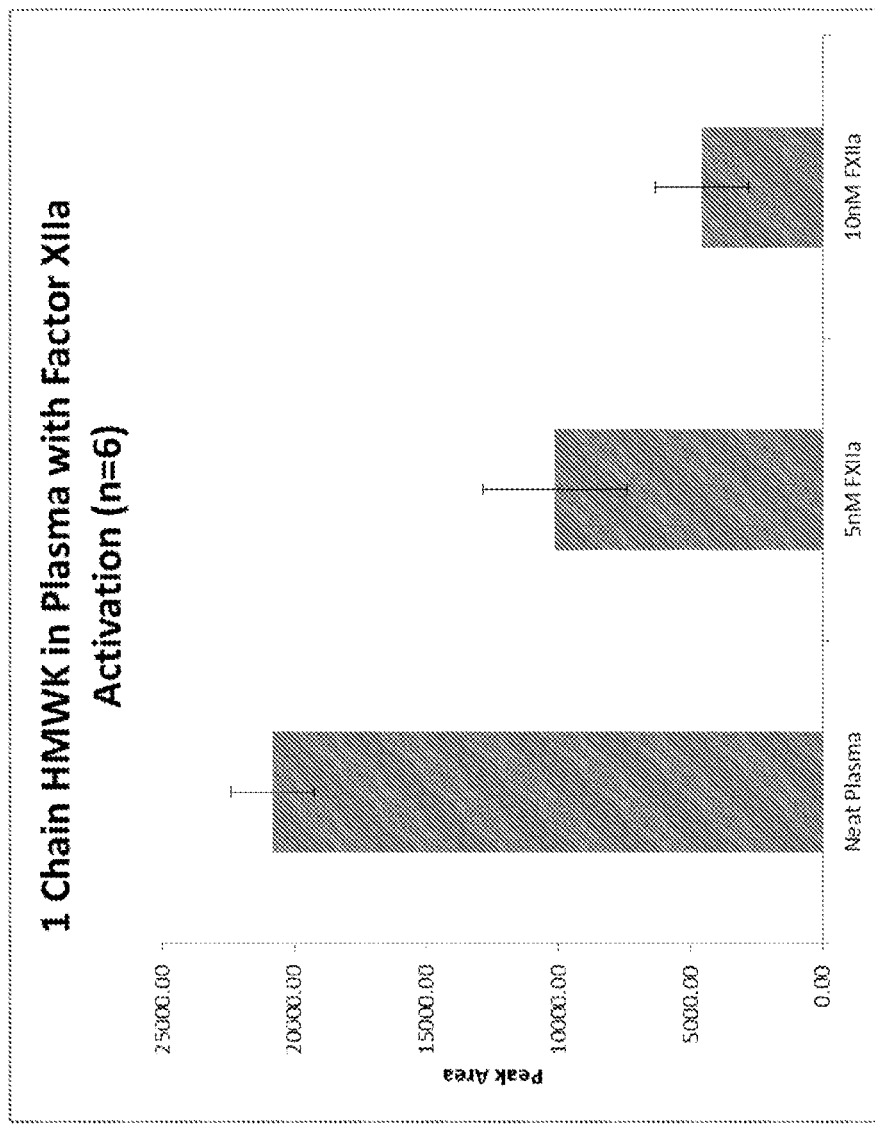
FIG. 27 is a chart showing the reduction of one-chain HMWK in plasma with FXIIa at various concentrations.

As shown in FIG. 27, Factor XIIa activation resulted in the reduction of one-chain HMWK in plasma samples in a dose-dependent manner.

(ii) Endogenous Cleaved Kininogen

In this assay, SCAT tube plasma was analyzed by Simple Western (SBHD) and Western blot (TGA) to determine the level of cleaved Kininogen in the plasma sample. Cleaved HMWK was found to be elevated in basal and attack HAE samples as compared to normal human plasma. It is expected that cleaved HMWK would be reduced in DX-2930 treated HAE patients, as well as in DX-2930-treated healthy volunteers.

Figure 28:
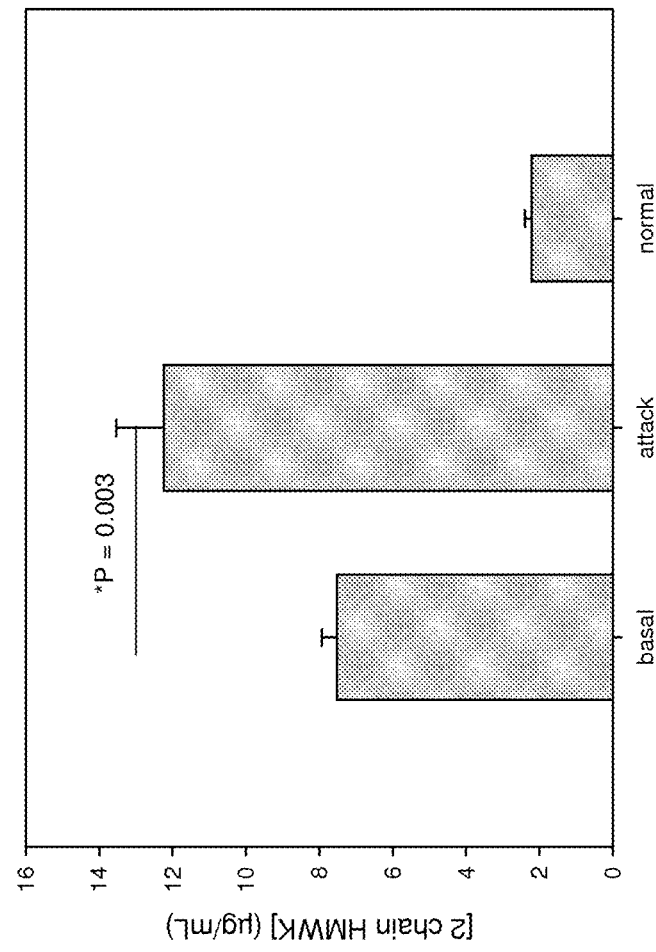
FIG. 28 shows the levels of two-chain HMWK in normal, basal, and HAE attack patients as determined by the endogenous cleaved kininogen assay described herein.

As shown in FIG. 28, levels of two-chain HMWK (cleaved HMWK) in basal HAE patient samples were found to be lower than those in patients having HAE attack. Cleaved HMWK level in DX-2930 treated patients are expected to be similar to those of normal patients.

Figure 29:
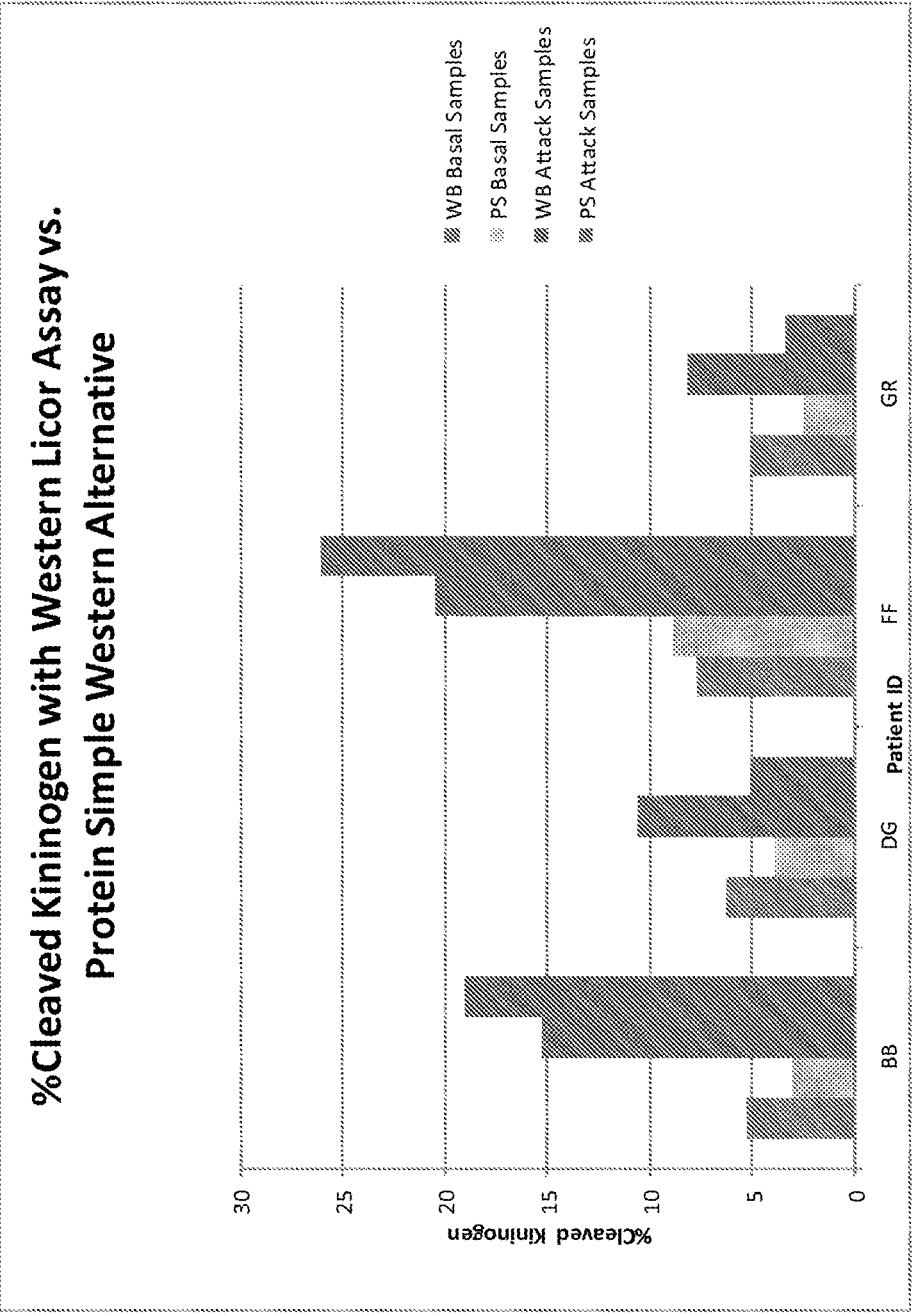
FIG. 29 is a chart showing the endogenous cleaved kininogen in HAE samples as determined by Protein Simple Western blot and traditional Western blot.

FIG. 29 shows the levels of cleaved HMWK in basal and HAE attack patients as determined by Protein Simple Western blot analysis and traditional Western blot analysis.

Figure 30:
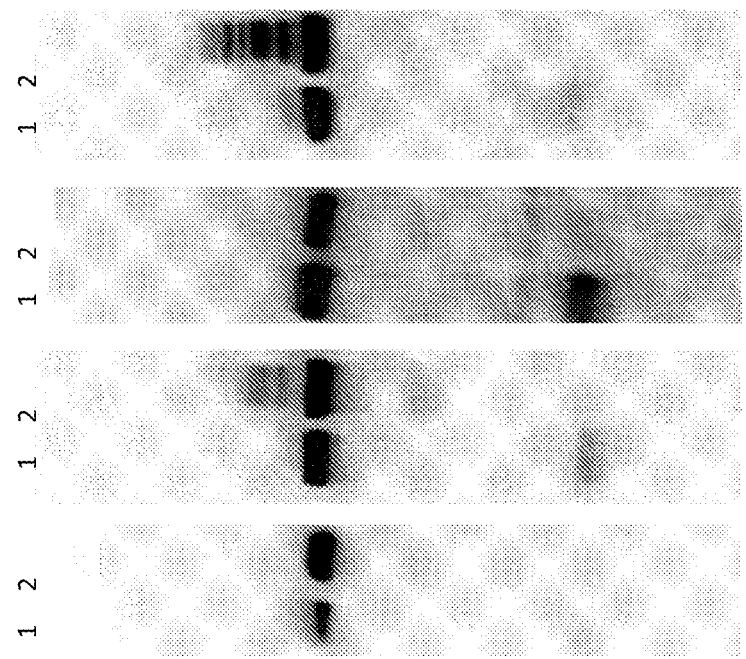
FIG. 30 shows the levels of endogenous cleaved kininogen in samples from HAE patients. Lane 1: purified one-chain and 2-chain HMWK. Lane 2: normal human plasma samples collected with citrate.

Endogenous cleaved HMWK was examined in four individuals. The results are shown in FIG. 30. Low amount of cleaved HMWK was found in normal human plasma samples collected with citrate.

(iii) Ex Vivo Assay for Measuring pKal Activity

This enzyme-based assay was developed to evaluate contact system activation in normal human plasma or simulate HAE attack samples (aim for 10-50% reduction in 1-chain HMWK) and to evaluate the inhibitory activity of pKal inhibitor on contact system activation. Reduced contact activation was observed in DX-2930 treated subjects. This assay is useful in evaluating pKal inhibitor such as DX-2930 bioactivity in treated subjects (e.g., monkeys or human patients).

An example of this assay is illustrated in FIG. 12. Briefly, a plasma sample was placed in a 96-well microplate. Dx-2930, an exemplary pKal inhibitor, FXIIa, an exemplary contact system activator, were added to the plasma sample. The mixture was incubated on ice in the presence of a labeled peptide substrate of pKal for a suitable period of time (e.g., 2 minutes) and corn trypsin inhibitor (CTI) was added to the mixture to stop the activation reaction. The mixture was diluted if necessary and the proteolytic activity was determined by measuring the level of fluorescent peptide substrate.

As shown in FIG. 12, DX-2930-treated monkeys showed reduced levels of contact activation (reduced pKal activity).

(iv) Western Blot Assay for Determining Cleaved HMWK

The level of cleaved HMWK was measured via a Western Blot assay, which can involve LiCor detection. See also Example 8 below. When necessary, citrate or anti-protease cocktail was used as an anti-coagulant in this assay. Elevated cleaved HMWK was observed in HAE samples as compared to normal plasma. This assay is useful in evaluating pKal inhibitor such as DX-2930 bioactivity in treated subjects (e.g., monkeys or human patients).

Figure 14:
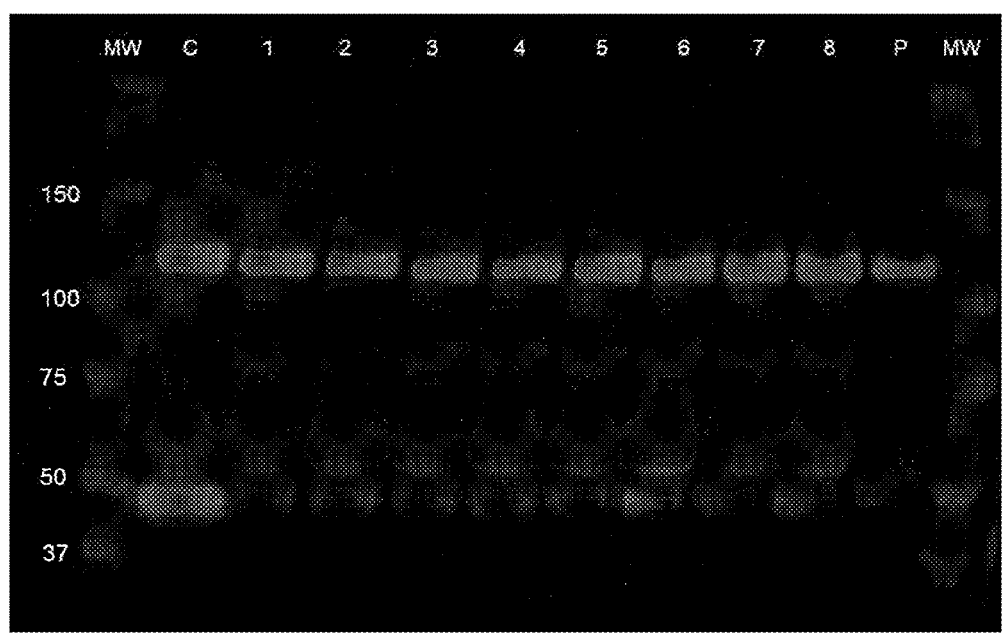
FIG. 14 shows HMWK in plasma samples from HAE patients (CM, DG, BB, and GR). The samples were collected in anti-protease inhibitor cocktail. MW: marker; C: 1 chain (6.44 µg/mL)+2 chain (1.54 µg/mL); 1: CM basal; 2: CM attack; 3: DG basal; 4: DG attack; 5: BB basal; 6: BB attack; 7: GR basal; 8: GR attack; and 9: Pooled normal plasma.
Figure 15:
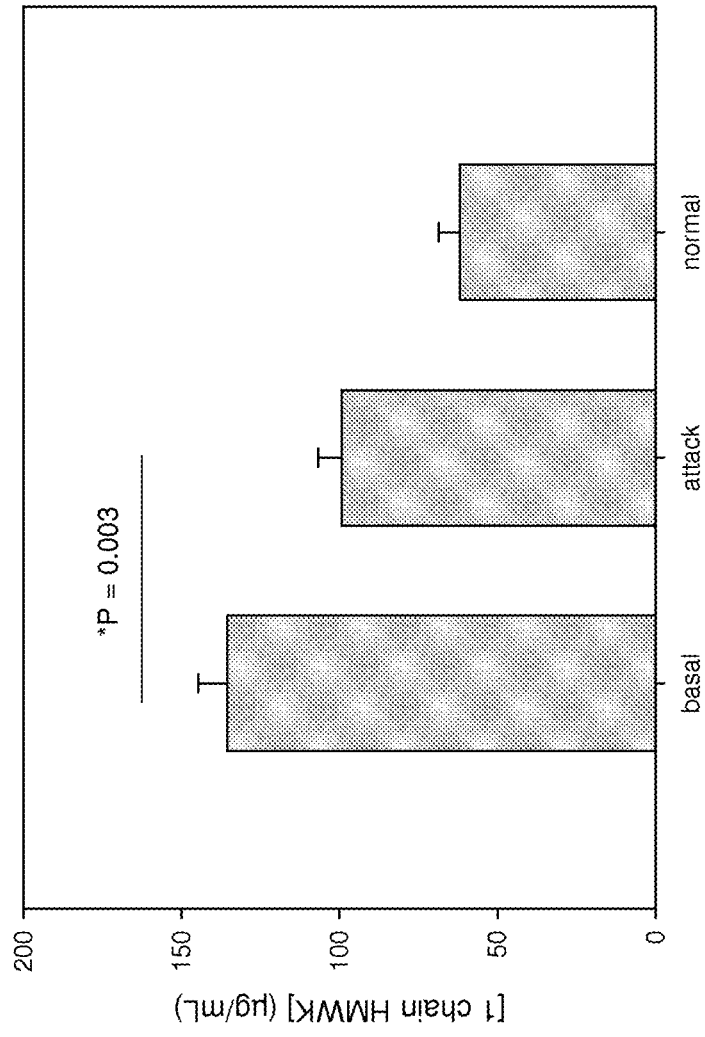
FIG. 15 shows the level of one-chain HMWK in samples from HAE patients as determined by a Western blot assay.
Figure 16:
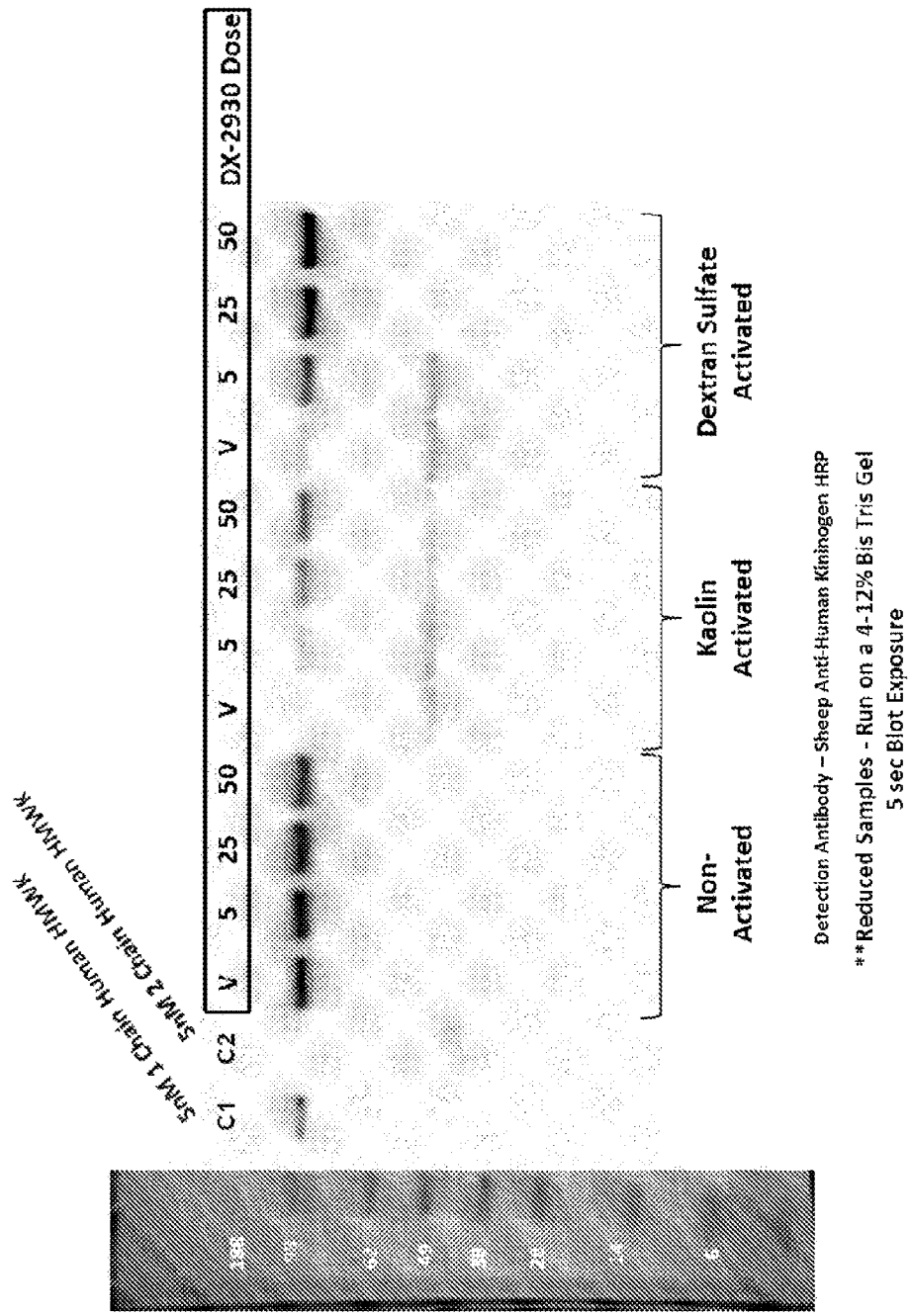
FIG. 16 shows the inhibitory activity of DX-2930 on pKal activation in cynomolgus monkeys. Multi-Dose DX-2930 was used in Cynomolgus Monkeys Kininogen Western Blot Analysis of Day 4 APTT Plasma Samples (With or Without Plasma Activation by Kaolin or 15 µg/mL Dextran Sulfate)

Plasma samples collected from HAE patients in anti-protease inhibitor cocktail were examined using the Western blot assay with LiCor detection and the results were shown in FIG. 14. As shown in FIG. 15, intact kininogen was decreased from 10% (Western blot assay with LiCor detection) to 50% as reported previously. DX-2930 treated cynomolgus monkeys showed reduced levels of pKal activation (by Kaolin or dextran sulfate) in a dose-dependent manner. FIG. 16. See also Table 9 below:

TABLE 9

Reduction of Cleaved HMWK by DX-2930
Day 4 DX-2930 PK Concentration

| Dose Group | Animal ID | Concentration (μg/mL) |
|---|---|---|
| Vehicle | 6097 | BLQ |
| 5 mg/kg | 6010 | 38.56 |

TABLE 9-continued

Reduction of Cleaved HMWK by DX-2930
Day 4 DX-2930 PK Concentration

| Dose Group | Animal ID | Concentration (μg/mL) |
|---|---|---|
| 25 mg/kg | 6070 | 177.42 |
| 50 mg/kg | 6013 | 613.60 |

Figure 19:
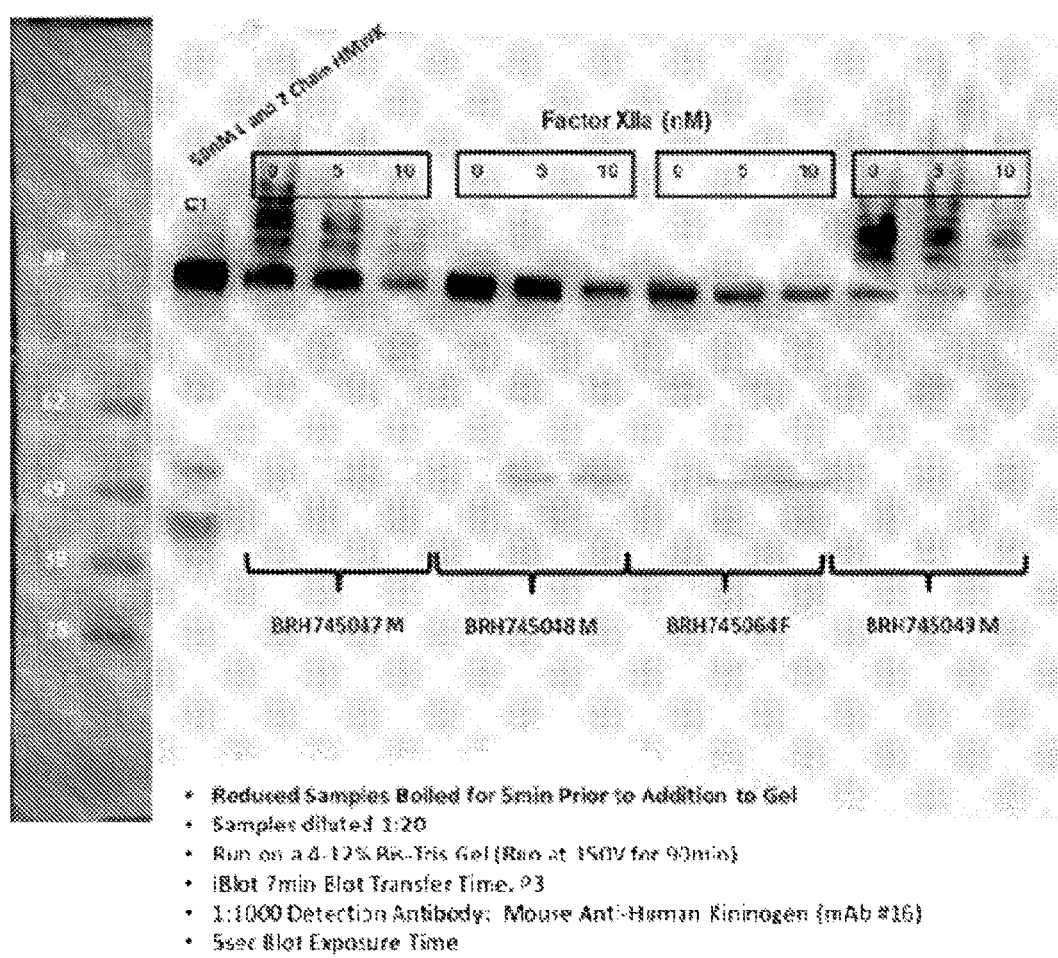
FIG. 19 shows detection of human HMW Kininogen in plasma after 30 minute activation as determined by Western blot analysis.

Human HMWK in various plasma samples after 30-minute activation was shown in FIG. 19 was determined by the Western blot assay described herein. Reduced samples were boiled for 5 minutes prior to addition to gel. The samples were diluted by 20 fold and ran on a 4-12% Bis-Tris Gel at 150 v for 90 minutes. The proteins on the gel were transferred to a membrane using iBlot for 7 minutes. Mouse anti-human kininogen (1:1,000 dilution) was used. The blot exposure time was 5 seconds.

Figure 20:
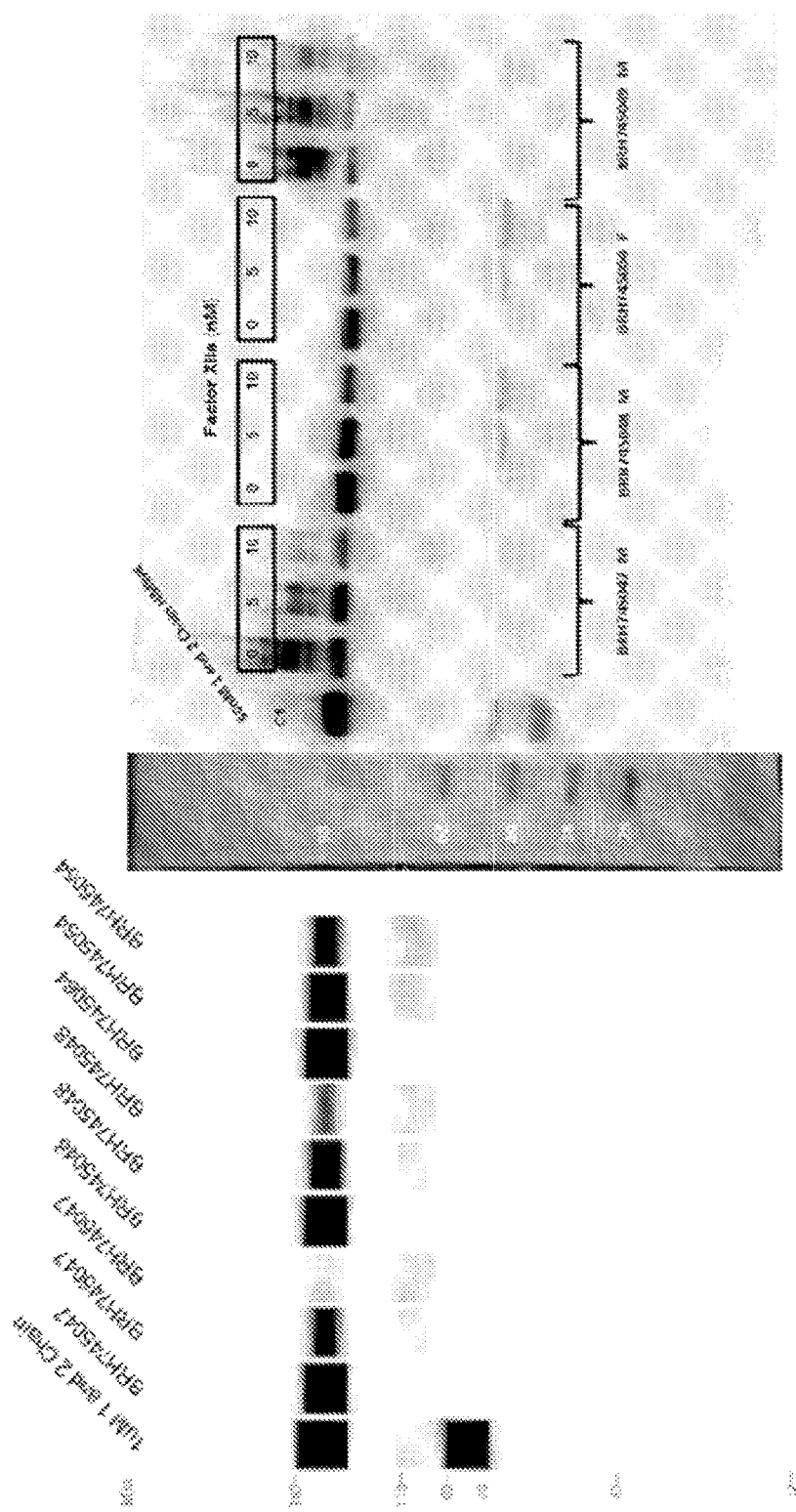
FIG. 20 shows the comparison between Protein Simple Western assay and the traditional Western Blot assay in detecting plasma activation.
Figure 21:
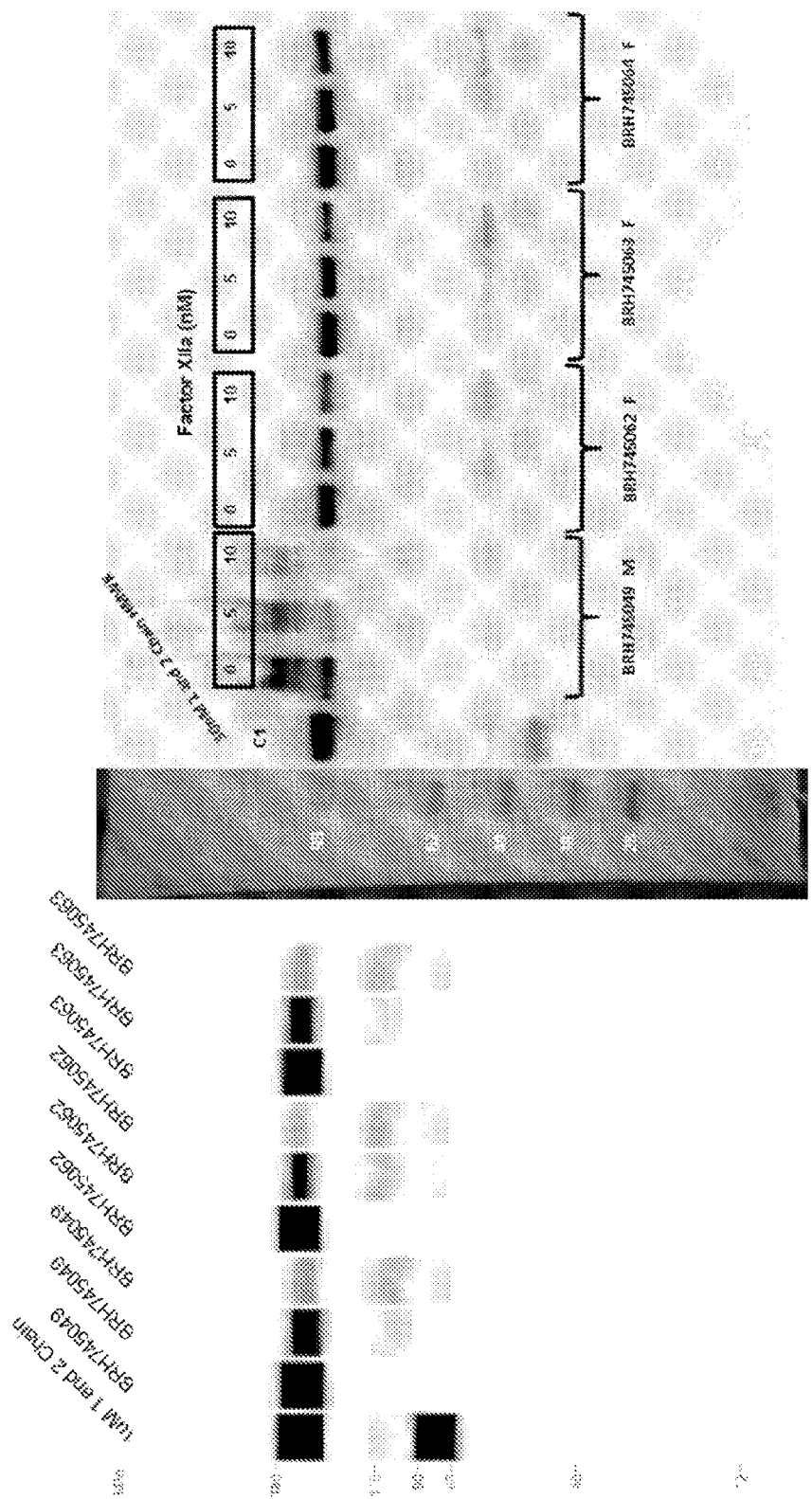
FIG. 21 shows the comparison between Protein Simple Western assay and the traditional Western Blot assay in detecting plasma activation.
Figure 22:
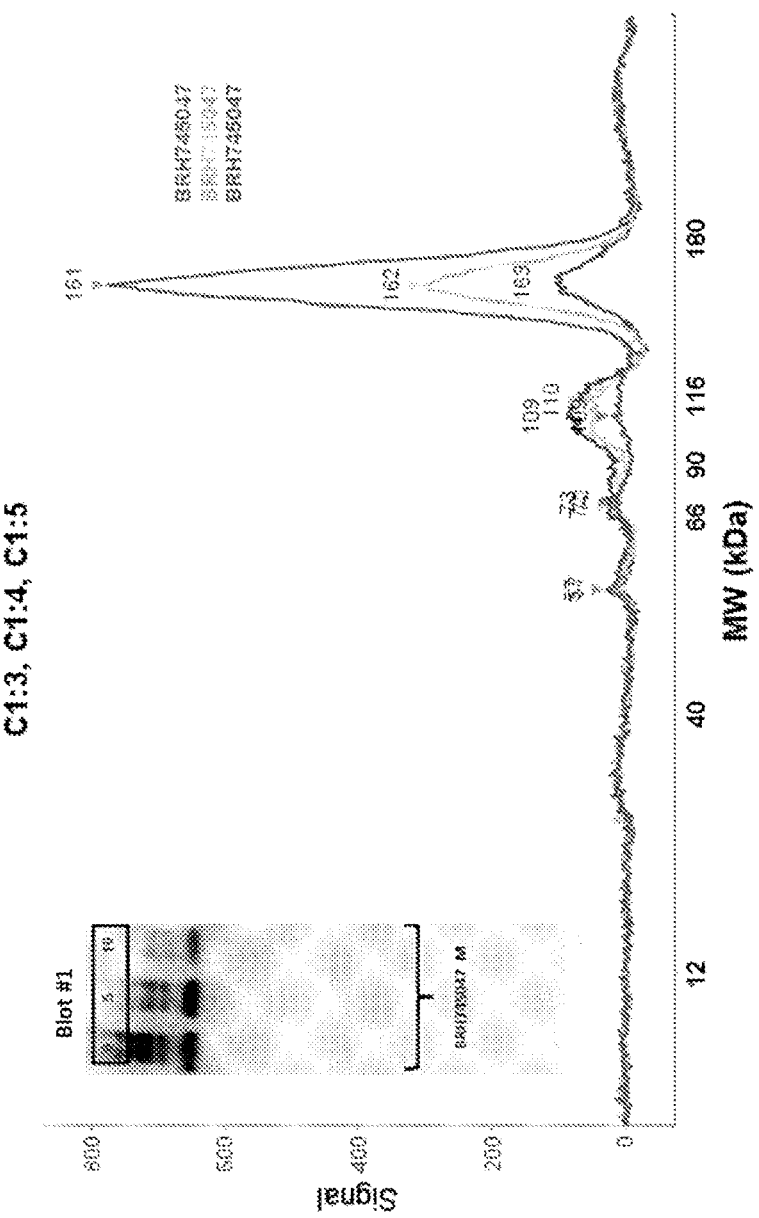
FIG. 22 shows the percentage of reduction of one-chain HMWK after 30 minutes FXIIa activation in neat plasma sample BRH745047.
Figure 23:
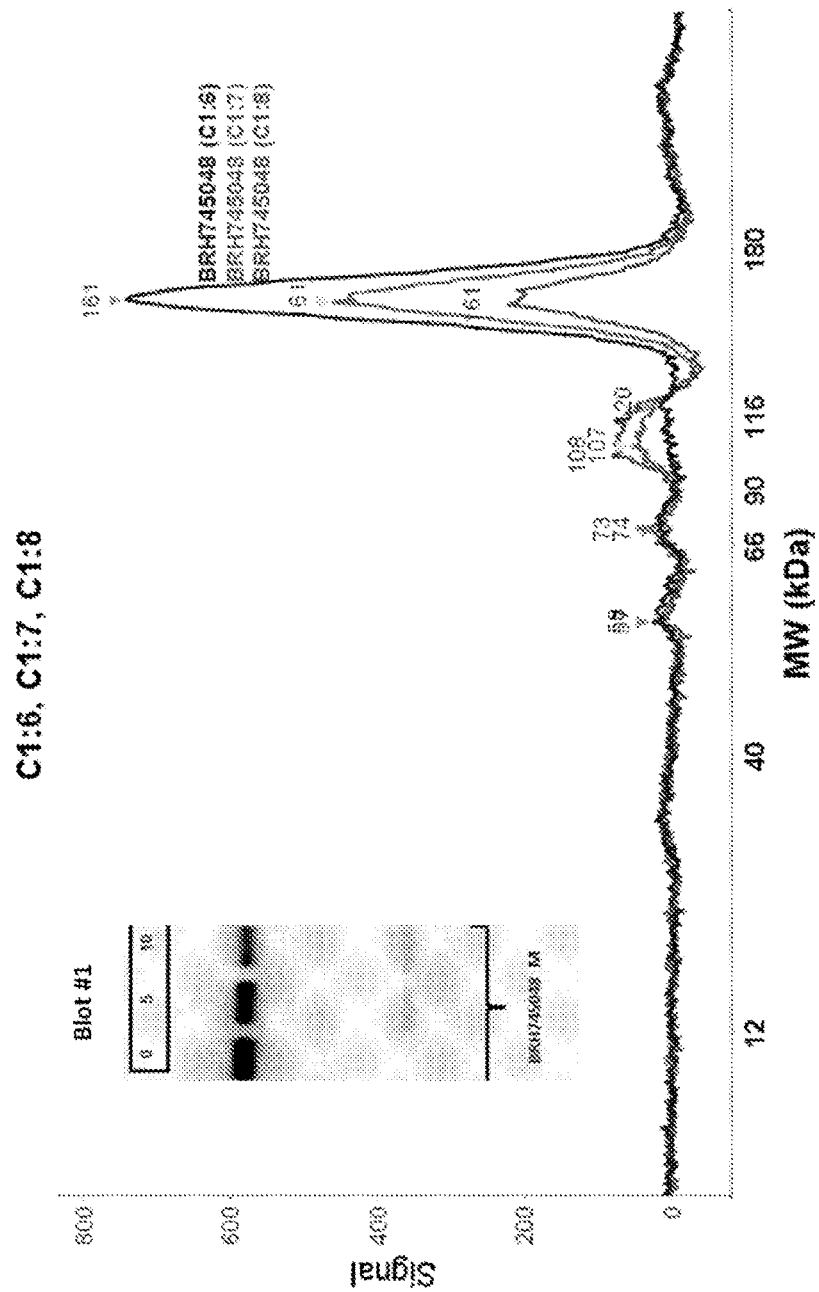
FIG. 23 shows the percentage of reduction of one-chain HMWK after 30 minutes FXIIa activation in neat plasma sample BRH745048.
Figure 24:
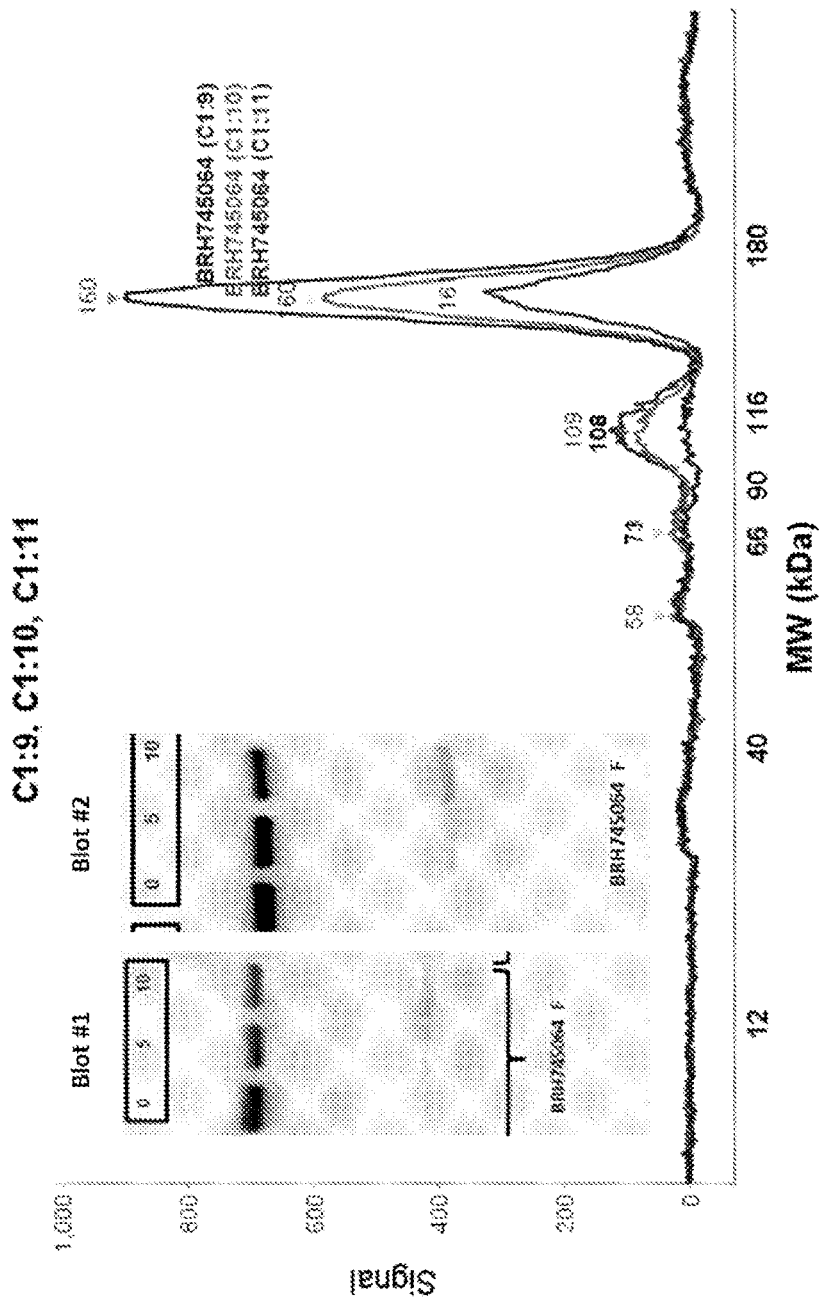
FIG. 24 shows the percentage of reduction of one-chain HMWK after 30 minutes FXIIa activation in neat plasma sample BRH745064.
Figure 25:
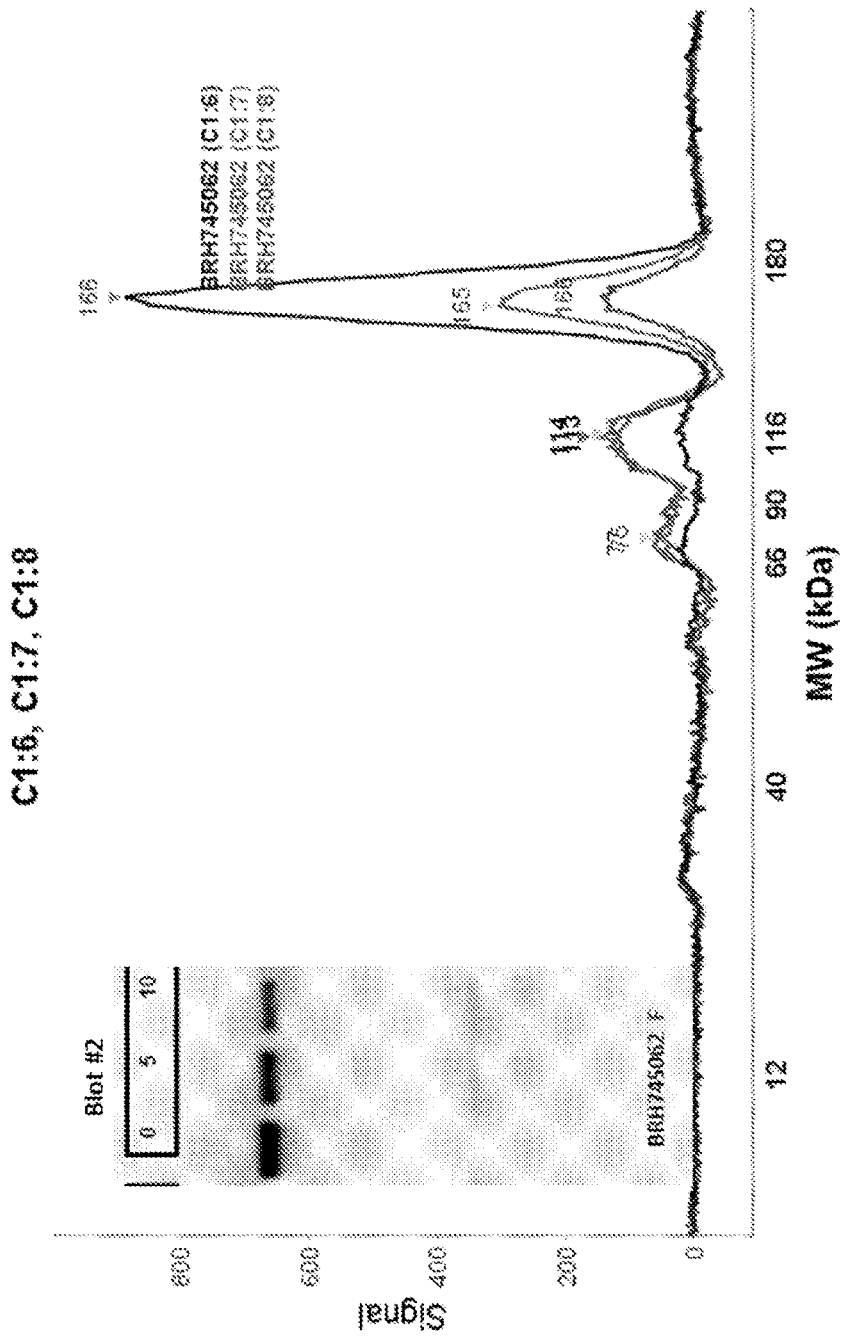
FIG. 25 shows the percentage of reduction of one-chain HMWK after 30 minutes FXIIa activation in neat plasma sample BRH745062.
Figure 26:
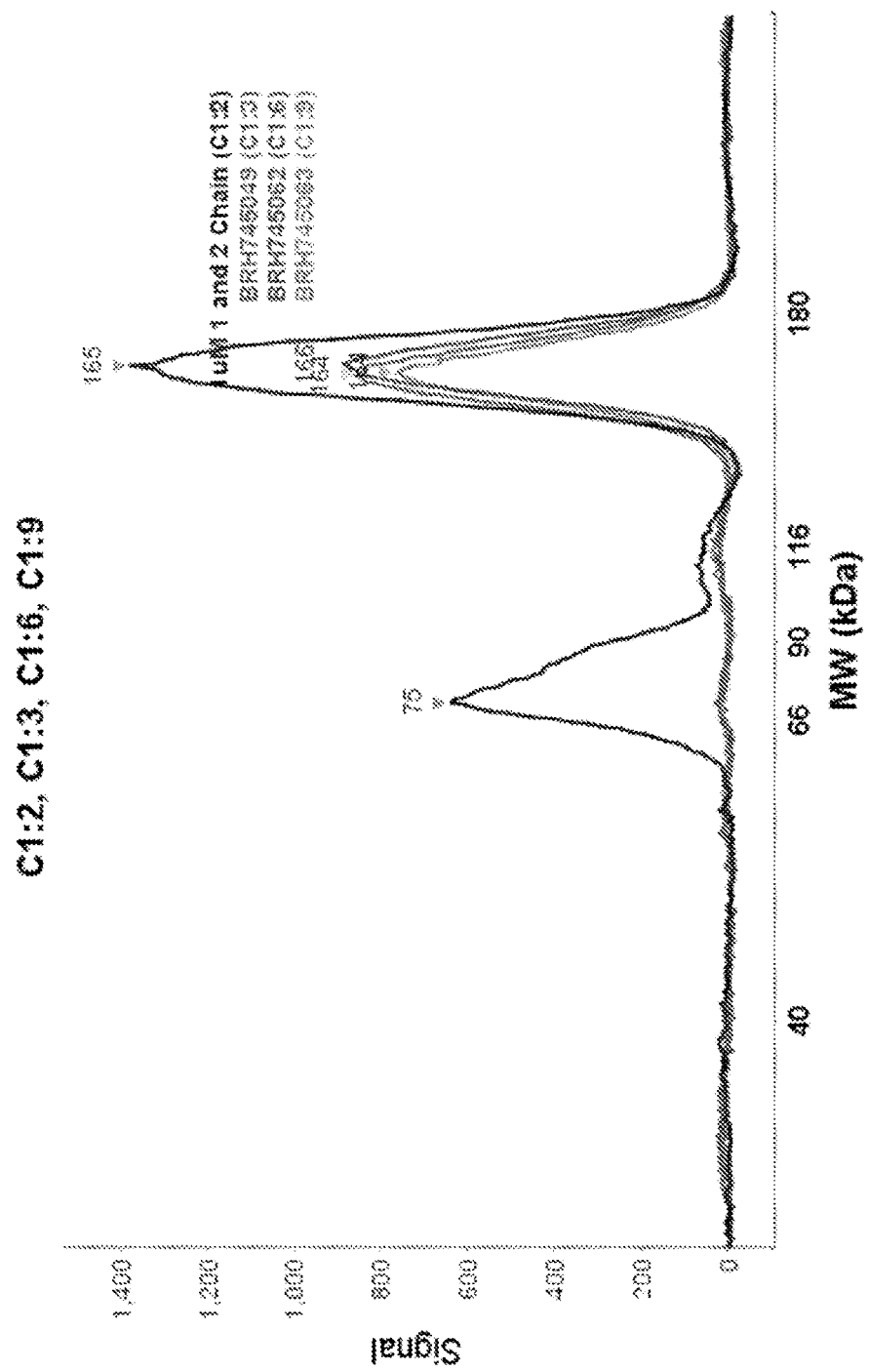
FIG. 26 shows the percentage of reduction of one-chain HMWK after 30 minutes FXIIa activation in neat plasma samples BRH745049, BRH745062, and BRH745063.

Protein Simple Western was compared with traditional Western Blot assay in detecting plasma activation. As shown in FIGS. 20 and 21, the former (right panel) is more sensitive than the latter (left panel).

Example 8

Ex Vivo Activation of pKal as a Biomarker

The ex vivo activation of prekallikrein to plasma kallikrein (pKal) in plasma can be used, for example, as both a pharmacodynamic (PD) biomarker to provide evidence of the bioactivity of therapeutic inhibitors of pKal, such as DX-2930, and for the detection of activated pKal in disease samples.

Figure 31:
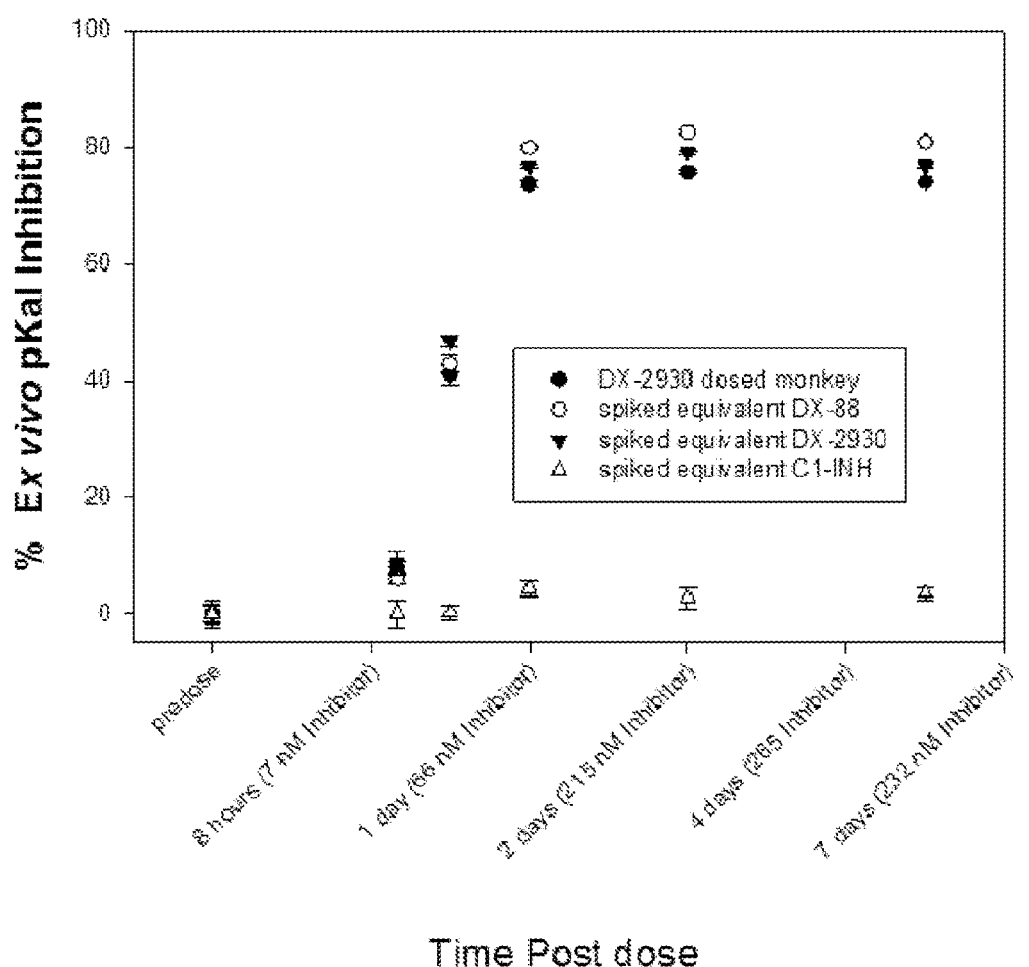
FIG. 31 is a graph showing the percent inhibition of pKal activity in plasma samples from monkeys treated with DX-2930 and inhibition of pKal activity in plasma samples spiked in vitro with DX-88 (ecallantide), C1-INH, or DX-2930. The percent inhibition was measured using an exemplary ex vivo pKal activation assay. Error bars represent standard error of the mean.

In a first experiment, plasma from a cynomolgus monkey dosed with a single SC injection of DX-2930 (5 mg/kg) was obtained and activated with 10 nM FXIIa to generate active pKal that was monitored using a synthetic substrate (Pro-Phe-Arg-AMC). Corn trypsin inhibitor was added to stop the FXIIa activation prior to the addition of the substrate. The percent inhibition observed in plasma from dosed cynomolgus monkey samples matched that of prepared plasma samples spiked with a molar equivalent of either DX-2930 or ecallantide (FIG. 31). It is evident that the plasma concentration of DX-2930 reached a drug level (~265 nM) that inhibited approximately 80% of the pKal activity that was generated by the ex vivo addition of FXIIa. FIG. 31 also shows that equal amounts of pKal inhibition were observed with an equivalent concentration of ecallantide. In contrast, equivalent concentrations of C1-INH added to the plasma did not inhibit pKal that was activated by FXIIa in this ex vivo activation assay.

Figure 32:
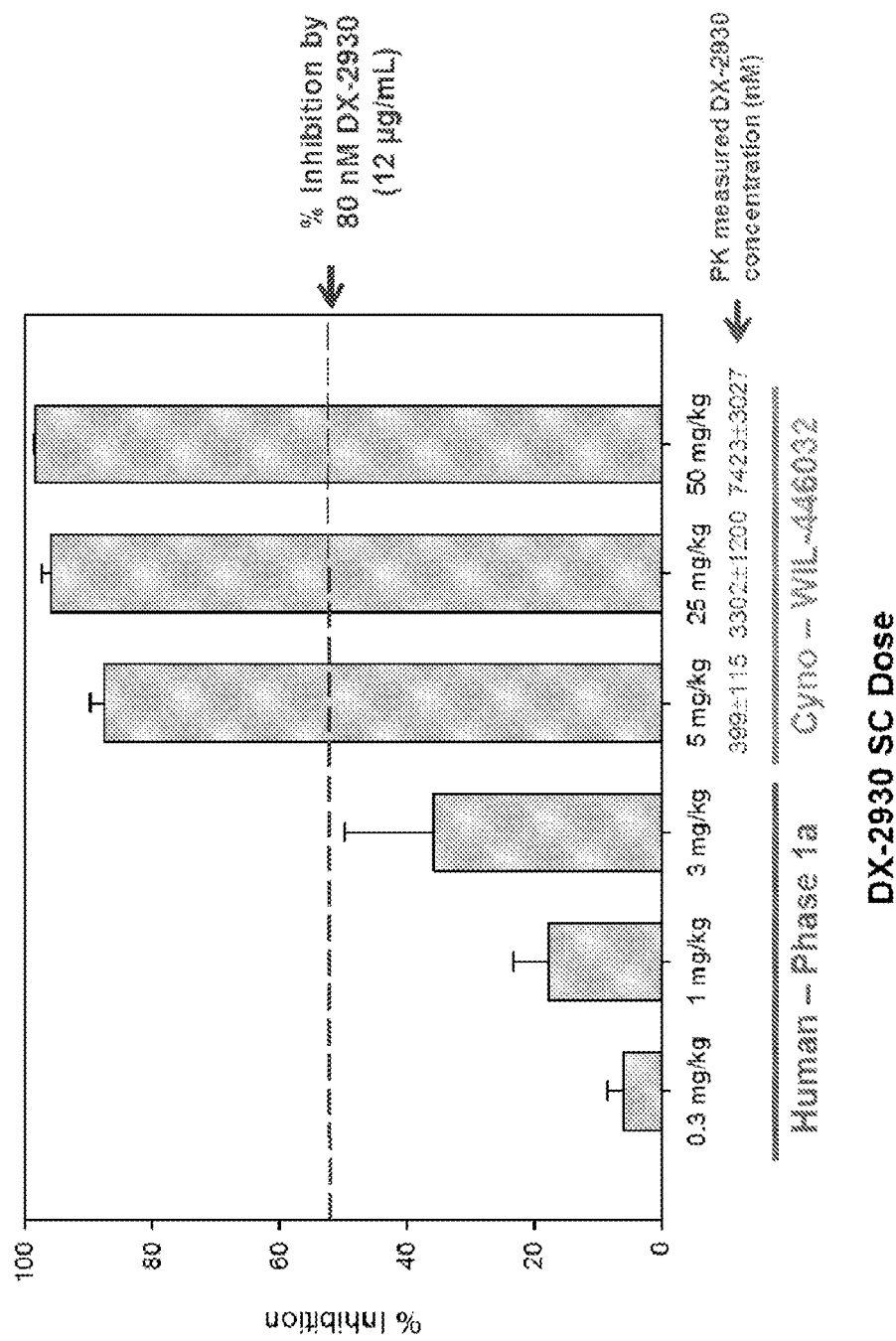
FIG. 32 is a graph showing the percent ex vivo inhibition of pKal activity in plasma from humans and monkeys treated with differing doses of DX-2930. The percent inhibition was measured using an exemplary ex vivo pKal activation assay. The dashed line shows the percent inhibition observed with 80 nM DX-2930, which is a concentration that matches the $C_{max}$ of a therapeutically effective level of ecallantide.

In a second experiment, plasma was obtained from cynomolgus monkeys dosed with five weekly SC injections of different doses of DX-2930 and citrated plasma was obtained from humans (n=6) in a phase 1a clinical study that received a single SC injection of DX-2930 at different doses. The plasma samples were activated with FXIIa and the resulting pKal activity was measured using a synthetic substrate (Pro-Phe-Arg-AMC). Corn trypsin inhibitor was added to stop the FXIIa activation prior to the addition of substrate. The percent inhibition was determined using the pKal activity present in the pre-dose plasma sample from each individual as a base-line. FIG. 32 shows that the percent inhibition increased in both human and monkey plasma samples with increasing doses of DX-2930.

The results from these two experiments show that the ex vivo activation assay is useful as a PD biomarker for the bioactivity of therapeutic inhibitors of pKal.

Example 9

Ex Vivo Inhibition of pKal Activity in DX-2930 Phase 1A Study Plasma Samples The ex vivo inhibitory activity (bioactivity) of DX-2930 in plasma derived from human subjects administered subcutaneously with DX-2930 was investigated in this study.

Materials
- DX-2930 (106.7 mg/ml=732 µM)
- Human FXIIa—ERL HFXIIa 2790P (1.72 mg/ml=25.3 µM)
- Corn Trypsin Inhibitor (CTI)—ERL CTI 360 (1.54 mg/ml=123 µM)
- Peptide Substrate=PFR-AMC, Sigma Cat#99273, Lot 037K1207.
- Assay Buffer=20 mM Tris pH 7.5, 150 mM NaCl, 1 mM EDTA, 0.1% Triton X-100, 0.1% PEG-8000
- Corning 96-well white polystyrene microplates Cat#3789
- Spectramax M2 plate reader
- Citrated Plasma collected in DX-2930 Phase 1A study Methods 1:40 diluted plasma was activated by the addition of 10 nM FXIIa for 2 minutes at room temperature. FXIIa was then quenched by the addition of 100 nM CTI, and the proteolytic activity of plasma kallikrein (pKal) was then assessed by a further 1:10 dilution of sample plasma and addition of 10 µM fluorescent peptide substrate PFR-AMC. Each plasma sample was reported as rate of pKal activity, which was converted to "% Inhibition" based on Pre-dose controls for each individual.

Results

Figure 33:
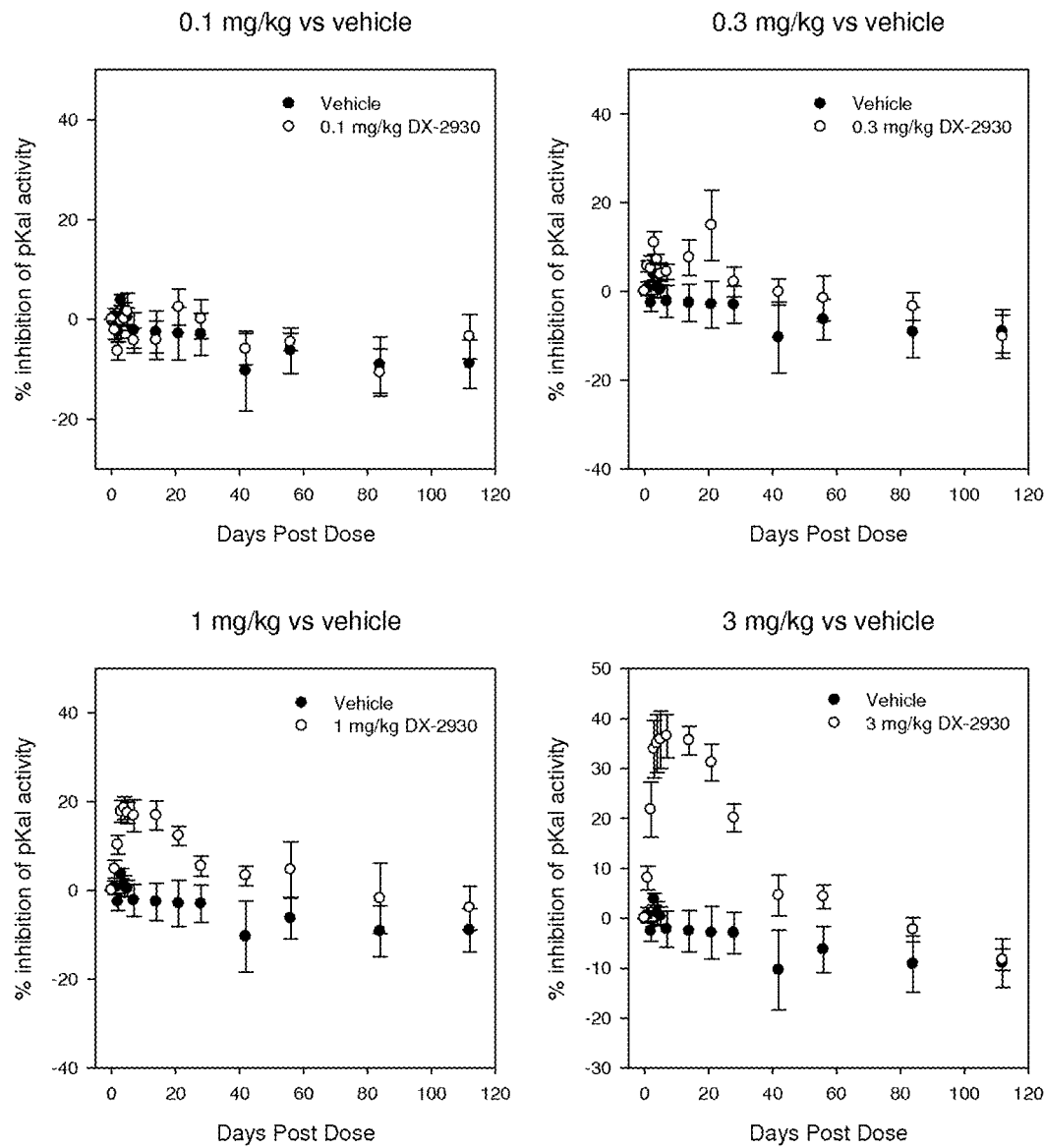
FIG. 33 is a series of plots showing the "% Inhibition of pKal activity" in plasma samples from DX-2930 Phase 1 study, comparing average inhibition of each day post dose for each dose group compared to corresponding samples in the vehicle control group. Error bars are standard error.

Citrated plasma samples were obtained from healthy subjects in the DX-2930 phase 1a study and analyzed using an Ex Vivo Bioactivity Assay in Plasma. Significant inhibition of pKal activity was observed in dose groups 3 (1.0 mg/kg DX-2930) and 4 (3.0 mg/kg DX-2930), achieving approximately 19% and 36% maximal inhibition of pKal activity, respectively (FIG. 33). The inhibition that was achieved in groups 3 and 4 was sustained and was consistent with an apparent half-life of approximately 20 days. Inhibition of pKal activity in dose groups 1 (0.1 mg/kg DX-2930) and 2 (0.3 mg/kg DX-2930) was not significant.

These results further demonstrate that the ex vivo activation assay is useful as a PD biomarker for the bioactivity of therapeutic inhibitors of pKal.

Example 10

Analysis of DX-2930 Bioactivity in Phase 1a Study Samples from the Western Blot Assay The bioactivity of DX-2930 in the plasma of human subjects treated with DX-2930 was investigated using the Western blot assay described herein.

The Western blot assay was performed using citrated plasma samples obtained from subjects on Day 1 (prior to DX-2930 or placebo dosing), on Day 5, or Day 28 following dosing with either DX-2930 or placebo. The samples were analyzed by Western blot using an antibody that detects high molecular weight kininogen (HMWK), the substrate for active plasma kallikrein, which is the target enzyme that is inhibited by DX-2930. Plasma kallikrein acts on HMWK to generate the pro-inflammatory peptide bradykinin and a 2-chain, which is known as the cleaved form of HMWK that was detected by Western blot analysis. Plasma samples untreated and treated with activated coagulation Factor XIIa (FXIIa) were analyzed. FXIIa converts the inactive prekallikrein in the plasma to activated plasma kallikrein.

Figure 34:
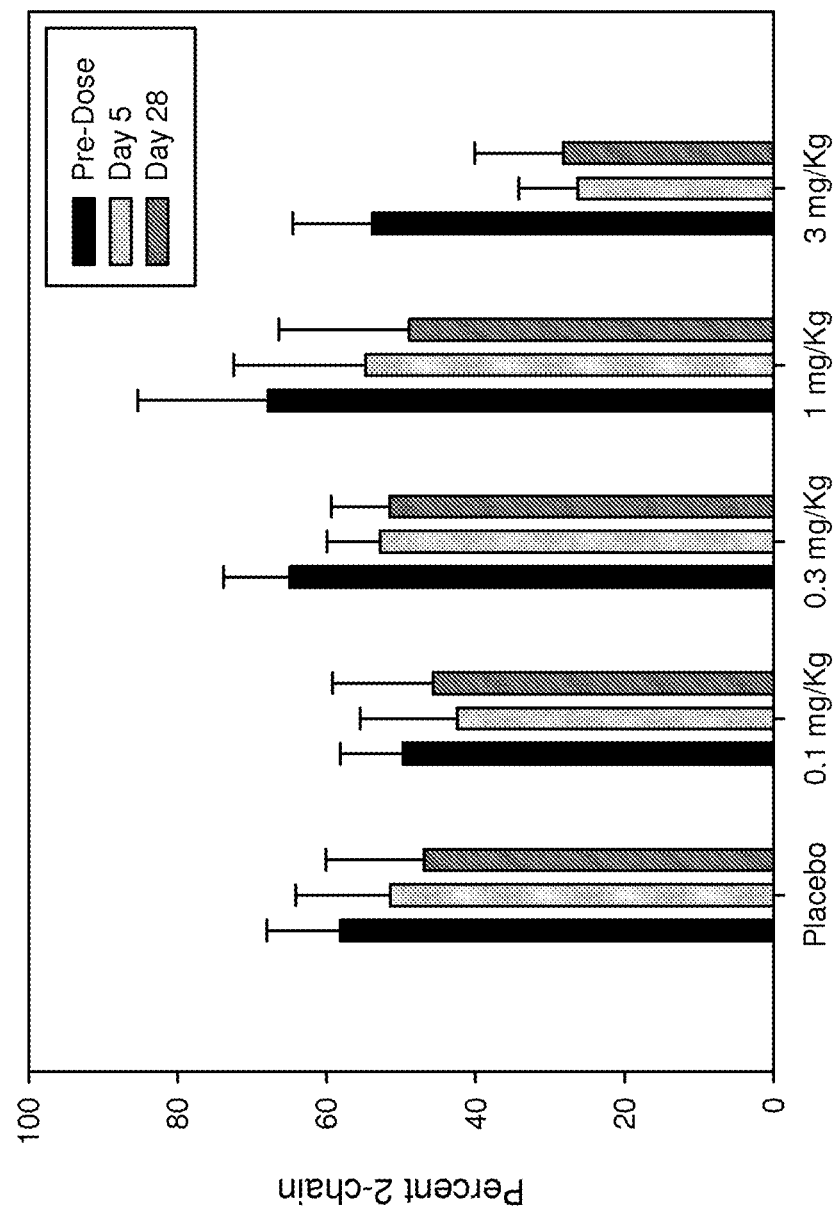
FIG. 34 is a graph showing Western blot data from DX-2930 Phase 1a subjects following FXIIa treatment. Error bars were calculated using the standard deviation between subjects. Group 1 subjects were dosed at 0.1 mg/Kg, Group 2 subjects were dosed at 0.3 mg/Kg Group 3 subjects were dosed at 1 mg/Kg, and Group 4 subjects were dosed at 3 mg/Kg.

The results obtained from this study show that FXIIa treated samples from subjects dosed with 3 mg/Kg DX-2930 (Group 4) exhibited statistically lower percentage of 2-chain HMWK (cleaved HMWK) at Day 5 (p=0.0011) and Day 28 (p=0.0028) than the pre-dose samples from these subjects. This is evidence of DX-2930 bioactivity against plasma kallikrein-mediated proteolysis of its endogenous substrate (HMWK) (FIG. 34). The reduction in the percentage of 2-chain HMWK observed in Group 4 trended lower than that observed in other dose groups or the placebo treated group.

Figure 35:
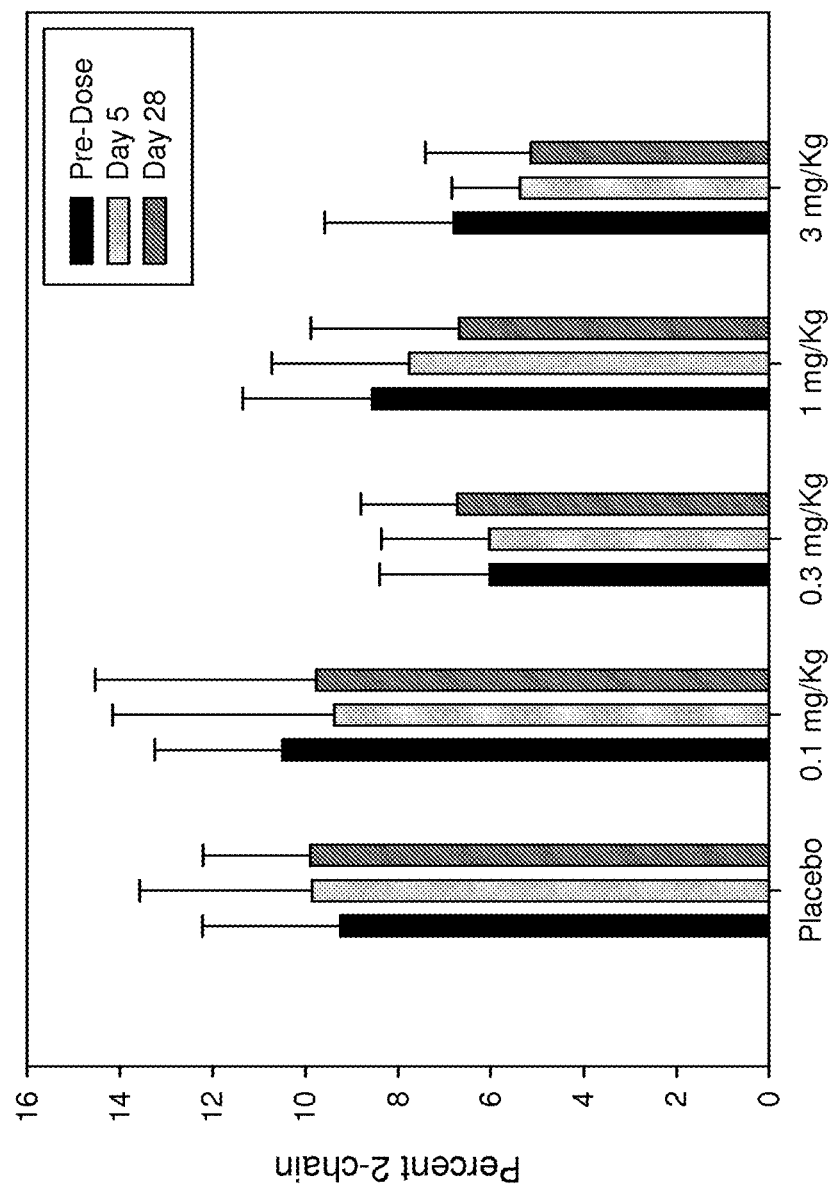
FIG. 35 shows a graph of Western blot data from DX-2930 Phase 1a subjects in the absence of FXIIa treatment. Error bars were calculated using the standard deviation between subjects. Group 1 subjects were dosed at 0.1 mg/Kg, Group 2 subjects were dosed at 0.3 mg/Kg Group 3 subjects were dosed at 1 mg/Kg, and Group 4 subjects were dosed at 3 mg/Kg.

Further, samples from subjects dosed with DX-2930 at 0.3, 1, or 3 mg/Kg that were not treated with FXIIa displayed a lower percentage of 2-chain HMWK than that observed in the placebo or 0.1 mg/Kg doses (FIG. 35).

Taken together, these results further demonstrate that the Western blot assay is useful as a PD biomarker for the bioactivity of therapeutic inhibitors of pKal.

EQUIVALENTS AND SCOPE

Those skilled in the art will recognize, or be able to ascertain using no more than routine experimentation, many equivalents to the specific embodiments of the present disclosure described herein. The scope of the present present disclosure is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The present disclosure includes embodiments in which exactly one member of the group is present in, employed in, or otherwise relevant to a given product or process. The present disclosure includes embodiments in which more than one, or all of the group members are present in, employed in, or otherwise relevant to a given product or process.

Furthermore, the present disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the present disclosure, or aspects of the present disclosure, is/are referred to as comprising particular elements and/or features, certain embodiments of the present disclosure or aspects of the present disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the present disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the present disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. An ex vivo activation method, comprising:
placing an activator of the plasma kallikrein (pKal) system in a plasma sample obtained from a subject to produce a mixture, wherein the activator is Factor XIIa (FXIIa);
incubating the mixture;
measuring levels of intact high molecular weight kininogen (HMWK), cleaved HMWK, or both, in the plasma sample before and after the incubation;
determining a reduction of intact HMWK in the sample after the activation and/or an elevated level of the cleaved HMWK in the sample after the activation; and
administering a therapeutic agent to the subject if the plasma sample obtained from the subject has an elevated level of the cleaved HMWK as compared to a predetermined value;
wherein the therapeutic agent is DX-2930, DX-2922, DX-88, or EpiKal-2.

2. The method of claim 1, wherein the subject is a human patient having or at risk of having a disease associated with pKal.

3. The method of claim 2, wherein the human patient has been subjected to a treatment of the disease.

4. The method of claim 3, wherein the human patient has HAE and has been treated with a pKal inhibitor, which is DX-2930, DX-2922, DX-88, or EpiKal-2.

5. An ex vivo assay for determining plasma kallikrein (pKal) activity in a sample, comprising:
placing a pKal system activator and a labeled synthetic peptide substrate of pKal in a plasma sample obtained from a subject to produce a mixture, wherein the activator is Factor XIIa (FXIIa), and wherein the peptide substrate comprises a motif of PFR;
incubating the mixture;
measuring the activity of pKal in the mixture based on a cleavage rate of the substrate; and
administering a therapeutic agent to the subject if the plasma sample obtained from the subject has an elevated level of pKal activity compared to a predetermined value;
wherein the therapeutic agent is DX-2930, DX-2922, DX-88, or EpiKal-2.

6. The assay of claim 5, wherein the labeled substrate releases a detectable signal after being cleaved by pKal and the cleavage rate of the substrate is determined based on the magnitude of the detectable signal.

7. The assay of claim 5, wherein the subject is a human patient having or at risk of having a disease associated with pKal.

8. The assay of claim 7, wherein the human patient has been subjected to a treatment of the disease.

9. The assay of claim 8, further comprising evaluating the efficacy of the treatment; wherein a reduced level of pKal activity as compared to the pKal activity before the treatment or a reduced level of pKal activity over the course of the treatment indicates that the treatment is effective; and continuing the treatment on the subject, if the treatment is identified as effective.

10. The assay of claim 8, wherein the human patient has hereditary angioedema (HAE) and has been treated with a pKal inhibitor, which is DX-2930, DX-2922, DX-88, or EpiKal-2.

11. The method of claim 2, wherein the disease associated with pKal is hereditary angioedema (HAE).

12. The method of claim 3, wherein the plasma sample is obtained after or during the course of the treatment.

13. The method of claim 12, further comprising evaluating the efficacy of the treatment, and continuing the treatment on the subject who is identified as being responsive to the treatment, a reduced level of cleaved HMWK after the treatment as compared to the level of cleaved HMWK before the treatment or a reduced level of cleaved HMWK over the course of the treatment indicating that the subject is responsive to the treatment.

14. The method of claim 8, wherein the sample is obtained after or during the course of the treatment.

15. The method of claim 7, wherein the disease associated with pKal is hereditary angioedema (HAE).

* * * * *